(12) United States Patent
Torch

(10) Patent No.: US 7,515,054 B2
(45) Date of Patent: Apr. 7, 2009

(54) BIOSENSORS, COMMUNICATORS, AND CONTROLLERS MONITORING EYE MOVEMENT AND METHODS FOR USING THEM

(76) Inventor: William C. Torch, 4100 Ramrod Cir., Reno, NV (US) 89509

( * ) Notice: Subject to any disclaimer, the term of this patent is extended or adjusted under 35 U.S.C. 154(b) by 312 days.

(21) Appl. No.: 11/097,788

(22) Filed: Apr. 1, 2005

(65) Prior Publication Data

US 2009/0058660 A1 Mar. 5, 2009

Related U.S. Application Data

(60) Provisional application No. 60/559,135, filed on Apr. 1, 2004.

(51) Int. Cl.
  *G08B 13/14* (2006.01)
  *A61B 5/00* (2006.01)
  *A61B 3/14* (2006.01)
(52) U.S. Cl. .................. 340/573.1; 340/575; 600/300; 351/206; 351/207; 351/209; 351/210
(58) Field of Classification Search ............. 340/573.1, 340/575–576; 600/300; 351/205–206, 209–210
See application file for complete search history.

(56) References Cited

U.S. PATENT DOCUMENTS

| | | | |
|---|---|---|---|
| 3,798,599 A | 3/1974 | Kafafian | |
| 3,863,243 A | 1/1975 | Skolnick et al. | |
| 3,966,310 A | * 6/1976 | Larson | 351/221 |
| 4,359,724 A | 11/1982 | Zimmerman et al. | |
| 4,815,839 A | 3/1989 | Waldorf | |
| 4,850,691 A | 7/1989 | Gardner et al. | |
| 4,894,777 A | * 1/1990 | Negishi et al. | 600/558 |
| 4,953,111 A | 8/1990 | Yamamoto et al. | |

(Continued)

FOREIGN PATENT DOCUMENTS

EP     0 679 984     4/1995

(Continued)

OTHER PUBLICATIONS

PCT International Search Report for PCT/US2005/011104, Applicant: Dr. William Torch, Forms PCT/ISA/210 & 220, dated Mar. 21, 2006 (9 pages).

(Continued)

*Primary Examiner*—Benjamin C Lee
(74) *Attorney, Agent, or Firm*—William A. English; Vista IP Law Group LLP

(57) ABSTRACT

Biosensor, communicator, and/or controller apparatus, systems, and methods are provided for monitoring movement of a person's eye. The apparatus includes a device configured to be worn on a user's head, a light source for directing light towards one or both eyes of the user, one or more image guides on the device for viewing one or both eyes of the user, and one or more cameras carried on the device and coupled to the image guides for acquiring images of the eyes and/or the user's surroundings. The apparatus may include a cable and/or a transmitter for transmitting image data from the camera to a remote location, e.g., to processor and/or display for analyzing and/or displaying the image data. A system including the apparatus may be used to monitor one or more oculometric parameters, e.g., pupillary response, and/or to control a computer using the user's eyes instead of a mouse.

28 Claims, 31 Drawing Sheets

U.S. PATENT DOCUMENTS

| | | | |
|---|---|---|---|
| 5,214,456 A | | 5/1993 | Gersten |
| 5,345,281 A | | 9/1994 | Taboada et al. |
| 5,402,109 A | | 3/1995 | Mannik |
| 5,469,143 A | | 11/1995 | Cooper |
| 5,478,239 A | * | 12/1995 | Fuerst et al. ............... 473/438 |
| 5,481,622 A | | 1/1996 | Gerhardt et al. |
| 5,566,067 A | | 10/1996 | Hobson et al. |
| 5,570,698 A | | 11/1996 | Liang et al. |
| 5,682,144 A | | 10/1997 | Mannik |
| 5,689,241 A | | 11/1997 | Clarke, Sr. et al. |
| 5,704,369 A | * | 1/1998 | Scinto et al. ............... 600/558 |
| 5,748,113 A | | 5/1998 | Torch |
| 5,778,893 A | * | 7/1998 | Potter ....................... 128/898 |
| 5,795,306 A | * | 8/1998 | Shimotani et al. .......... 600/558 |
| 5,867,587 A | | 2/1999 | Aboutalib et al. |
| 5,956,125 A | * | 9/1999 | Rosse et al. ................. 351/221 |
| 6,003,991 A | | 12/1999 | Viirre |
| 6,087,941 A | | 7/2000 | Ferraz |
| 6,090,051 A | * | 7/2000 | Marshall .................... 600/558 |
| 6,097,295 A | | 8/2000 | Griesinger et al. |
| 6,116,736 A | * | 9/2000 | Stark et al. ................. 351/206 |
| 6,163,281 A | | 12/2000 | Torch |
| 6,246,344 B1 | | 6/2001 | Torch |
| 6,246,779 B1 | * | 6/2001 | Fukui et al. ................ 382/103 |
| 6,247,813 B1 | * | 6/2001 | Kim et al. .................. 351/206 |
| 6,260,968 B1 | | 7/2001 | Stark et al. |
| 6,334,683 B2 | | 1/2002 | Apple et al. |
| 6,346,929 B1 | | 2/2002 | Fukushima |
| 6,388,639 B1 | * | 5/2002 | Hoshino et al. ............... 345/8 |
| 6,542,081 B2 | | 4/2003 | Torch |
| 6,820,979 B1 | * | 11/2004 | Stark et al. .................. 351/206 |
| 6,867,752 B1 | | 3/2005 | Yamazaki et al. |
| 6,997,556 B2 | * | 2/2006 | Pfleger ....................... 351/246 |
| 7,071,831 B2 | | 7/2006 | Johns |
| 7,120,880 B1 | * | 10/2006 | Dryer et al. ................. 715/863 |
| 2001/0028309 A1 | | 10/2001 | Torch |
| 2002/0024633 A1 | * | 2/2002 | Kim et al. ................... 351/206 |
| 2004/0061680 A1 | | 4/2004 | Taboada |
| 2005/0007552 A1 | | 1/2005 | Fergason et al. |
| 2005/0099601 A1 | * | 5/2005 | MacDougall et al. ....... 351/209 |

FOREIGN PATENT DOCUMENTS

| | | |
|---|---|---|
| EP | 0 984 347 | 8/1998 |
| WO | 2006092022 | 9/2006 |

OTHER PUBLICATIONS

PCT Written Opinion of the International Search Authority for PCT/US2005/011104, Applicant: Dr. William C. Torch, Form PCT/ISA/237, dated Mar. 21, 2006 (11 pages).

Hewlett-Packard GMBH: "Helmet-Mounted Display for Data Recall and Direct Consultation During Surgical Operation," Jan. 1996, Research Disclosure, Mason Publications, Hampshire, GB.

* cited by examiner

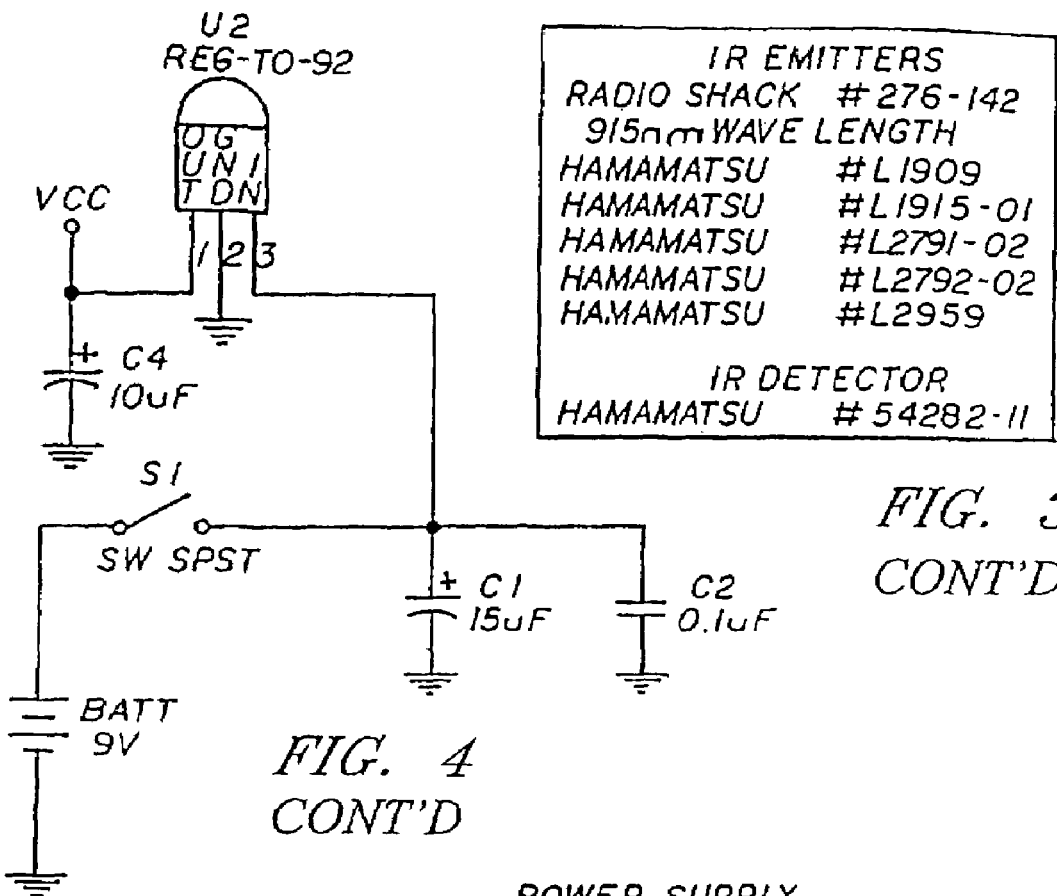
*FIG. 3*
*CONT'D*
*FIG. 4*
*CONT'D*
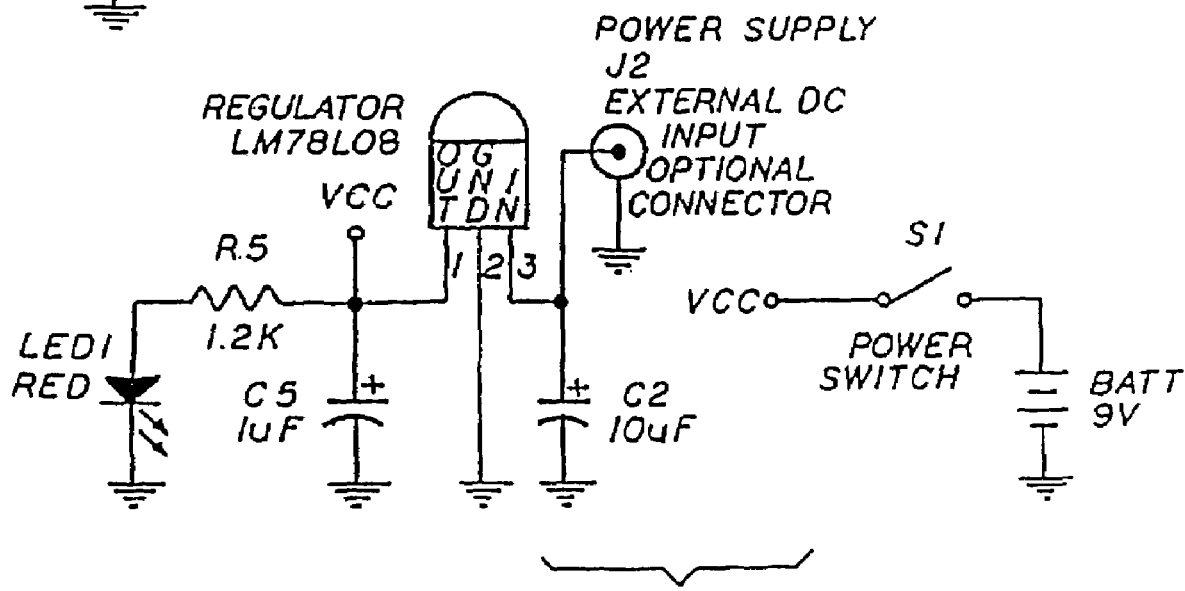
*FIG. 3*
*CONT'D*

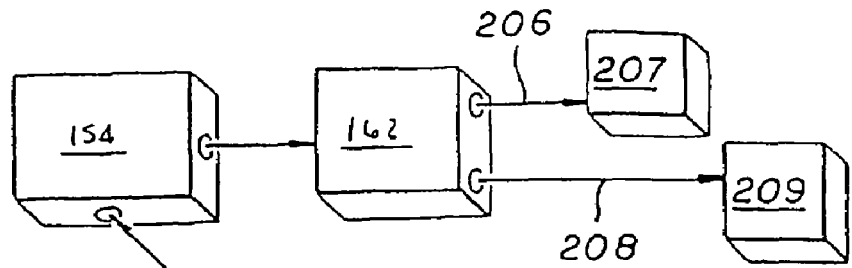
FIG. 8
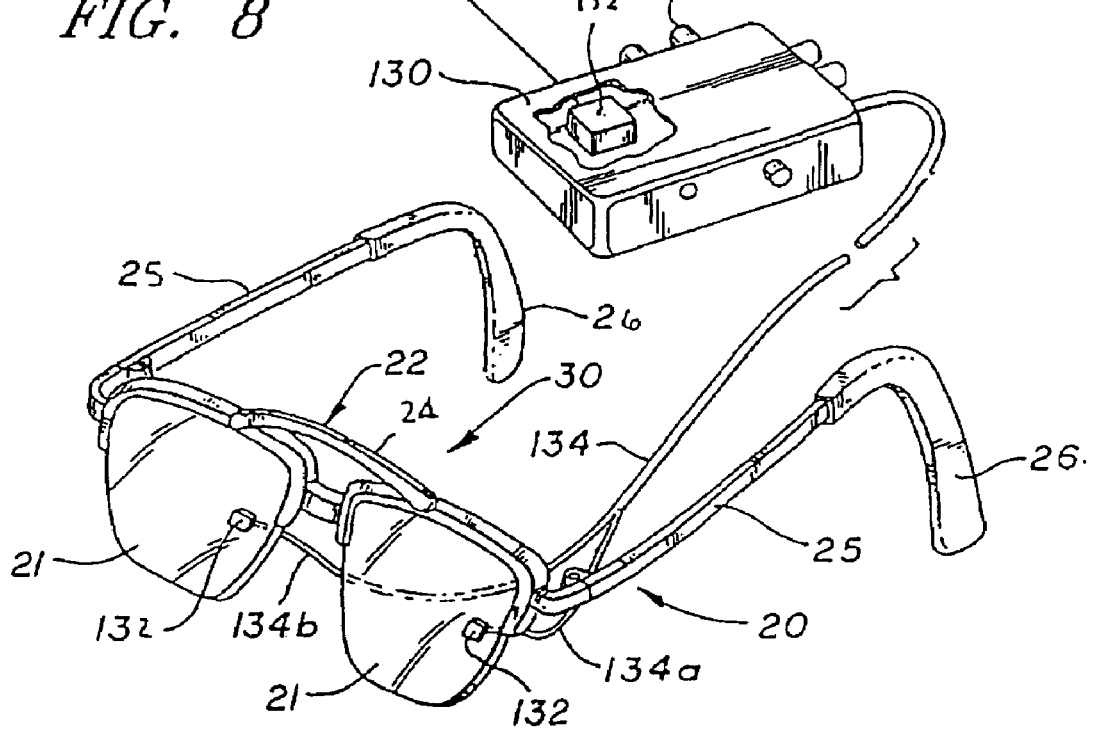
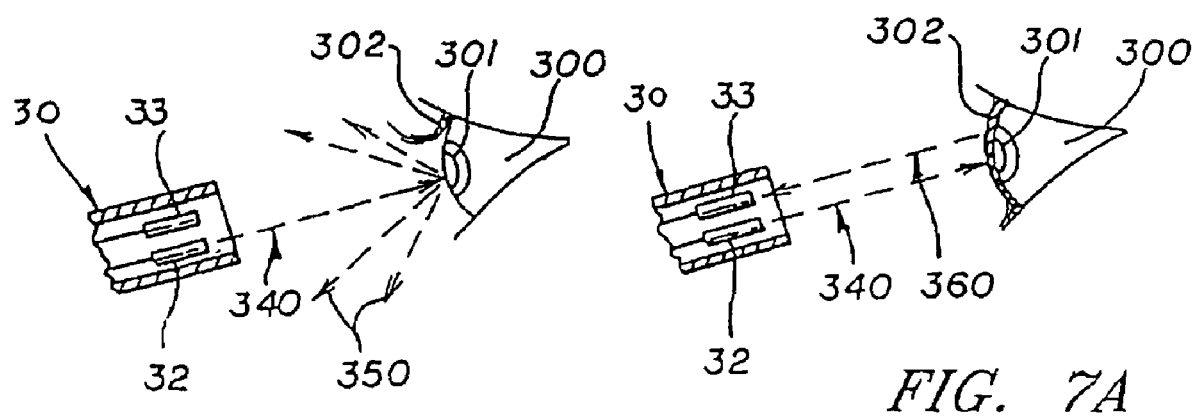
FIG. 6A
FIG. 7A

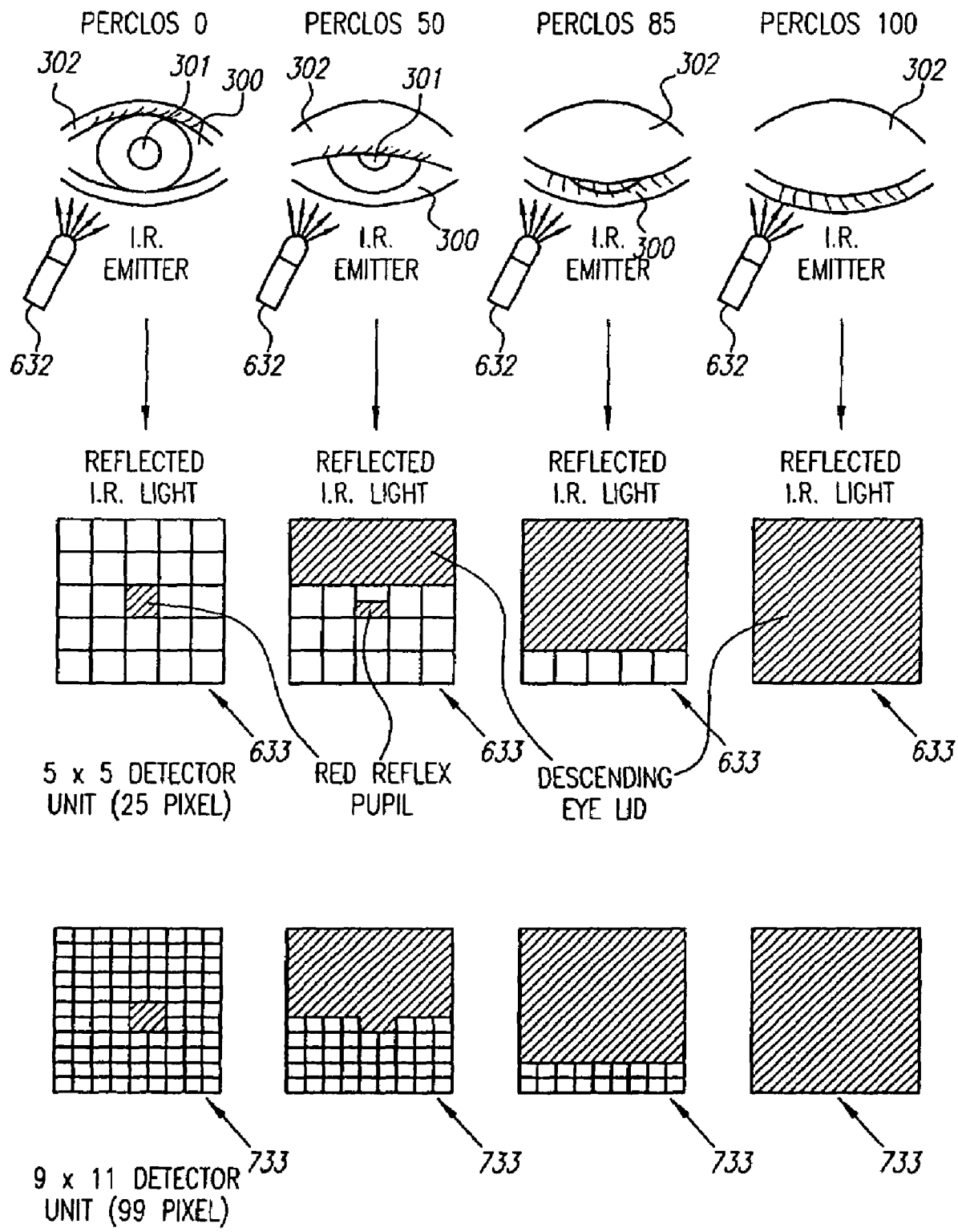
FIG. 12DI  FIG. 12DII  FIG. 12DIII  FIG. 12DIV

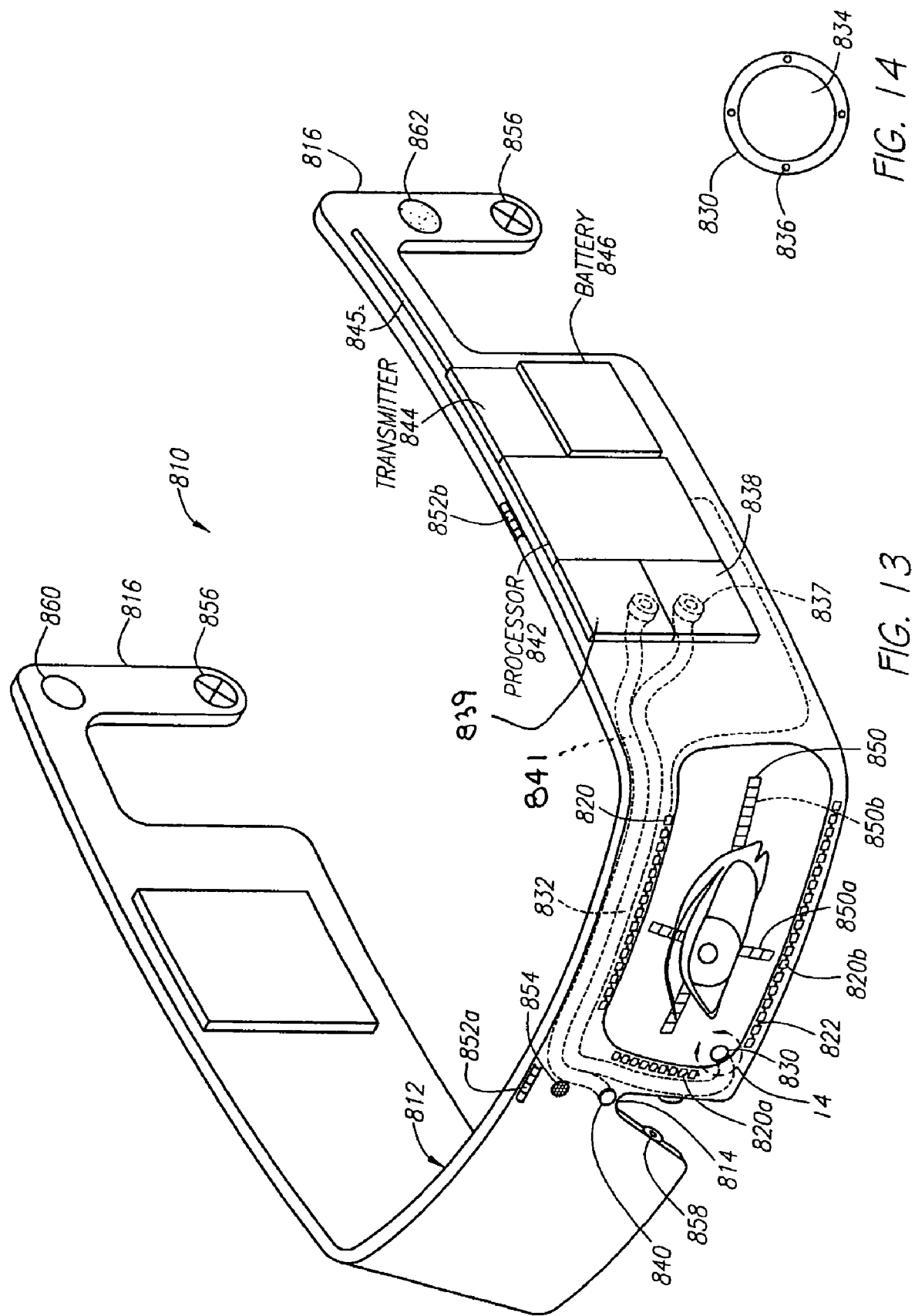

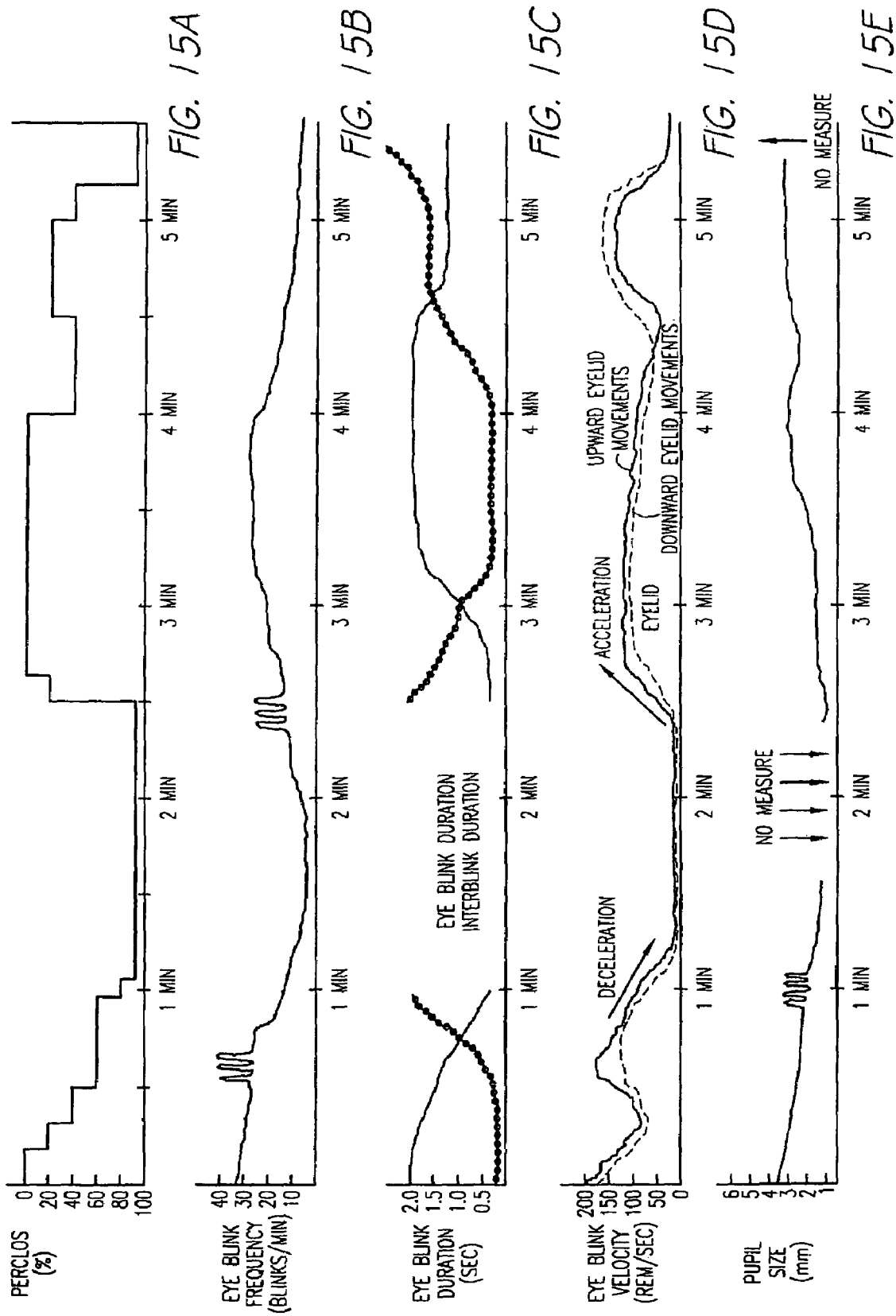

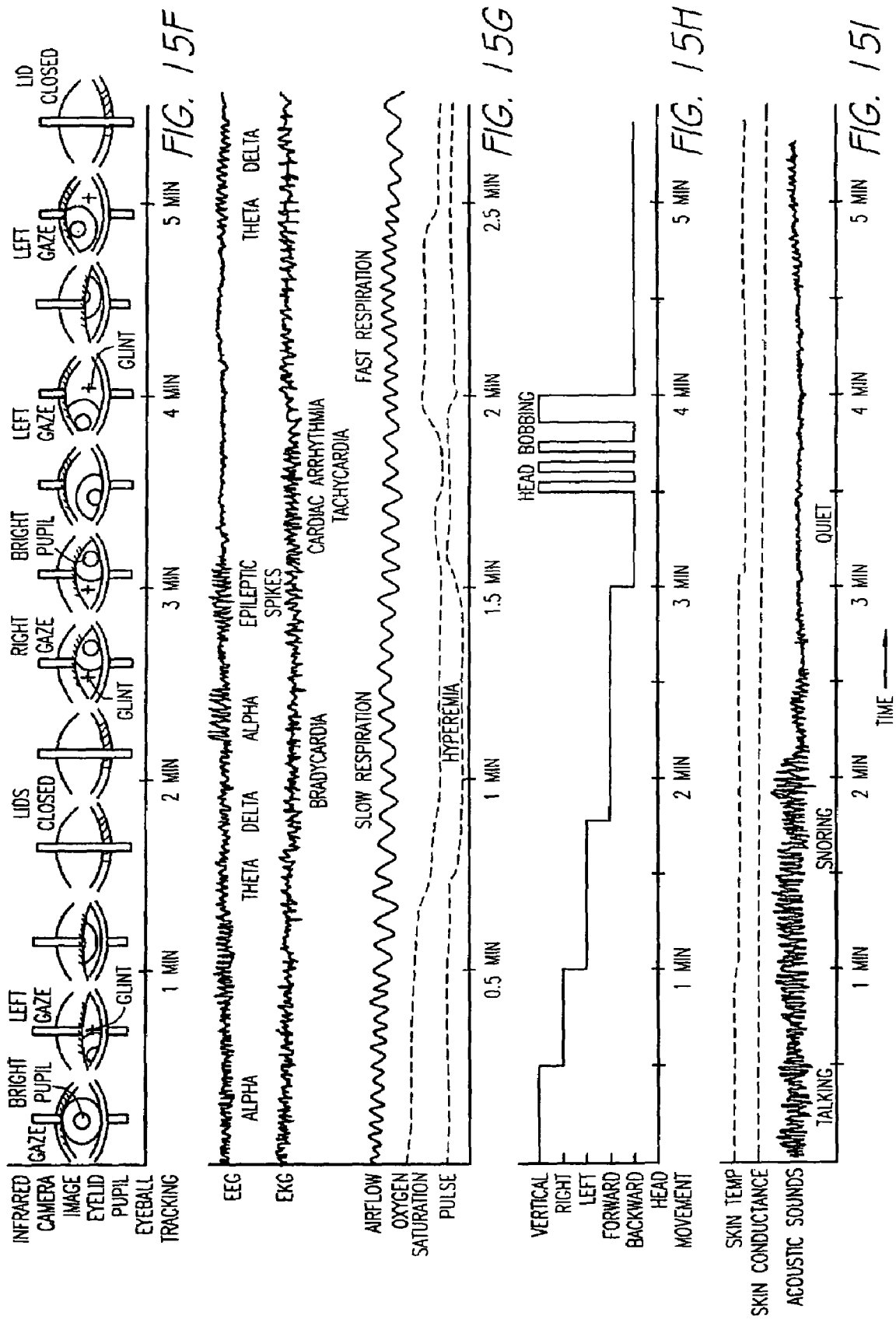

US 7,515,054 B2

BIOSENSORS, COMMUNICATORS, AND CONTROLLERS MONITORING EYE MOVEMENT AND METHODS FOR USING THEM

RELATED-APPLICATION INFORMATION

This application claims benefit of provisional application Ser. No. 60/559,135, filed Apr. 1, 2004, the entire disclosure of which is expressly incorporated by reference herein.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Grant No. 1 R43 CE 00151-01 awarded by the Department of Health and Human Services, Public Health Services, Centers for Disease Control (CDC), and Department of Defense (US Army) Contract No. W81 XWH-05-C-0045.

FIELD OF THE INVENTION

The present invention relates generally to apparatus, systems, and methods for monitoring movement of a human eye, e.g., for monitoring fatigue, purposeful communication, and/or controlling devices based upon movement of an eye, eyelid, and/or other components of the eye or eyes of a person.

BACKGROUND

It has been suggested to use movement of the human eye to monitor involuntary conditions, such as a person's wakefulness or drowsiness. For example, U.S. Pat. No. 3,863,243 discloses a device that sounds an alarm to warn a person using the device that they are beginning to fall asleep. The device includes a frame similar to a set of eyeglasses onto which is mounted an optical fiber and a photocell that are directed towards the user's eye when the frame is worn. The photocell detects the intensity of light reflected off of the user's eye, i.e., either by the eyelid when the eye is closed or the eye surface when the eye is open. A timer distinguishes between regular blinks, and an extended time period during which the eye is closed, i.e., a time period that may indicate that the person is falling asleep. When a threshold time elapses, an alarm is sounded to notify and/or wake the user.

Another device is the Alertness Monitor by MTI Research Inc., which may be mounted on safety glasses, and emits a continuous infrared beam of light along the axis of the eyelid at a strategic position where the beam cannot be broken by the eyelashes except during an eyeblink, giving it the ability to measure eyeblink frequency. Other devices, such as those disclosed in U.S. Pat. Nos. 5,469,143 and 4,359,724, directly engage the eyelid or eyebrow of a user to detect movement of the eye and activate an alarm when a drowsiness condition is detected. Such devices may include mechanical devices, e.g., a mechanical arm, or a piezo-electric film against the eyelid.

It has been suggested to mount cameras or other devices to a dashboard, roof, or other location in a vehicle to monitor a driver's awareness. Such devices, however, require the user to maintain constant eye contact with the camera. In addition, they do not monitor eyelid movement if the user turns his head sideways or downwards, turns around, exits the vehicle, if the user moves around rapidly, or if the camera moves relative to the individual. Further, such cameras may violate privacy and/or have problems seeing through eyeglasses, sunglasses, or even contact lenses, and may not operate effectively in sunlight.

SUMMARY

The present invention is directed to apparatus, systems, and methods for monitoring movement of one or more eyes, eyelids, and/or pupils of a subject. Generally, humans blink at least about 5-30 times per minute, or about 7,000-43,000 times per day. Each involuntary-reflexive blink lasts about 200-300 milliseconds, generally averaging about 250 milliseconds, amounting to about 1,750-10,800 seconds per day of eye closure due to involuntary blinking. As tiredness or sleepiness occurs, the eye blink may get longer and slower and/or the blink rate may vary, and/or the eyelids may begin to droop with small amplitude eye lid blinks, e.g., until the eyes begin to close for short term "microsleeps," i.e., sleep conditions that last for about 3-5 seconds or longer, or for prolonged sleep. Furthermore, the pupils may constrict more sluggishly, show unstable fluctuations in size, shrinking progressively in diameter, and/or demonstrate delayed responses to light flashes (i.e. delayed pupil response latency) as sleepiness and fatigue progresses. In addition, other ocular manifestations of drowsiness may occur, such as slow or delayed saccadic eye tracking responses, e.g., to a stimulus (i.e., delayed saccadic response latency), with either over- or under-shooting the target, and/or a loss of directed gaze with or without binocular vergence or divergence, eye drift, or esophoria.

In one embodiment, an apparatus for monitoring eyelid, pupil, and/or eye movement is provided that includes a device configured to be worn on a person's head, a light source for directing light towards the eyes of the person when the device is worn, and first and second fiberoptic bundles coupled to the device, the first bundle positioned for viewing a first eye of the person wearing the device, the second bundle positioned for viewing a second eye of the person wearing the device. The apparatus may also include a camera coupled to the first and second bundles for acquiring images of the first and second eyes.

Optionally, the apparatus may also include a third fiberoptic bundle oriented away from the user, e.g., for viewing a region towards which the user's head is turned. In addition or alternatively, the apparatus may carry one or more spatial sensors. The camera may be coupled to the first and second bundles for acquiring images of the first and second eyes, as well as to the third bundle for acquiring images of the area towards which the user's head and/or eyes are directed. The spatial sensors may allow simultaneous measuring or tracking of the user's head movement, e.g., relative to the user's eye movements. In addition, the arrays of emitters and/or sensors coupled to the camera may allow measurement of a variety of oculometric parameters of one or both eyes, such as eyelid velocity, acceleration and deceleration, eye blink frequency, "PERCLOS" (percentage of time the eyelid is open), the vertical height of the palpebral fissure (i.e. the region between the eye lids not covering the pupil), e.g., as a distance or percentage related to a completely open eye, and the like.

In another embodiment, a self-contained device is provided for detecting movement of a person's eyelid that includes a device adapted to be worn on the person's head, an emitter on the device for directing light towards an eye of the person when the device is worn, and a camera for detecting light from the emitter. The sensor produces an output signal indicating when the eye is open or closed, and a transmitter on the frame is coupled to the sensor for wireless transmission of the output signal to a remote location. The frame may also include a processor for comparing the output signal to a predetermined threshold to detect drowsiness-induced eyelid movement. Similar to the previous embodiments, the emitter and sensor may be a solid state biosensor device for emitting and detecting infrared light, or alternatively an array, e.g., one or two dimensional array, of emitters and/or sensors in a predetermined configuration on the frame, e.g., in a vertical, horizontal, diagonal, or other linear or other geometric array of more than one emitter and/or sensor oriented towards one or both eyes. In particular, an array of emitters and/or sensors may allow measurement of oculometric parameters, such as those identified elsewhere herein.

The emitter and/or sensors may be affixed to any number of points on the frame, e.g., around the lens and/or in the nose bridge, or alternatively anywhere along the frame, including near or on the nasal portion of the frame, the attachment of a temple piece of the frame, and/or surface mounted on the lens of an eyeglass. Alternatively, the emitter and/or sensor may be embedded in the lens of an eyeglass, or otherwise such that they operate through the lens. Thus, the emitter(s) and/or sensor(s) may be fixed on an eye-frame such that they move with the wearer's head movements, and continuously focus on the user's eyes in any body position, whether the user is in a vehicle, outdoors or in any other environment.

In still another embodiment, a system is provided for monitoring movement of a person's eye. The system includes a device configured to be worn on a person's head, one or more emitters on the device for directing light towards an eye of the person when the device is worn, and a camera, e.g., a CCD or CMOS device. The emitter(s) may be configured for projecting a reference frame towards the eye. The camera may be oriented towards the eye for monitoring movement of the eye relative to the reference frame. The camera may be provided on the device or may be provided remote from the device, but in relatively close proximity to the user.

Light from the emitter(s) may be emitted towards the eye of a user wearing the device to illuminate the eye(s) of the user, while projecting a reference frame onto the eye. The emitter(s) may project light "invisibly" to the user, i.e., outside the scotopic (night-vision) or photopic (day-vision) range of normal vision, e.g., in the infrared light range, such that the illumination and/or reference frame do not interfere substantially with the user's vision. The camera may image light produced by the emitters, e.g., in the infrared light range, thereby detecting the projected light as a spot of light, band of light or other "glint." Movement of the eye relative to the reference frame may be monitored with the camera. A graphical output of the movement monitored by the camera, e.g., relative to a reference frame projected onto the eye, may be monitored. For example, infrared light from the emitters may be reflected off of the retina as a "red reflex" under white light, as a white or dark black pupil under infrared light, including the image of a dark pupil using methods of subtraction known in the art.

A processor, e.g., using one or more of these methods, may detect movement of the eye's pupil, e.g., measuring movement relative to the reference frame. This movement may be graphically displayed, showing the movement of the eye's pupil relative to the reference frame. Optionally, the output signal from the one or more sensors may be correlated with video signals produced by the camera monitoring movement of the eye relative to the reference frame, e.g., to determine the person's level of drowsiness, or psycho- or neuro-physiological cognitive, emotional, and/or alertness-related state of mind.

In yet another embodiment, a method is provided for controlling a computing device or other electronic or electromechanical device (e.g. radio, television, wheel-chair, telephone, alarm system, audible, visible or tactile alerting system, etc.) using a device worn on a user's head. The device may include one or more components, similar to other embodiments described herein, including a camera having at least one objective lens directed towards at least one eye of the user. The computer device may include a display including a pointer displayed on the display. The display may include a heads-up or heads-down display attached to the device worn on the user's head or otherwise attached or disposed on the user's head, a desk computer monitor that may be disposed in front of the user, a digitally projected image on a screen (e.g., as in a drive or flight simulator), and the like. Movement of the user's eye(s) may be monitored using the camera, and movement of the eye(s) may be correlated relative to the pointer on the display to cause the pointer to follow movement of the eye(s), e.g., similar to a computer mouse. Optionally, the camera may monitor the user's eye(s) for predetermined eye activities, e.g., blinks for predetermined lengths of time, that may correspond to instructions to execute one or more commands identified with the pointer on the display, e.g., similar to "double-clicking" on a computer mouse.

Other aspects and features of the present invention will become apparent from consideration of the following description taken in conjunction with the accompanying drawings.

BRIEF DESCRIPTION OF THE DRAWINGS

FIGS. 6A-6C are sectional and front views of alternate embodiments of a device for emitting light towards and detecting light reflected from a surface of an open eye.

FIGS. 7A-7C are sectional and front views of the devices of FIGS. 6A-6C, respectively, emitting light towards and detecting light reflected from a closed eyelid.

FIG. 8 is a perspective view and block diagram of another embodiment of a system for monitoring a user based upon movement of the user's eye and/or eyelid.

FIG. 12D is a table showing the relationship between the activation of two-dimensional arrays of sensors and an eye being monitored, as the eye progresses between open and closed conditions.

FIG. 13 is a perspective view of another system for monitoring a user based upon movement of the user's eye and/or eyelid.

FIG. 14 is a detail of a camera on the frame of FIG. 13.

FIGS. 15A-15I are graphical displays of several parameters that may be monitored with the system of FIG. 13.

DETAILED DESCRIPTION OF THE PREFERRED EMBODIMENTS

Figure 1:
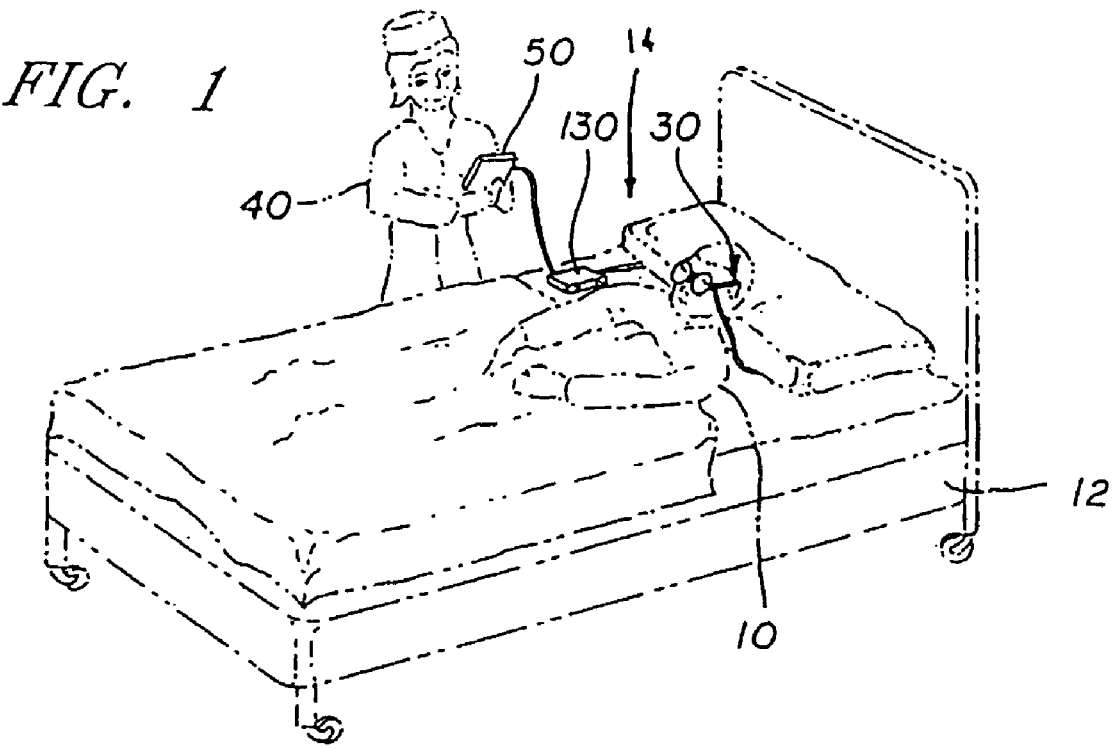
FIG. 1 is a perspective view of a patient in a hospital wearing an embodiment of an apparatus for monitoring the patient based upon movement of the patient's eye and/or eyelid.

Turning to the drawings, FIG. 1 shows a patient 10 in a bed 12 wearing a detection device 30 for detecting eye and/or eyelid movement of the patient 10. The detection device 30 may include any of the biosensor devices described herein, which may be used for monitoring voluntary movement of the eye, e.g., for purposeful communication, for monitoring involuntary eye movement, e.g., drowsiness or other conditions, and/or for controlling one or more electronic devices (not shown). The detection device 30 may be coupled to a processing box 130 that converts the detected eye and/or eyelid movement into a stream of data, an understandable message, and/or into other information, which may be communicated, for example, using a video display 50, to a medical care provider 40.

Figure 2:
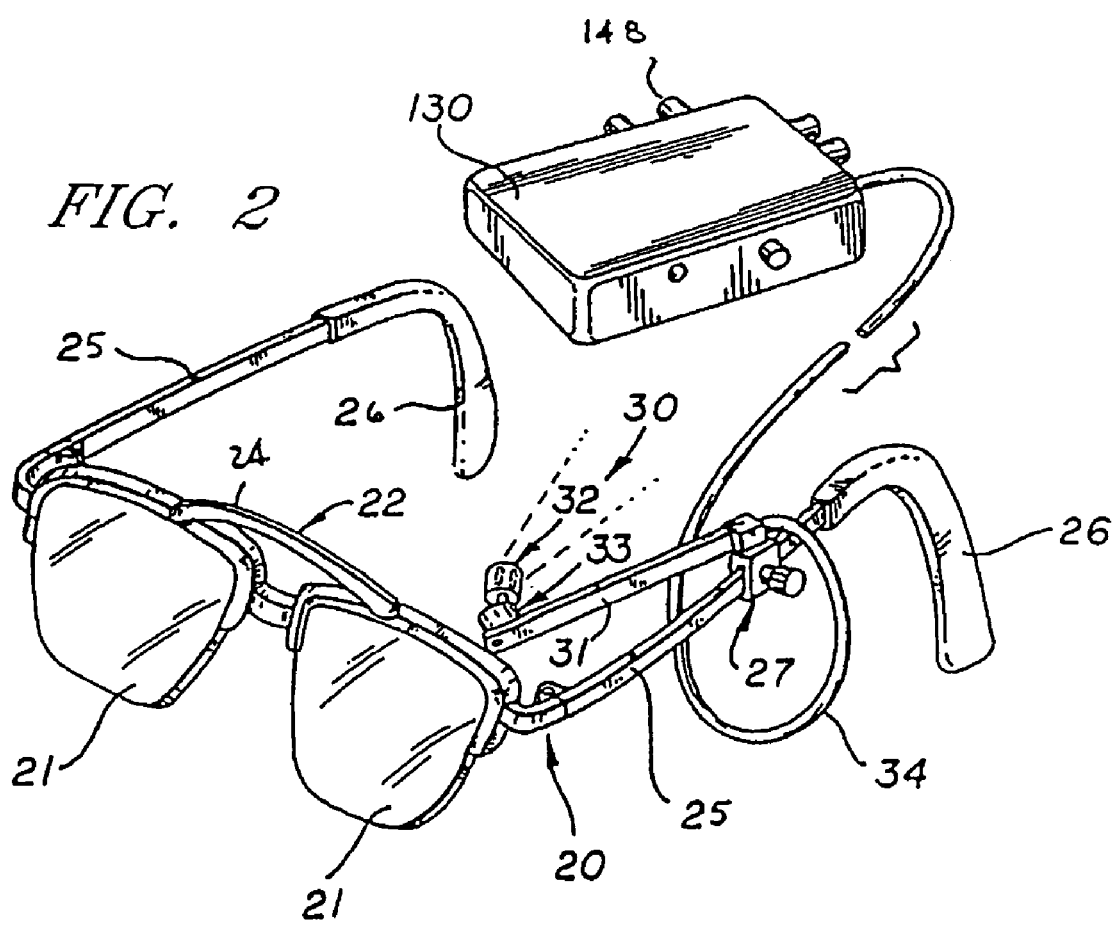
FIG. 2 is an enlarged perspective view of the embodiment of FIG. 1, including a detection device and a processing box.

Turning to FIGS. 2, 6A, and 7A, an exemplary embodiment of an apparatus or system 14 is shown that includes an aimable and focusable detection device 30 that is attachable to a conventional pair of eyeglasses 20. The eyeglasses 20 include a pair of lenses 21 attached to a frame 22, which includes bridgework 24 extending between the lenses 21, and side members or temple pieces 25 carrying ear pieces 26, all of which are conventional. Alternatively, because the lenses 21 may not be necessary, the frame 22 may also be provided without the lenses 21.

The detection device 30 includes a clamp or other mechanism 27 for attaching to one of the side members 25 and an adjustable arm 31 onto which is mounted one or more emitters 32 and sensors 33 (one shown). The emitter 32 and sensor 33 are mounted in a predetermined relationship such that the emitter 32 may emit a signal towards an eye 300 of a person wearing the eyeglasses 20 and the sensor 33 may detect the signal reflected from the surface of the eye 300 and eyelid 302. In the exemplary embodiment shown in FIGS. 6A and 7A, the emitter 32 and sensor 33 may be mounted adjacent one another.

Figure 6B:
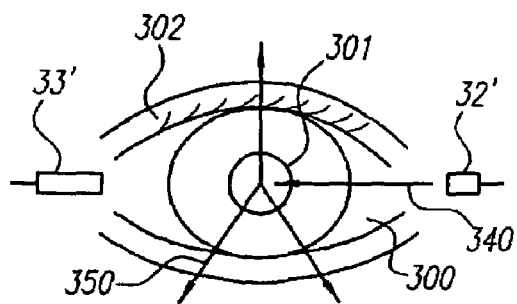
Figure 7B:
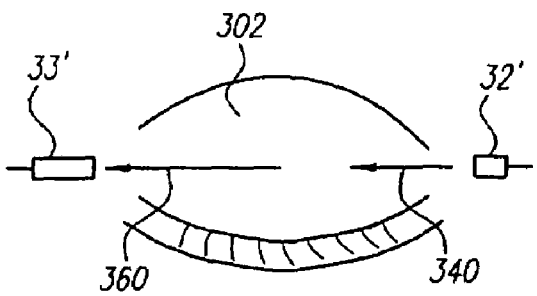
Figure 6C:
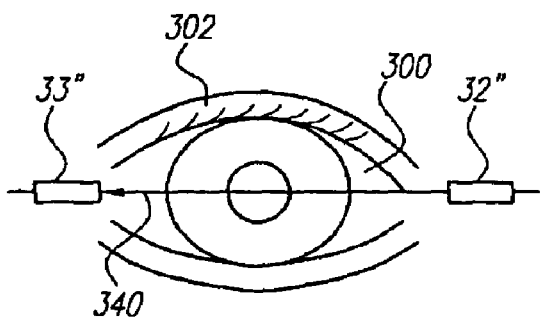
Figure 7C:
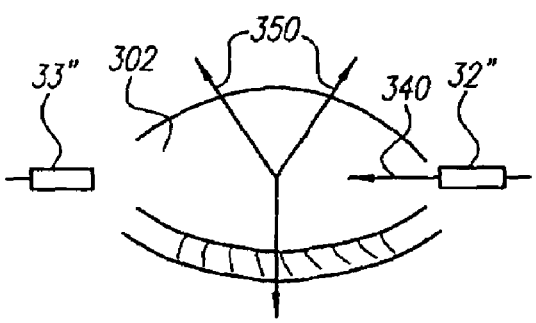

Alternatively, as shown in FIGS. 6B and 7B, the emitter 32' and sensor 33' may be mounted on the frame separately away from one another, e.g., such that the emitter 32' and sensor 33' are disposed substantially laterally with respect to each other. In a further alternative, shown in FIGS. 6C and 7C, the emitter 32" and sensor 33" may be mounted across the eye 300 in axial alignment with another. As the eyelid 302 closes, it may break the beam 340 being detected by the sensor 33".

In one embodiment, the emitter 32 and sensor 33 produce and detect continuous or pulsed light, respectively, e.g., within the infrared range to minimize distraction or interference with the wearer's normal vision. The emitter 32 may emit light in pulses at a predetermined frequency and the sensor 33 is configured to detect light pulses at the predetermined frequency. This pulsed operation may reduce energy consumption by the emitter 32 and/or may minimize interference with other light sources. Alternatively, other predetermined frequency ranges of light beyond or within the visible spectrum, such as ultraviolet light, or other forms of energy, such as radio waves, sonic waves, and the like, may be used.

Figure 3:
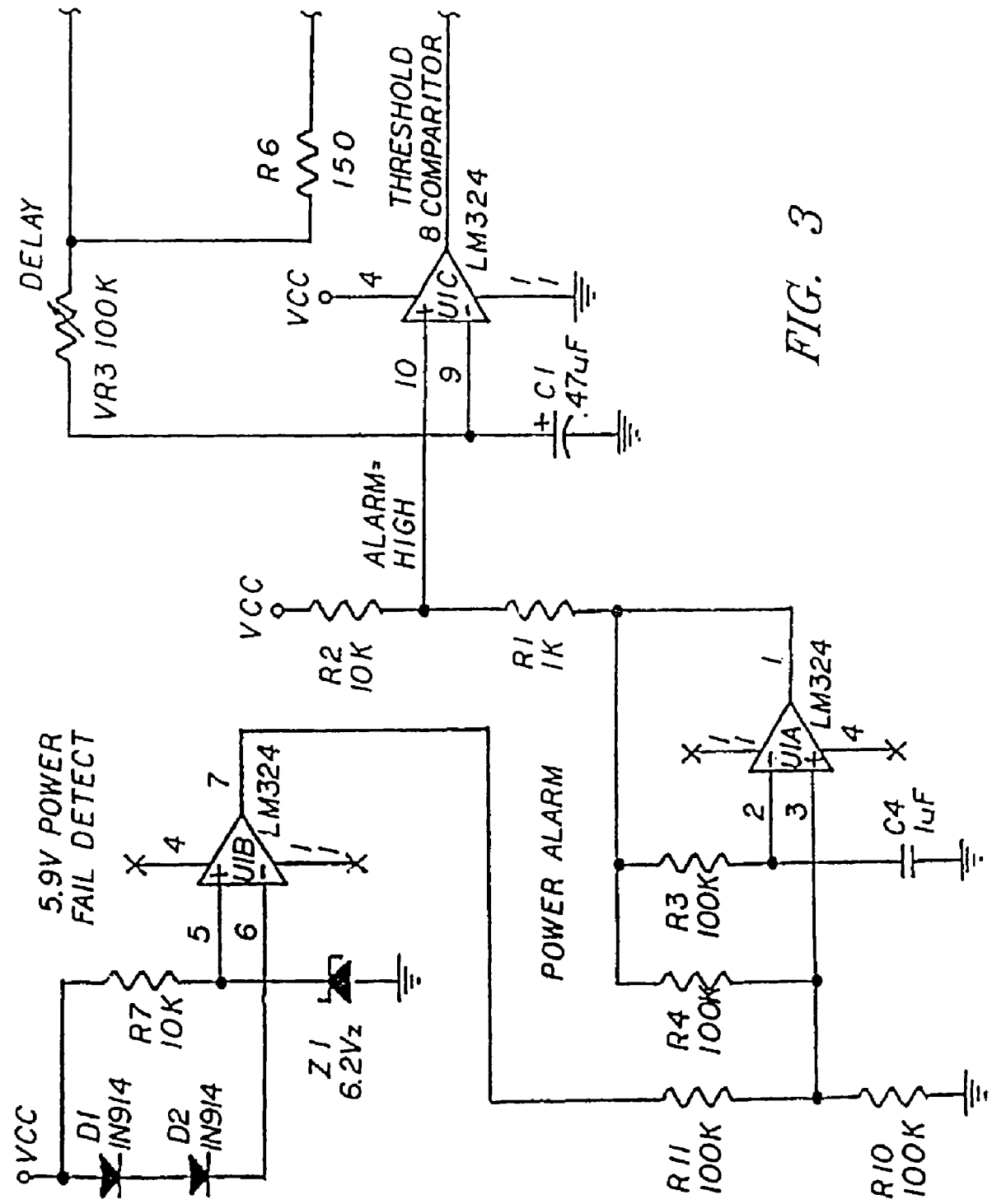
FIG. 3 is a schematic drawing of an exemplary embodiment of circuitry for transmitting an output signal corresponding to a sequence of eyelid movements.
Figure 3:
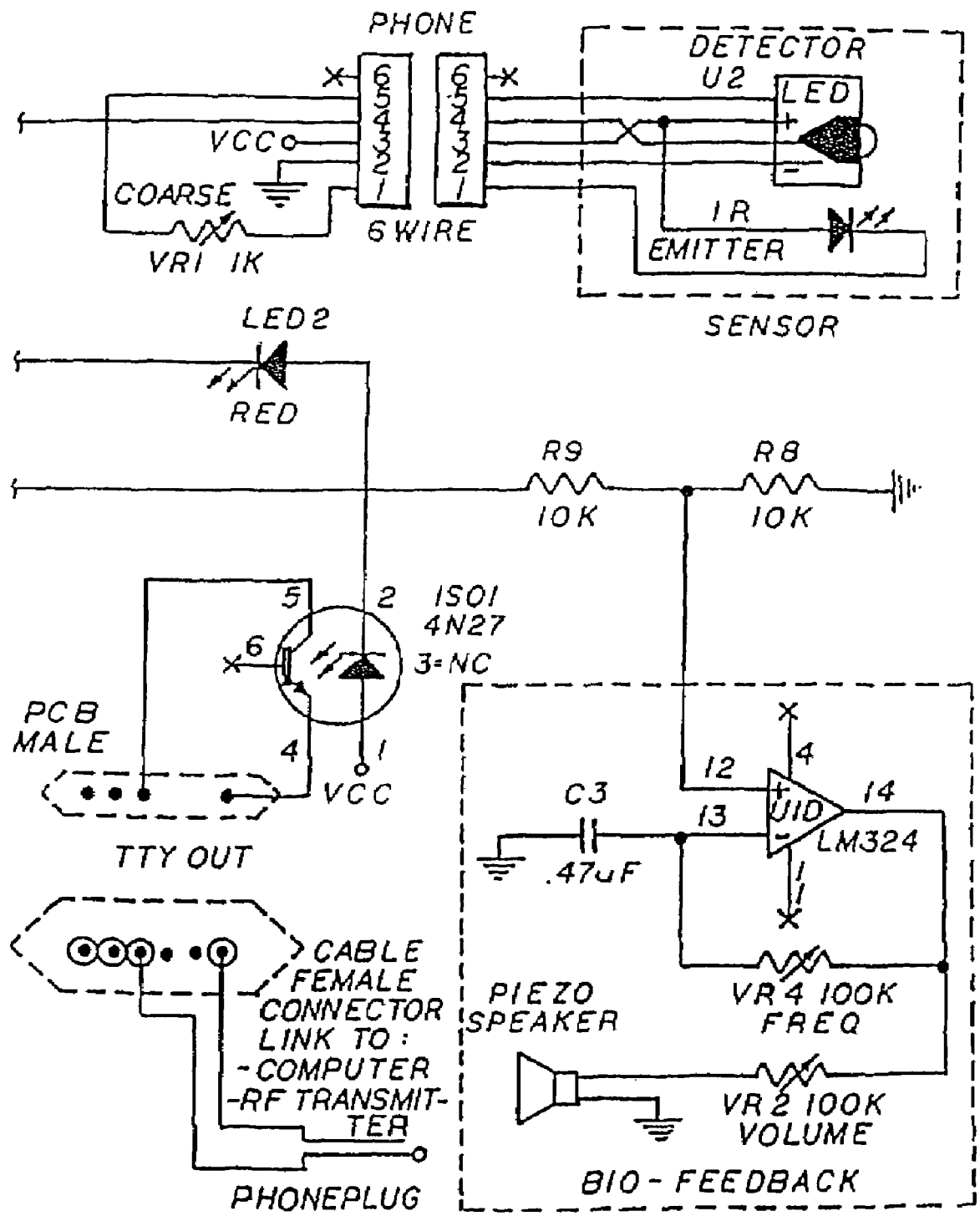
Figure 4:
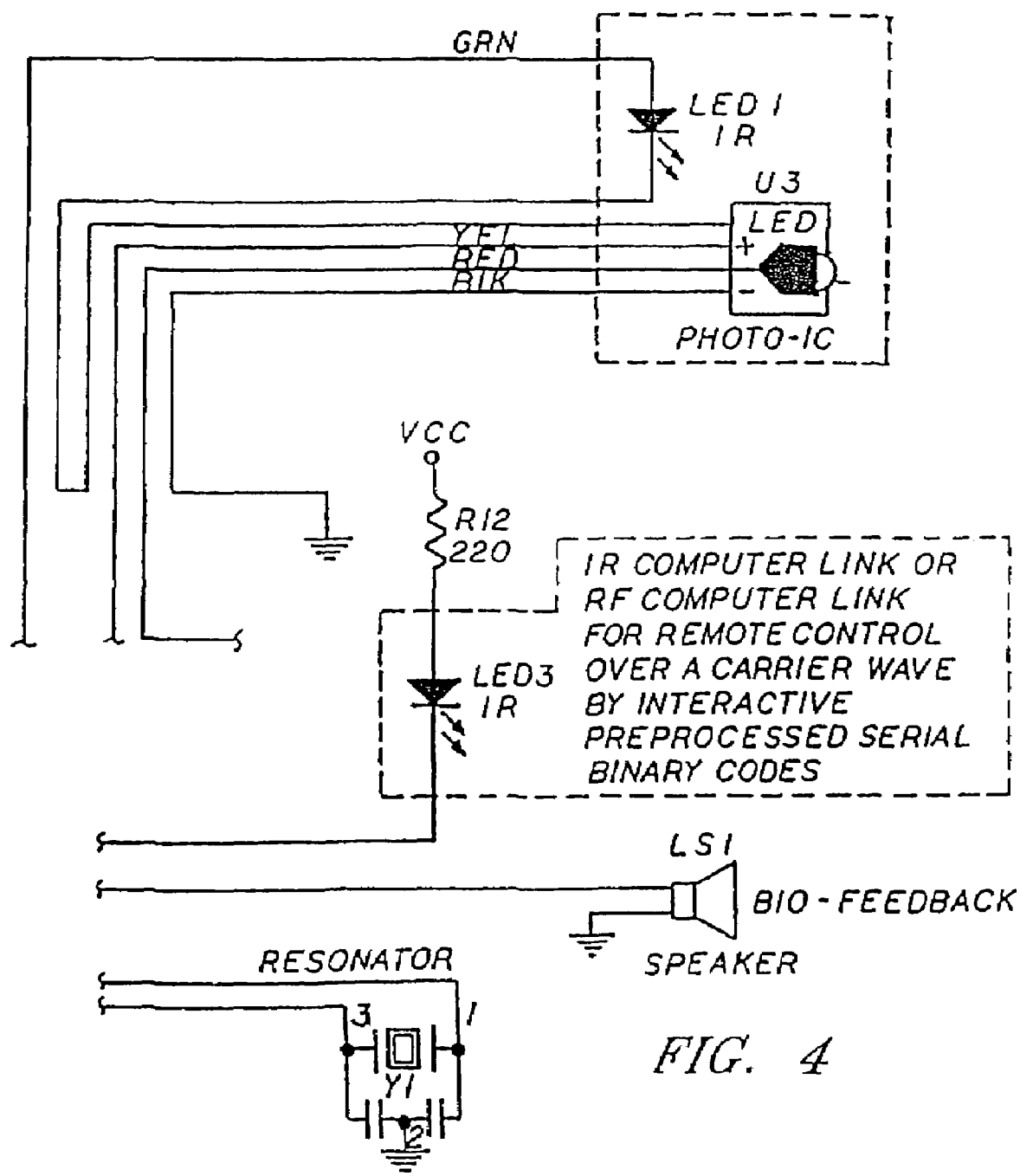
FIG. 4 is a schematic drawing of an exemplary embodiment of circuitry for controlling equipment in response to an output signal corresponding to a sequence of eyelid movements.
Figure 4:
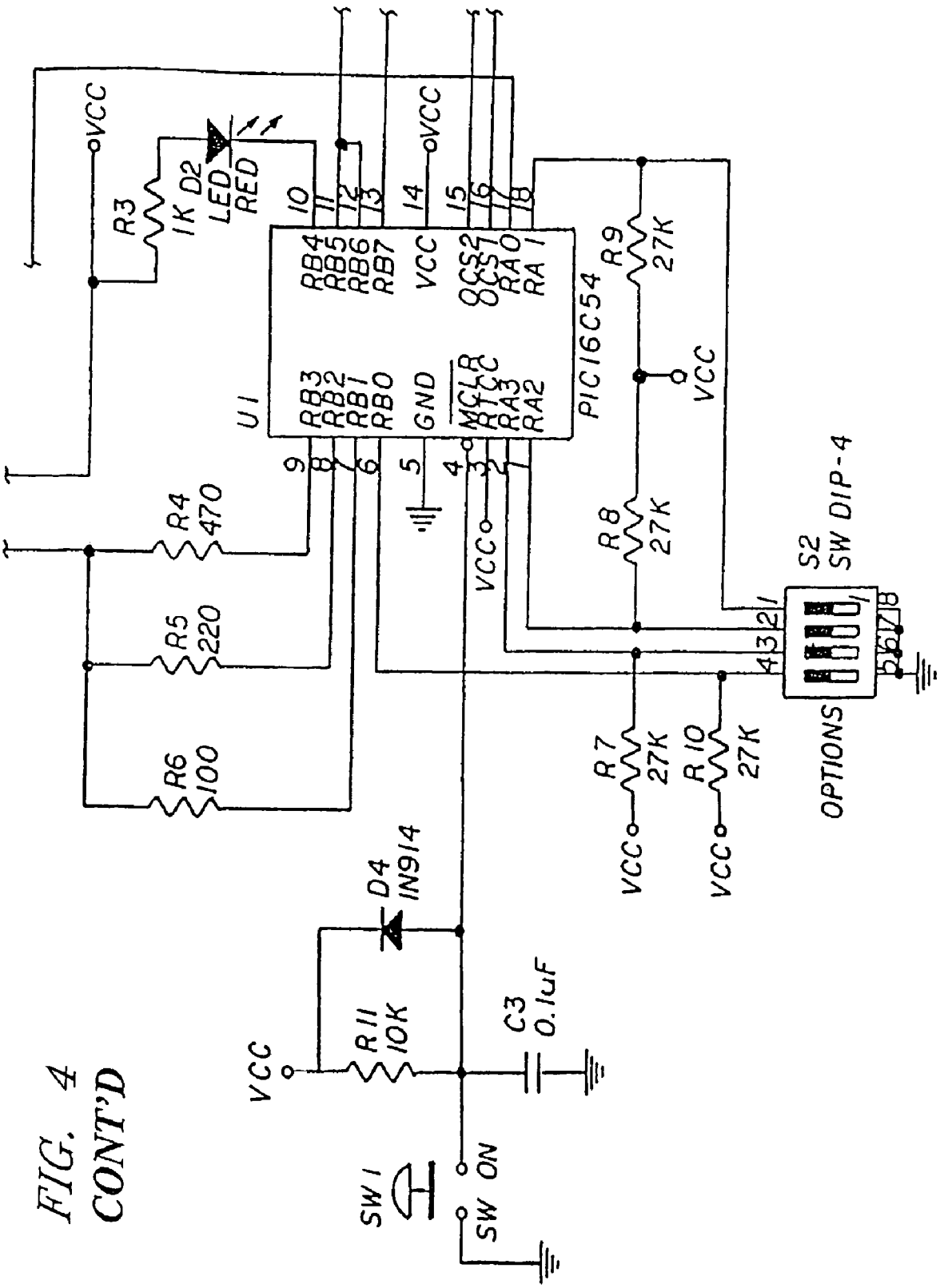
Figure 5:
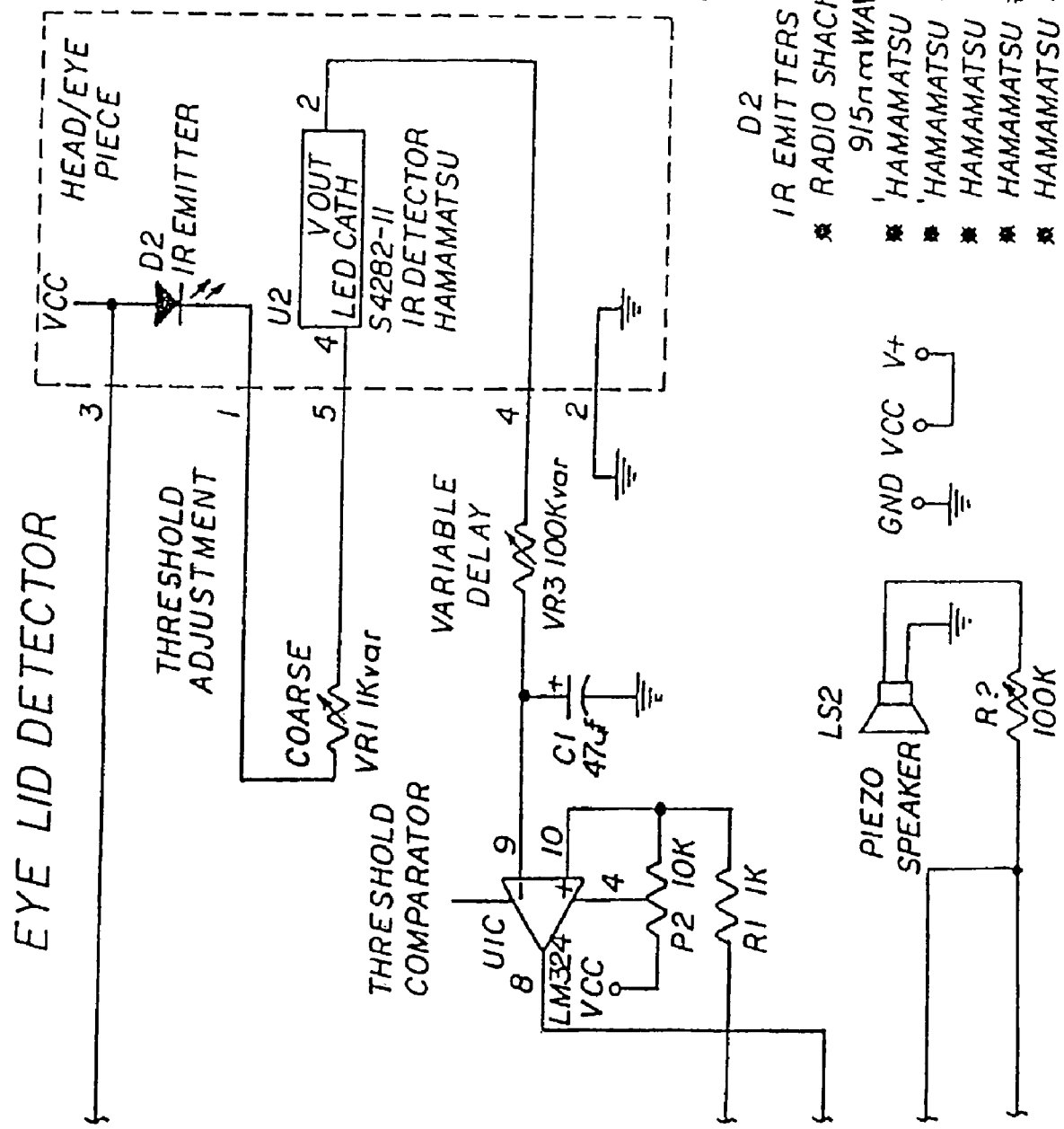
FIG. 5 is a schematic drawing of an exemplary embodiment of circuitry for detecting eyelid movement.
Figure 5:
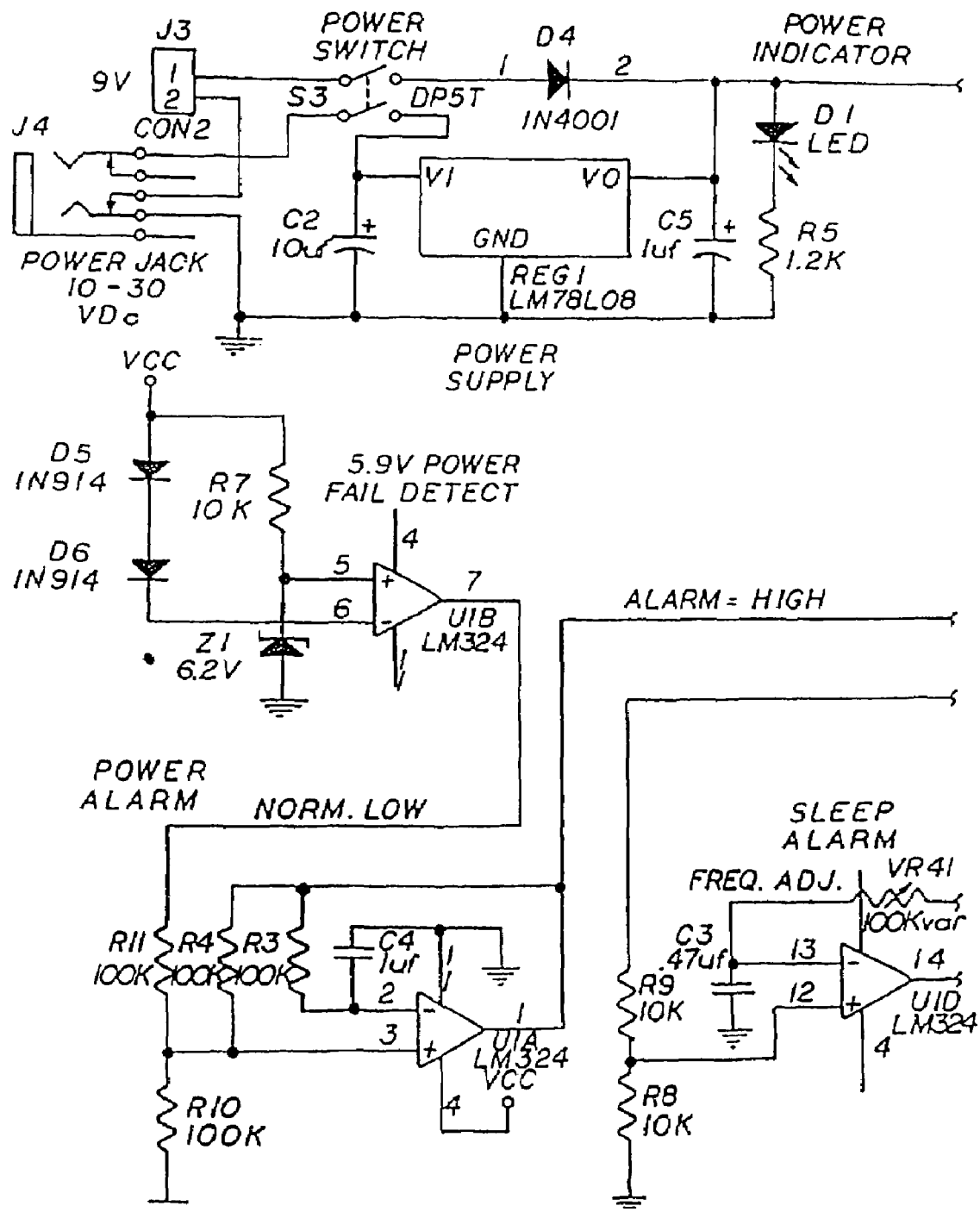
Figure 9:
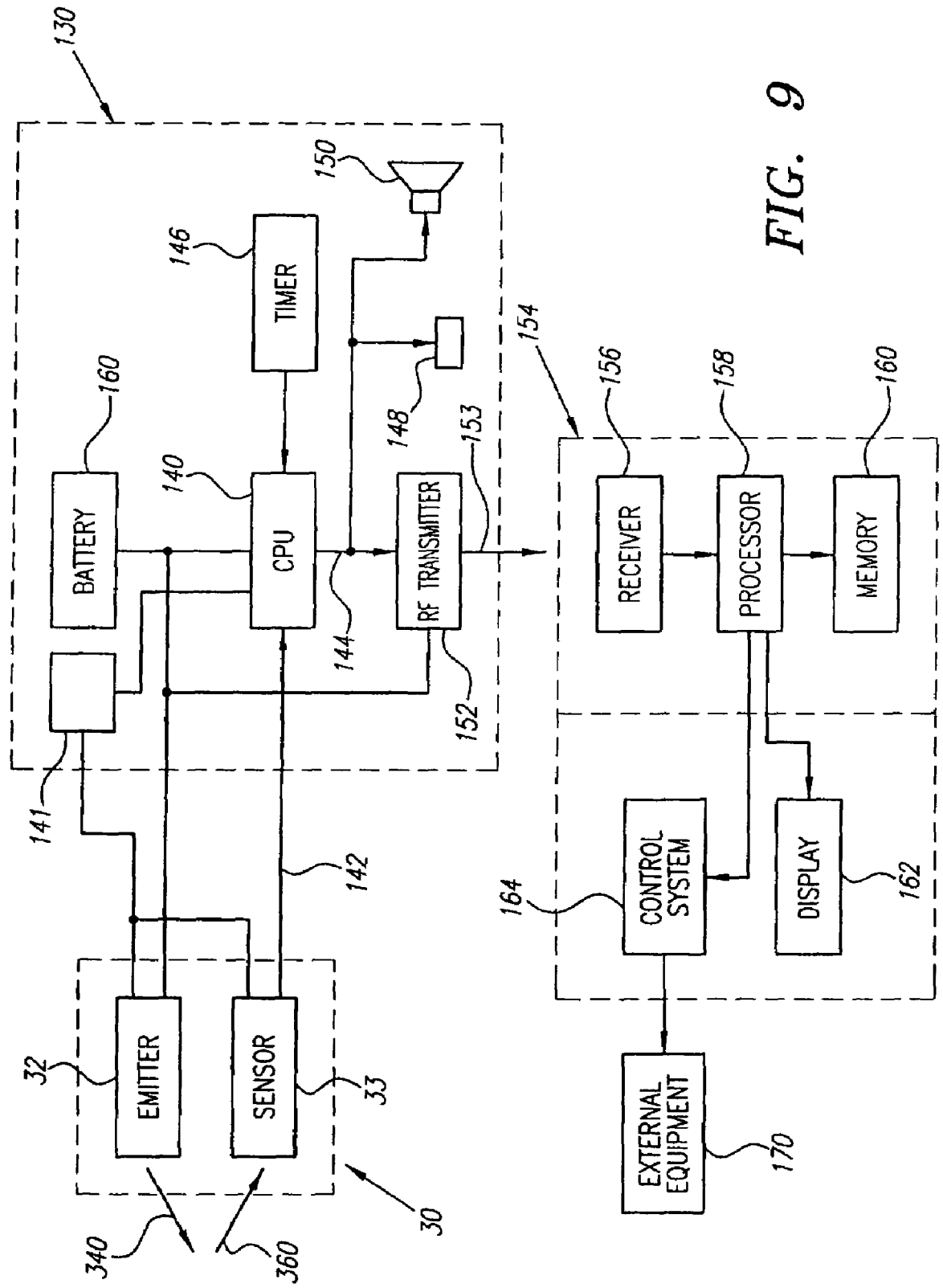
FIG. 9 is a block diagram of the components of yet another embodiment of a system for monitoring a user based upon movement of the user's eye and/or eyelid.

The processing box 130 is coupled to the detection device 30 by a cable 34 including one or more wires therein (not shown). As shown in FIG. 9, the processing box 130 may include a central processing unit (CPU) 140 and/or other circuitry, such as the exemplary circuitry shown in FIGS. 3-5, for receiving and/or processing an output signal 142, such as a light intensity signal, from the sensor 33. The processing box 130 may also include control circuitry 141 for controlling the emitter 32 and/or the sensor 33, or the CPU 140 may include internal control circuitry.

For example, in one embodiment, the control circuitry 141 may control the emitter 32 to produce a flickering infrared signal pulsed at a predetermined frequency, as high as thousands of pulses per second to as little as about 4-5 pulses per second, e.g., at least about 5-20 pulses per second, thereby facilitating detection of non-purposeful or purposeful eye-blinks as short as about 200 milliseconds per blink. The sensor 33 may be controlled to detect light pulses only at the predetermined frequency specific to the flicker frequency of the emitter 32. Thus, by synchronizing the emitter 32 and the sensor 33 to the predetermined frequency, the system 10 may be used under a variety of ambient conditions without the output signal 142 being substantially affected by, for example, bright sun light, total darkness, ambient infrared light backgrounds, or other emitters operating at different flicker frequencies. The flicker frequency may be adjusted to maximize the efficient measurement of the number of eye blinks per unit time (e.g. about ten to about twenty eye blinks per minute), the duration of each eye blink (e.g. about 200 milliseconds to about 300 milliseconds), and/or PERCLOS (i.e., the percentage of time that the eyelid is completely or partially closed), or to maximize efficiency of the system, while keeping power consumption to a minimum.

The control circuitry 141 and/or processing box 130 may include manual and/or software controls (not shown) for adjusting the frequency, focus, or intensity of the light emitted by the emitter 32, to turn the emitter 32 off and on, to adjust the threshold sensitivity of the sensor 33, and/or to allow for self-focusing with maximal infrared reflection off of a closed eyelid, as will be appreciated by those skilled in the art.

In addition, the processing box 130 also may include a power source 160 for providing power to the emitter 32, the sensor 33, the CPU 144, and/or other components in the processing box 130. The processor box 130 may be powered by a conventional DC battery, e.g., a nine volt battery or a rechargeable lithium, cadmium, or hydrogen-generated battery, and/or by solar cells attached to or built within the system 14. Alternatively, an adapter (not shown) may be connected to the processor box 130, such as a conventional AC adapter or a twelve volt automobile lighter adapter.

The CPU 140 may include timer circuitry 146 for comparing the length of individual elements of the output signal 142 to a predetermined threshold to distinguish between normal blinks and other eyelid movement. The timer circuitry 146 may be separate discrete components or may be provided internally within the CPU 140, as will be appreciated by those skilled in the art. The CPU 140 may convert the output signal 142 into a stream of data 144, which may be used to communicate to other persons or equipment. For example, the stream of data 144 produced by the CPU 140 may be a binary signal, such as Morse code or ASCI code. Alternatively, the CPU 140 may be capable of producing other outputs, e.g., synthesized voice signals, control signals for equipment, or pictorial representations.

To facilitate communication, the processing box 130 may include a variety of output devices for using the stream of data 144. For example, an internal speaker 150 may be provided, that may produce an alarm sound or a synthesized voice. An output port 148 may be provided to which a variety of equipment, such as the video display 50 shown in FIG. 1, may be directly coupled by hard-wire connections.

In addition or alternatively, the processing box 130 may include a transmitter 152 coupled to the CPU 144 for wireless communication of the stream of data 144 to a remote location. For example, as shown in FIG. 9, the system 14 may include a receiving and processing unit 154, such as a computer or other control or display system. The transmitter 152 may be a radio frequency ("RF") transmitter capable of producing a short range signal, for example, reaching as far as about one hundred feet or more, or alternatively about forty five feet to fifty feet, even through walls or obstacles. Alternatively, other transmitters, e.g., an infrared transmitter, may be provided.

The transmitter 152 may also be coupled to an amplifier (not shown) to allow the stream of data to be transmitted hundreds or thousands of feet or more, e.g., using Bluetooth or other RF protocols. For example, the amplifier and transmitter 152 may communicate via telephone communication lines, satellites and the like, to transmit the stream of data to a remote location miles away from the system, where the data can be monitored, analyzed in real time, or stored (e.g., as in a truck or aircraft "black box" recorder) for future or retrospective analysis. The system may include, or may be coupled to a global positioning system (GPS) for monitoring the location, movement, and/or state of cognitive alertness, wakefulness, sleepiness, or emotional/behavioral performance and/or safety of an individual wearing the detection device 30.

The receiving and processing unit 154 may include a receiver 156, e.g., a radio frequency receiver, for receiving signals 153, including the stream of data, transmitted by the transmitter 152. A processor 158 is coupled to the receiver 156 for translating, storing, and/or using the information in the stream of data, the processor 158 being coupled to memory circuitry 160, a communication device 162, and/or a control system 164. For example, the receiving and processing unit 154 may include the memory circuitry 160 therein into which the processor 158 may simply store the stream of data for subsequent retrieval and analysis.

The processor 158 may interpret the stream of data, for example, by converting a binary code in the stream of data into an understandable message, i.e., a series of letters, words and/or commands, and/or may use augmentative communication devices or software (such as KE:NX or Words Plus) to facilitate communication. The resulting message may be displayed on the communication device 162, which may include a video display for displaying text, pictures and/or symbols, a synthesized voice module for providing electronic speech, and the like.

Figure 12A:
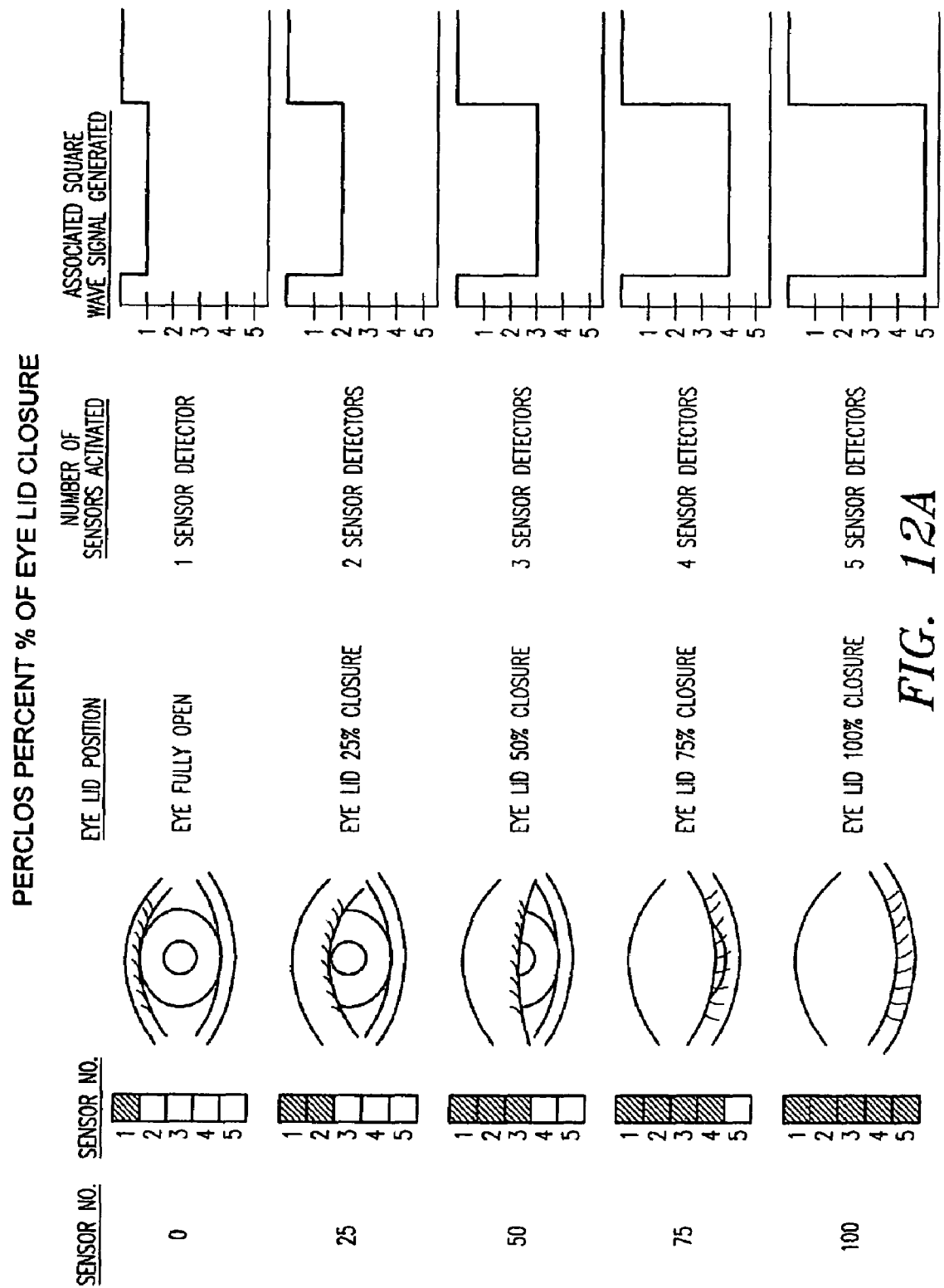
FIG. 12A is a table showing the relationship between the activation of an array of sensors, such as that shown in FIGS. 10A-10D and an eye being monitored by the array, as the eye progresses between open and closed conditions.

Alternatively, the stream of data may be displayed graphically on a computer video screen or other electronic display device as a "real time" message signal or numerically (e.g., displaying blink rate, blink duration, PERCLOS, etc.), or displayed graphically similar to an EKG or EEG tracing. In addition, as shown in FIG. 12C, the stream of data may be displayed along with other physiological data, such as skin conductance, body temperature, cardiovascular data (e.g. heart rate, blood pressure), respiratory data (e.g. respiration rate, blood oxygen and carbon dioxide levels), electromyographic (EMG) and/or actigraphic data (i.e. body movement, position), and/or other sleep polysomnographic (PSG) or electroencephalographic (EEG) variables. Alternatively, the stream of data may be integrated with controllers that monitor automobile or mechanical functions (e.g. vehicle speed, acceleration, braking functions, torque, sway or tilt, engine or motor speed, etc.) to make intelligent decisions regarding slowing down or speeding up the vehicle depending upon road and/or vehicle conditions, as well as functions relating to the state of consciousness, wakefulness, attentiveness, and/or real time performance vigilance responses of the driver or machine operator.

In addition, the message may be interpreted by the processor 158 for directing the control system 164 to control one or more pieces of machinery or equipment. For example, the stream of data may include a command to direct the control system 164 to control relay switches or other devices to turn off and on an electrical device, such as an appliance, electrical wheelchair, engine, light, alarm, telephone, television, computer, a tactile vibrating seat, and the like, or to operate an eye-activated computer mouse or other controller.

Alternatively, the processor 158 may use the stream of data to control PC, IBM, Macintosh, and other computers, and/or compatible computer software and/or hardware, e.g., to interact with a computer similar to a mouse, a "return" key, and/or a "joystick." For example, the stream of data may include commands to activate a series of menus from which submenus or individual items may be selected, as are used in commercially available general use software and computer games, as well as special communications software, such as WORDS-PLUS or Ke:NX. The processor 158 may then control, scroll, or select items from computer software programs, operate a printer, or other peripheral device (e.g., selecting a font, paragraph, tab or other symbol operator, selecting commands, such as "edit," "find," "format," "insert," "help," or controlling CD-ROM or disc drive operations, and/or other Windows and non-Windows functions).

Alternatively, the receiver 156 may be coupled directly to a variety of devices (not shown), such as radio or television controls, lamps, fans, heaters, motors, vibro-tactile seats, remote control vehicles, vehicle monitoring or controlling devices, computers, printers, telephones, lifeline units, electronic toys, or augmentative communication systems, to provide a direct interface between the user and the devices.

During use, the detection device 30 may be placed on a user's head, i.e., by putting the eyeglasses 20 on as shown in FIG. 1. The adjustable arm 31 and/or the clamp 27 may be adjusted to optimally orient the emitter 32 and sensor 33 towards the user's eye 300 (shown in FIGS. 6A-6C and 7A-7C). The emitter 32 may be activated and a beam of light 340 directed from the emitter 32 towards the eye 300. The intensity and/or frequency of the emitter 32 and/or the threshold sensitivity of the sensor 33 or other focus may then be adjusted (e.g. manually or automatically using self-adjusting features).

Because of the difference in the reflective characteristics of the surface of the eye 300 itself and the eyelid 302, the intensity of the light reflected off of the eye 300 depends upon whether the eye 300 is open or closed. For example, FIGS. 6A and 6B illustrate an open eye condition, in which a ray of light 340 produced by the emitter 32 strikes the surface of the eye 300 itself and consequently is scattered, as shown by the rays 350. Thus, the resulting light intensity detected by the sensor 33 is relatively low, i.e., the sensor 33 may not receive any substantial return signal.

In FIGS. 7A and 7B, the eye 300 is shown with the eyelid 302 closed as may occur during normal blinks, moments of drowsiness, intentional blinks, or other eyelid movement. Because the light 340 strikes the eyelid 302, it is substantially reflected back to the sensor 33, as shown by the ray 360, resulting in a relatively high light intensity being detected by the sensor 33. Alternatively, as shown in 7C, the beam of light 340 may be broken or cut by the eyelid 302 when the eye 300 is closed.

The sensor 33 consequently produces a light intensity signal that indicates when the eye 300 is open or closed, i.e., corresponding to the time during which reflected light is not detected or detected, respectively, by the sensor 33. Generally, the intensity of the infrared light reflected from the surface of the eyelid is not substantially affected by skin pigmentation. If it is desired to adjust the intensity of light reflected from the eyelid, foil, glitter, reflective moisturizer creams and the like may be applied to increase reflectivity, or black eye liner, absorptive or deflective creams and the like may be applied to reduce reflectivity.

Figure 12B:
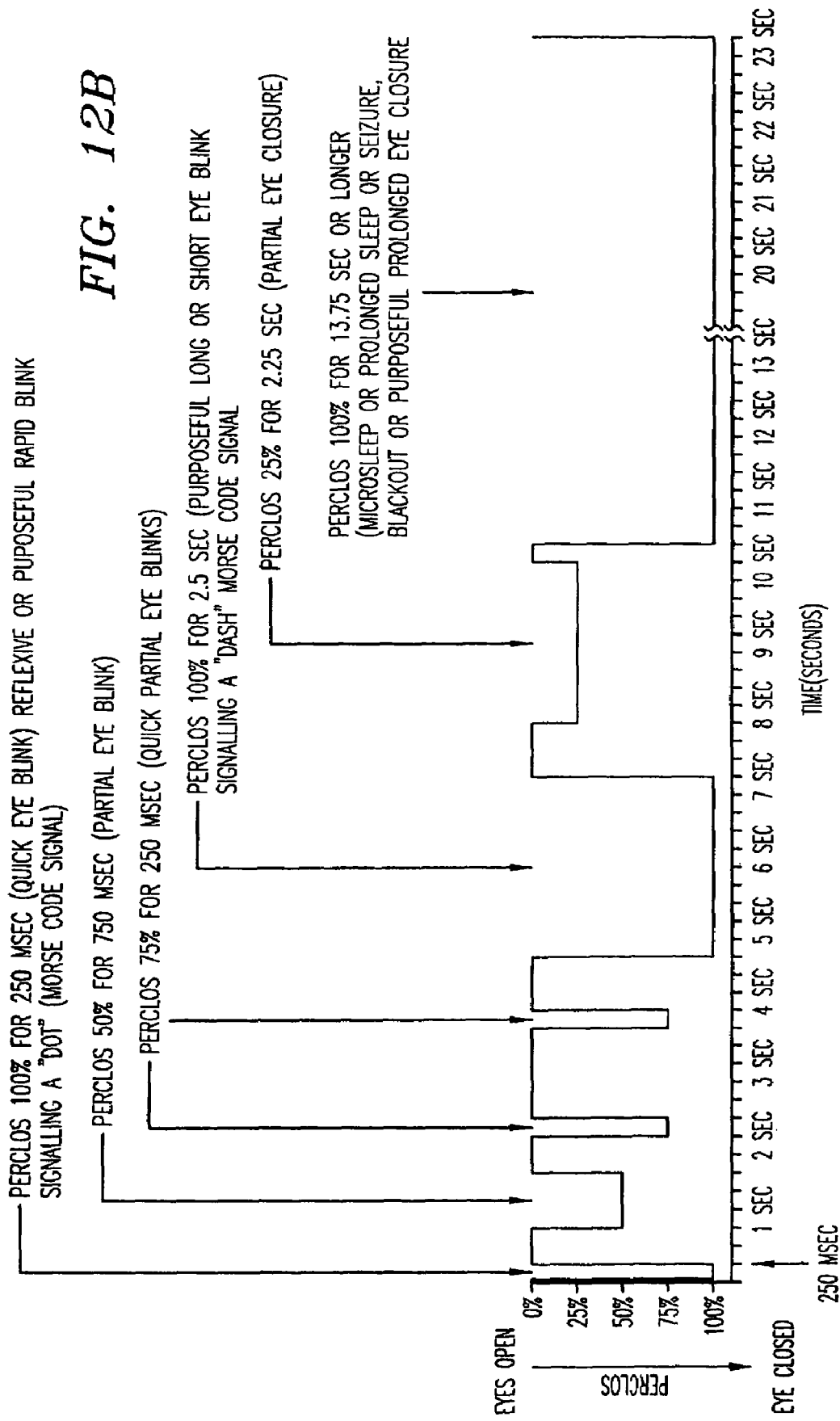
FIG. 12B is a graph showing a stream of data provided by an array of sensors, such as that shown in FIGS. 10A-10D, indicating the percentage of eye coverage as a function of time ("PERCLOS").
Figure 12C:
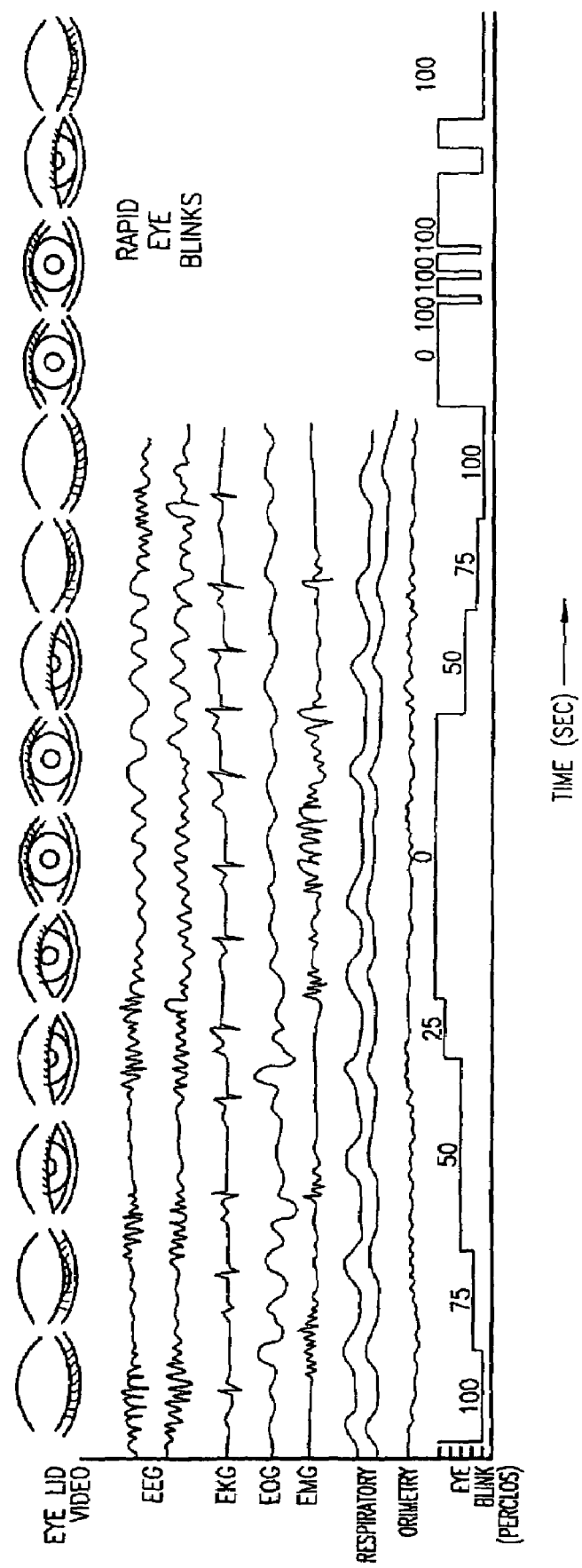
FIG. 12C is a graphical display of a number of physiological parameters, including PERCLOS, of a person being monitored by a system including a device such as that shown in FIGS. 10A-10D.

Returning to FIG. 9, the light intensity detected by the sensor 33 results in an output signal 142 including a series of time-dependent light intensity signals (as shown, for example, in FIG. 12B). The output signal 142 is received by the CPU 140 coupled to the sensor 33, which compares the length of time of each light intensity signal 142, for example, corresponding to a closed eye condition, with a predetermined threshold. The timer circuitry 146 may provide a threshold time to the CPU 140 for distinguishing normal blinks from intentional and/or other unintentional eyelid movement, which the CPU 140 may then filter out of the output signal 142. The CPU 140 then produces a stream of data 144 that may be used for voluntary and/or involuntary communication.

In one useful application, the detection device 30 may be used to detect impending drowsiness or "micro-sleeps" (i.e., sleep intrusions into wakefulness lasting a few seconds) of a user, with the processing box 130 triggering a warning to alert the user, others in his or her presence, or monitoring equipment of the onset of drowsiness. The threshold of the timer circuitry 146 may be adjusted such that the CPU 140 detects relatively long periods of eye closure, as may occur when a person is falling asleep.

For example, because normal blinks are relatively short, the threshold may be set at a time ranging from close to zero seconds up to several seconds, e.g., between about two and three hundred milliseconds (200-300 ms), or, in another embodiment, about two hundred fifty milliseconds (250 ms), e.g., to distinguish normal blinks from drowsiness-induced eyelid movement. When the CPU 140 detects a drowsiness condition, i.e., detects a high light intensity signal exceeding the predetermined threshold time, it may activate a warning device. The warning device may be included within the processing box 130, such as the speaker 150, or alternatively on the frame, for example, by mounting a warning light (not shown) or an alarm speaker (not shown in FIG. 9, see FIG. 10C) on the frame. In another alternative, the warning device may be a tactile device, e.g., a vibrating seat, and the like, as described elsewhere herein.

Alternatively, the detection device 30 may be used to unobtrusively record or monitor drowsiness-induced eyelid movement, with the CPU 140 producing a stream of data 144 that the transmitter 152 may transmit to the receiving and processing unit 154 (FIG. 9). For example, the device 30 may be used in conjunction with a vehicle safety system to monitor a driver's level of awareness or attentiveness. The stream of data 144 may be transmitted to a receiving and processing unit 154 mounted in a vehicle, which may store data on the driver's drowsiness and/or may use the data to make decisions by predetermined algorithmic responses to control the vehicle, e.g., adjust the vehicle's speed or even turn the vehicle's engine off. Thus, the detection device 30 may be used to monitor truck drivers, taxi drivers, ship or airline pilots, train conductors or engineers, radar or airport control tower operators, operators of heavy equipment or factory machinery, scuba divers, students, astronauts, entertainment participants or observers, and the like.

The detection device 30 and system 14 may also be used in a medical diagnostic, therapeutic, research, or professional setting to monitor the wakefulness, sleep patterns, and/or sympathetic and parasympathetic effects of stressful conditions or alerting drugs (e.g. caffeine, nicotine, dextro-amphetamine, methylphenidate, modafanil), sedating drugs (e.g. benzodiazapines, Ambien), or circadian rhythm altering effects of light and darkness or melatonin, which may affect blink rate, blink velocity, blink duration, or PERCLOS of a patient or vehicle operator. The signals may be stored and analyzed in real time for trend changes measured over time to predict drowsiness effects of individuals using device.

Similar to the method just described, the CPU 140 may produce a stream of data 144, which the transmitter may send to a remote receiving and processing unit 154. The receiving and processing unit 154 may store the stream of data 144 in the memory circuitry 160 for later retrieval and analysis by researchers, medical professionals, or safety personnel (e.g., similar to the way in which flight recorder data may be stored in an aircraft's "black box" recorder). The receiving and processing unit 154 may also display the stream of data 144, for example at a nurse's station, as an additional parameter to continually monitor a patient's physical, mental, or emotional condition. The unit 154 may store and/or produce a signal, e.g., by a series of algorithms, that must be responded to within a predetermined time (e.g., performance vigilance monitoring) to prevent false positives and negatives.

A number of medical conditions may be monitored by the detection device 30 and system 14, such as petit mal epilepsy, in which the eyes flutter at a rate of about three cycles per second, grand mal or psychometer seizures, where the eyes may stare or close repetitively in a jerky manner, myoclonic seizures, in which the lids may open and close in a jerky manner, or tics, or other eye movements, such as encountered by people with Tourette's syndrome. The system may be used to monitor g-LOC (loss of consciousness) of pilots caused by positive or negative g-force effects, hypoxemia of passengers or crew in aircraft due to losses in cabin pressure, nitrogen narcosis or "the bends" in divers, or the effects of gases, chemicals, drugs, and/or biological agents on military personnel or other individuals.

The system may also be used to monitor psychological situations, for example, to detect stress or when a person lies (e.g., by closing or otherwise moving their eyes when lying), during hypnosis, to monitor attentiveness, to measure one or more of: the "negative" side effects and/or "positive" therapeutic effects of drugs or pharmaceuticals on conditions where ocular functions are compromised (e.g. L-dopa in improving blink rates in Parkinson's disease; drugs used to treat ocular tics or neuromuscular disorders such as ALS or myasthenia gravis); drug or alcohol levels based on correlative ocular measures (e.g. nystagmus or delayed pupil responses to light flashes); the therapeutic and side effects of anti-convulsants, drugs, alcohol, toxins, or the effects of hypoxia or ventilation, and the like. Neurological conditions in patients of all ages may also be monitored where the innervation or mechanical function of the eye or eyelid may be affected, such as in Parkinson's disease, muscle diseases, e.g., myotonia, myotonic muscular dystrophy, blepharospasm, photophobia or light sensitivity, encephalopathy, seizures, Bell's palsy, or where the condition may produce loss of vision (e.g. macular degeneration), eyelid drooping or ptosis, such as third cranial nerve palsy or paresis, brainstem lesions or stroke, tumors, infection, metabolic diseases, trauma, degenerative conditions, e.g., multiple sclerosis, amyotrophic lateral sclerosis, polyneuropathy, myesthenia gravis, botulism, tetanus, tetany, tardive dyskinesia, brainstem encephalitis, and other primary eyelid conditions, such as exopthalmos, thyrotoxicosis or other thyroid conditions. In a similar manner, the detection device 30 may be used in an ambulatory fashion to study the progression and/or regression of any of the above neuro-opthalmological and opthalmological disturbances.

Similarly, the detector device 30 may be used in biofeedback applications, for example, in biofeedback, hypnosis or psychological therapies of certain conditions (e.g. tic disorders). The detector device 30 may produce a stimulus, e.g. activating a light or speaker, and monitor the user's eyelid movement in anticipation of receiving a response, e.g., a specific sequence of blinks, acknowledging the stimulus within a predetermined time. If the user fails to respond, the processor may store the response, e.g. including response time, and/or may automatically transmit a signal, such as an alarm signal.

In addition, the detection device 30 may be used to monitor individuals in non-medical settings, such as during normal activity in a user's home or elsewhere. For example, individuals with involuntary medical conditions, such as epilepsy or narcolepsy, may be monitored, or other individuals, such as, infants and children, prison inmates, demented patients (e.g., with Alzheimer's disease), law enforcement personnel, military personnel, bank tellers, cashiers, casino workers, students, swing or graveyard shift workers, and the like, may be monitored. Similar applications may be applied in a sleep laboratory during polysomnographic procedures (e.g. PSG, MSLT or MWT) for monitoring sleep patients to measure parameters, such as onset of sleep, sleep latency, time of eyelid closing or opening, time of awakening during the night, etc., or to animal research where eye blinking, pupil changes, and/or slow or rapid eye movement may be a factor to be studied, or to the ocular neuro-developmental functions of infants.

The detection device 30 may be used to study or monitor the drowsiness, awakening, or alerting effects of prescribed pharmaceuticals (e.g. stimulants), alcohol or other illicit drugs, toxins, poisons, as well as other relaxing, sedating or alerting techniques or devices. Similarly, the performance and vigilance abilities of the user may be tested and analyzed as a direct function of, or in relationship to, PERCLOS.

When the CPU 140 detects the presence of particular eyelid movement, such as an extensive period of eye closure, which may occur, for example, during an epileptic seizure, a syncopal episode, a narcoleptic episode, or when dozing off while driving or working, the CPU 140 may produce an output signal which activates an alarm. Alternatively, the transmitter 152 may send an output signal to shut off equipment being used, to notify medical personnel, such as by automatically activating a telephone to dial emergency services, to signal remote sites, such as police stations, ambulances, vehicle control centers, guardians, and the like.

The system 14 may also find useful application for voluntary communication. A user wearing the detection device 30 may intentionally blink in a predetermined pattern, for example, in Morse code or other blinked code, to communicate an understandable message to people or equipment (e.g., to announce an emergency). The CPU 140 may convert a light intensity signal 142 received from the sensor 33 and corresponding to the blinked code into a stream of data 144, or possibly directly into an understandable message including letters, words and/or commands.

The stream of data 144 may then be displayed on a video display 50 (see FIG. 1) coupled to the output port 148, or emitted as synthesized speech on the internal speaker 150. The stream of data 144 may be transmitted by the transmitter 152 via the signal 153 to the receiving and processing unit 154 for displaying messages, or for controlling equipment, such as household devices, connected to the control system 164. In addition to residential settings, the system 14 may be used by individuals in hospitalized or nursing care, for example by intubated, ventilated, restrained, paralyzed or weakened patients, to communicate to attending medical staff and/or to consciously signal a nurse's station. These include all patients who have no physical ability to communicate verbally, but who retain ability to communicate using eye blinking of one or both eyes (e.g., patients with amyotrophic lateral sclerosis, transverse myelitis, locked-in syndrome, cerebravascular strokes, terminal muscular dystrophy and those intubated on ventilation).

The device may be used in any environment or domain, e.g., through water or other substantially transparent fluids. Further, the device 30 may also be used as an emergency notification and/or discrete security tool. A person who may be capable of normal speech may wear the device 30 in the event of circumstances under which normal communication, i.e., speech, is not a viable option. For example, a bank or retail employee who is being robbed or is otherwise present during the commission of a crime may be able to discretely blink out a preprogrammed warning to notify security or to call law enforcement. Alternatively, a person with certain medical conditions may wear the device in the event that they are physically incapacitated, i.e., are unable to move to call for emergency medical care, but are still able to voluntarily move their eyes. In such cases, a pre-recorded message or identifying data (e.g. name of the user, their location, the nature of the emergency, etc.) may be transmitted to a remote location by a specific set of eyeblink codes or preprogrammed message. In this manner, the detection device 30 may be used to monitor patients in an ICU setting, patients on ventilators, prisoners, elderly or disabled persons, heavy equipment operators, truck drivers, motorists, ship and aircraft pilots, train engineers, radar or airport control tower operators, or as a nonverbal or subliminal tool for communication by military guards, police bank tellers, cashiers, taxi-drivers, and the like. The detection device 30 may also be used as a recreational device, for example, as a children's toy similar to a walkie-talkie or to operate a remote control toy vehicle.

In addition, it may be desirable to have the CPU 140 perform an additional threshold comparison to ensure continued use of the detection device 30. For example, additional timer circuitry may be coupled to the CPU 140 such that the CPU 140 may compare the light intensity signals received from the sensor 33 to a second predetermined threshold provided by the timer circuitry. The second predetermined threshold may correspond to a time period during which a person would normally blink. If the CPU 140 fails to detect a normal blink within this time period or if the user fails to respond to a predetermined stimulus (e.g. a blinking light or sound), the CPU 140 may produce a signal, activating the speaker 150 or transmitting a warning using the transmitter 152.

This may be useful, if, for example, the detection device 30 is removed by a perpetrator during commission of a crime, falls off because of the onset of a medical episode, as well as to prevent "false alarms," or to measure the "state of attentiveness" of the user. Alternatively, performance vigilance tasks may be required of the user to determine whether the signal transmitted is a purposeful or "false alarm" signal, and also for measuring attention or drowsiness levels for purposes of biofeedback, and also to measure compliance of the user wearing the device.

Alternatively, the polarity of the output signal 142 may be reversed such that a stream of data is produced only when the eye is opened, for example, when monitoring patients in a sleep lab to measure onset of sleep, sleep latency, time of eyelid closure, etc., or to monitor sleeping prison inmates. For such uses, the CPU 140 may activate an alarm only when an open eye condition is detected, as will be appreciated by those skilled in the art.

Turning to FIG. 8, another embodiment of the detection device 30 is shown. In this embodiment, the emitter and sensor are a single solid state light emission and detecting biosensor device 132, which are mounted directly onto the eyeglasses 20. The biosensor device 132, which may produce and detect infrared light, may be as small as two millimeters by four millimeters (2 mm×4 mm) and weigh only a few grams, thereby enhancing the convenience, comfort and/or discretion of the detection device 30. Because of the small size, the biosensor device 133 may be mounted directly in the lens 21, as shown in FIG. 8, on an outside or inside surface of the lens 21, in the bridgework 24 or at another location on the frame 22 that may facilitate detection of eye movement. The biosensor device 132 may measure less than about five millimeters by five millimeters surface area, and may weigh as little as about one ounce, thereby providing a emitter/sensor combination that may be unobtrusive to vision, portable, and may be conveniently incorporated into a light weight eye frame. Because the entire system may be self-contained on the frame, it moves with the user no matter which direction he or she looks and may operate in a variety of environments or domains, day or night, underwater, etc.

Hamamatsu manufactures a variety of infrared emitter and detector devices that may be used for the biosensor device 132, such as Model Nos. L1909, L1915-01, L2791-02, L2792-02, L2959, and 5482-11, or alternatively, a Radio Shack infrared emitter, Model No. 274-142, may be used. Multiple element arrays, e.g., linear optical scanning sensor arrays, appropriate for use may be available from Texas Advanced Optoelectronic Solutions, Inc. (TAOS) of Plano, Tex., such as Model Nos. TSL 201 (64 pixels×1 pixel), TSL 202 (128×1), TSL 208 (512×1), TSL 2301 (102×1). These sensors may be used in combination with lens arrays to facilitate focusing of the detected light, such as the Selfoc lens array for line scanning applications made by NSG America, Inc. of Irvine, Calif.

In addition, multiple biosensor devices 132 may be provided on the eyeglasses 20, for example, a pair of biosensor devices 132 may be provided, as shown in FIG. 8, for detecting eyelid movement of each eye of the user (not shown). A cable 134 may extend from each biosensor device 132 to a processing box 130, similar to the processing box 130 described above. The CPU 140 of the processing box 130 (not shown in FIG. 8) may receive and compare the output signal from each biosensor device 132 to further augment distinguishing normal blinks from other eyelid movement.

The pair of biosensor devices 132 may allow use of more sophisticated codes by the user, e.g., blinking each eye individually or together, for communicating more effectively or conveniently, as will be appreciated by those skilled in the art. In one form, a blink of one eye could correspond to a "dot," and the other eye to a "dash" to facilitate use of Morse code. The output signals from each eye could then be interpreted by the CPU 140 and converted into an understandable message.

In another form, a right eye blink (or series of blinks) may cause an electric wheelchair to move to the right, a left eye blink (or series of blinks) may move to the left, two simultaneous right and left eye blinks may cause the wheelchair to move forward, and/or four simultaneous right and left eye blinks may cause the wheelchair to move backward. Similar combinations or sequences of eye blinks may be used to control the on/off function, or volume or channel control of a television, AM/FM radio, VCR, tape recorder or other electronic or electromechanical device, any augmentative communications or controlling device, or any device operable by simple "on/off" switches (e.g., wireless television remote controls single switch television control units, universal remote controllers, single switch multi-appliance units with AC plug/wall outlet or wall switch modules, computer input adapters, lighted signaling buzzer or vibrating signal boxes, switch modules of all types, video game entertainment controller switch modules and switch-controlled electronic toys).

In additional alternatives, one or more lenses or filters may be provided for controlling the light emitted and/or detected by the biosensor device, an individual emitter, and/or detector. For example, the angle of the light emitted may be changed with a prism or other lens, or the light may be columnated or focused through a slit to create a predetermined shaped beam of light directed at the eye or to receive the reflected light by the sensor. An array of lenses may be provided that are adjustable to control the shape, e.g. the width, etc., of the beam of light emitted or to adjust the sensitivity of the sensor. The lenses may be encased along with the emitter in plastic and the like, or provided as a separate attachment, as will be appreciated by those skilled in the art.

Figure 10A:
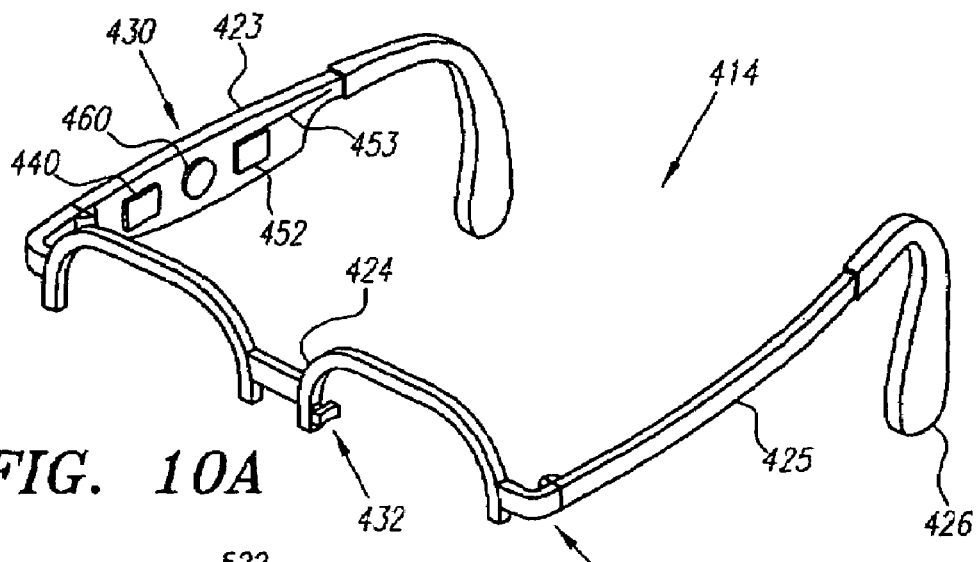
FIG. 10A is a perspective view of still another embodiment of a system for monitoring a user based upon movement of the user's eye and/or eyelid.

Turning to FIG. 10A, another embodiment of a system 414 is shown that includes a frame 422 including a biosensor device 432 with associated processor and transmitter circuitry 430 provided directly on the frame 422, for example, to enhance the convenience and discretion of the system 414. The frame 422 may include a bridge piece 424 onto which the biosensor device 432 may be fixedly, slidably, and/or adjustably mounted, and a pair of ear supports 423, 425.

One of the supports 423 may have a larger size compared to the other support 425, for example, to receive the processor and transmitter circuitry 430 embedded or otherwise mounted thereon. A processor 440, similar to the CPU 140 in the processing box 130 previously described, may be provided on the frame 422, and a power source, such as a lithium battery 460, may be inserted or affixed to the support 423. A radio frequency or other transmitter 452 (e.g., using Bluetooth or other protocols) is provided on the support 423, including an antenna 453, which may be embedded or otherwise fastened along the ear support 423, in the temple piece or elsewhere in the frame 422.

The system 414 may also include manual controls (not shown) on the ear support 423 or elsewhere on the frame 422, for example to turn the power off and on, or to adjust the intensity and/or threshold of the biosensor device 432. Thus, the system 414 may be substantially self-contained on the frame 422, which may or may not include lenses (not shown) similar to eyeglasses. External cables or wires may be eliminated, thereby providing a more convenient and comfortable system for communication and/or monitoring a user.

Figure 10B:
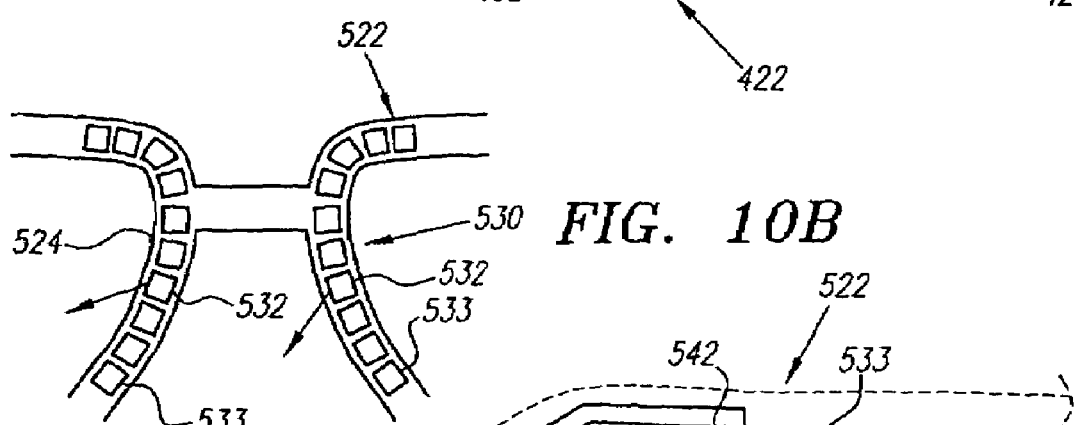
FIG. 10B is a schematic detail of a portion of the system of FIG. 10A.
Figure 10C:
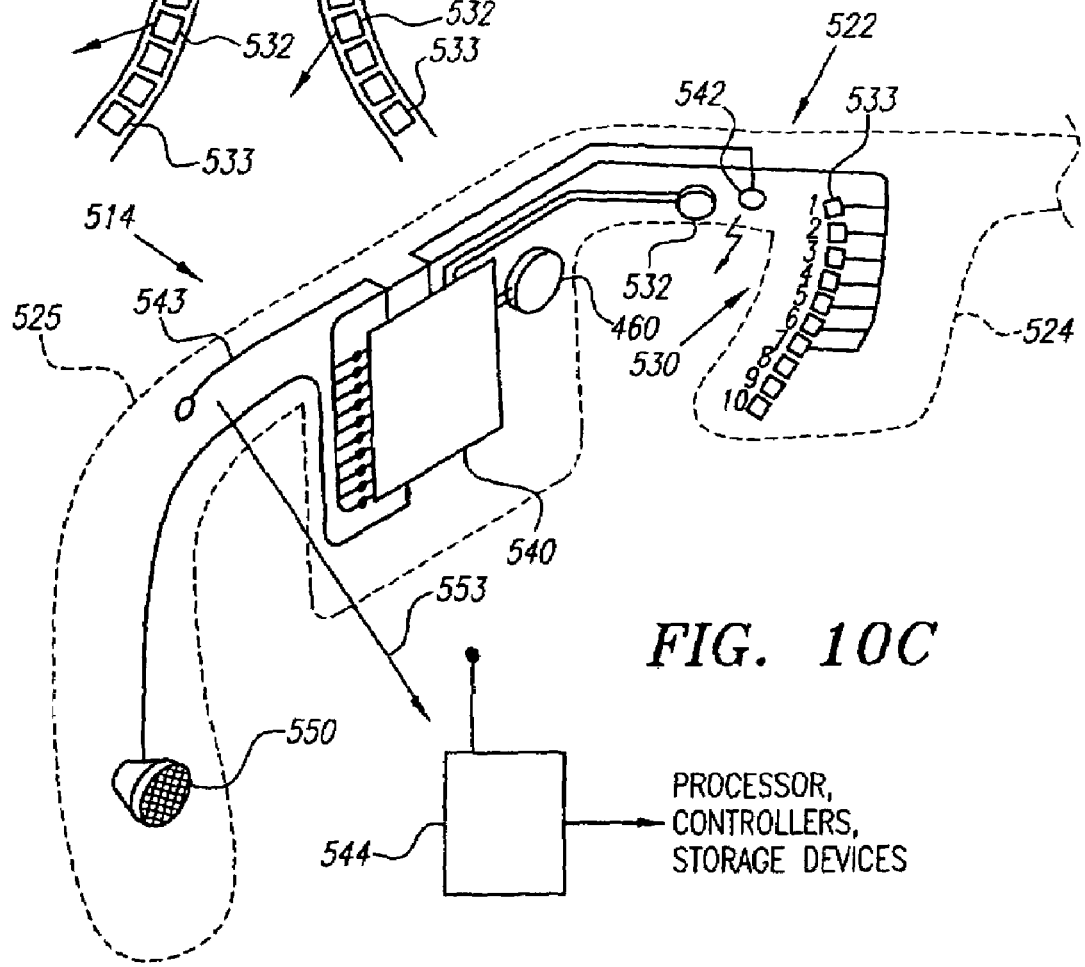
FIG. 10C is a detail of an exemplary array of emitters and sensors that may be provided on a nose bridge of an eye frame, such as that of FIG. 10A.
Figure 10D:
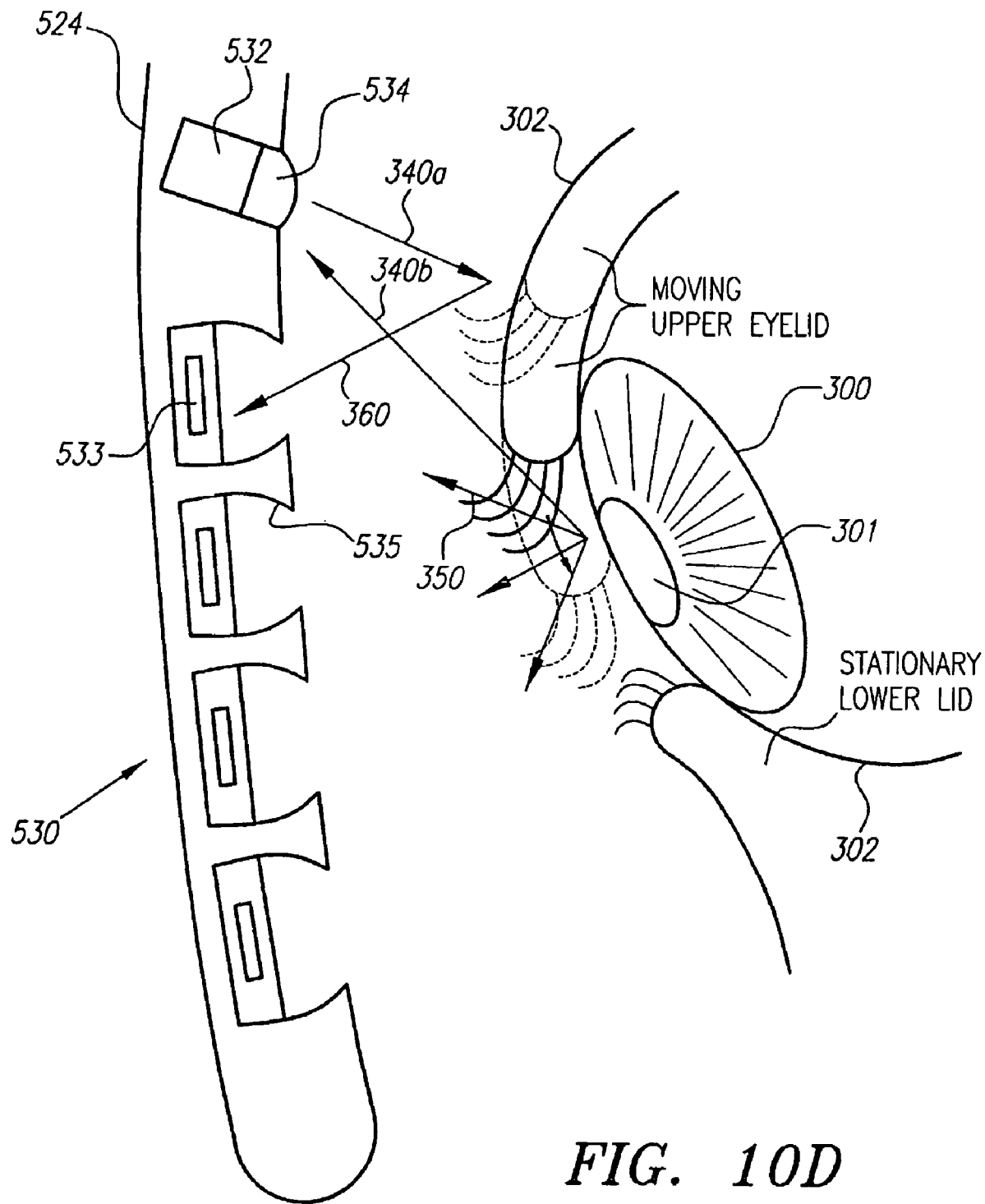
FIG. 10D is a sectional view of the array of emitters and sensors of FIG. 10C emitting light and detecting light reflected from an eye.

In another alternative, shown in FIGS. 10B, 10C, and 10D, a linear array 530 of emitters 532 and sensors 533 may be provided, e.g., in a vertical arrangement mounted on a nose bridge 524 of an eye frame 522. A CPU 540, battery 460, transmitter antenna 543, and warning indicator 550 may also be provided on the frame 522, e.g., in the temple piece 525, similar to the previously described embodiments. An LED 542 or similar stimulus device may also be provided at a predetermined location on the eye frame 522 to allow routine biofeedback responses from the user. In addition, a receiver 544 may be provided for receiving the stream of data created by the CPU 540 and transmitted by the transmitter 543.

As shown particularly in FIG. 10C, each of the sensors 533 and the emitter 532 may be coupled to the CPU 540 or other control circuitry for controlling the emitter 532 and/or for processing the light intensity signals produced by the sensors 532. Thus, the CPU 540 may cycle through the sensors 533 in the array 530 and sequentially process the signal from each of the sensors 533, similar to the processors described elsewhere herein. As shown in FIG. 10D, the emitter 532 includes a lens 534 to focus a beam of light (indicated by individual rays 360a, 360b) onto the eye 300, e.g., towards the pupil 301. The sensors 533 are embedded within the nose bridge 524 and a slit 535 is provided for each, the slits 535 having a predetermined size to control the reflected light detected by each sensor 533. Thus, each sensor 535 may detect movement of the eyelid 302 past a particular portion of the eye 300, e.g., to measure PERCLOS, as shown in FIG. 12A. The sensors or emitters may have lenses or columnating devices to focus emitted or reflected light.

The linear array 530 may facilitate measurement of additional parameters related to eyelid movement in addition to mere eye closure, for example, to measure the velocity of the eyelid opening or closing, i.e., the rate of eye closure, the CPU 540 may compare the time delay between the activation of successive sensors 533. In addition, the output signals from the sensors 553 may be processed to measure the percentage of pupil coverage of the eyelid 302, for example, due to partial eye closure, as a function of time, e.g., to monitor when the eye is partially, but not completely, closed, and/or to monitor the percentage of time that the eye is closed (PERCLOS), as shown in FIGS. 12A-12C, e.g., compared to the user's baseline of maximal eye opening.

Turning to FIG. 12D, in another embodiment, a two-dimensional array of sensors may be provided. Although a 5×5 array 633 and a 9×11 array 733 are shown as exemplary embodiments, other arrays including any number of elements in the array may be provided. For example, as described further below, the sensors may be in the form of a CMOS or CCD device, including hundreds or thousands of pixels in a grid or other pattern. The sensors 633, 733 may then be used to measure surface area reflectivity of light from the emitter 632, i.e., the processor (not shown) may process the signals from each sensor in the array 633, 733 to create a stream of data indicating the percentage of surface area of the eye 300 covered by the eyelid 302 and/or relative position of the pupil.

The sensors in the array 633, 733 may be sufficiently sensitive or have sufficient resolution such that they may detect "red reflex" or the equivalent infrared "bright pupil" reflection due to the reflection of light off of the retina through the pupil 301. Thus, the sensors may produce a light intensity signal that includes a substantially zero value, indicating no red reflex or bright pupil, a low output, indicating red reflex or white pupil reflex, and a high output, indicating reflection off of a closed eyelid 302. The red reflex may appear as a bright white light pupil (resulting from infrared light from the emitter(s) reflecting off of the retina when the eyelid is open, or as a dark or "black pupil" if the processor uses subtraction algorithms). The processor may process the light intensity signals to detect when the pupil 301 is covered by the eyelid 302, i.e., at which point the user cannot see, even though their eye 300 may not be entirely covered by the eyelid 302, generally at a PERCLOS value of about 50-75 percent in primary gaze. Alternatively, as the eyelid, eye, and pupil descend, the sensor(s) may detect a red reflex or bright pupil even though the PERCLOS measurement may be as great as 75-80 percent or more, e.g., where the eye may still see through a narrow slit-like palpebral fissure opening in downward gaze.

In another alternative, the processor and/or transmitter circuitry (such as the CPU 140 in the processor box 130 of FIG. 2, or the CPU's 440, 540 of FIGS. 10A and 10B) may include identification circuitry (not shown), either as a discrete memory chip or other circuit element, or within the CPU itself. The identification circuitry may be preprogrammed with a fixed identification code, or may be programmable, for example, to include selected identification information, such as the identity of the user, the user's location, biometric measures specific to the user (e.g. unique iris or retinal patterns, finger prints, voice identification), an identification code for the individual detection device, and the like.

The CPU may selectively add the identification information to the transmitted stream of data 553, or the identification information may be automatically or periodically, continuously or discontinuously, included in the stream of data 553, thereby allowing the stream of data 553 to be associated with a particular detection device, individual user, and/or a specific location. The identification information may be used by the processor, for example, at a remote location, to distinguish between streams of data received from a number of detection devices, which may then be stored, displayed, etc. as previously described. Thus, the detection device may not require users to consciously communicate certain identification or other standard information when the system is used.

Figure 11A:
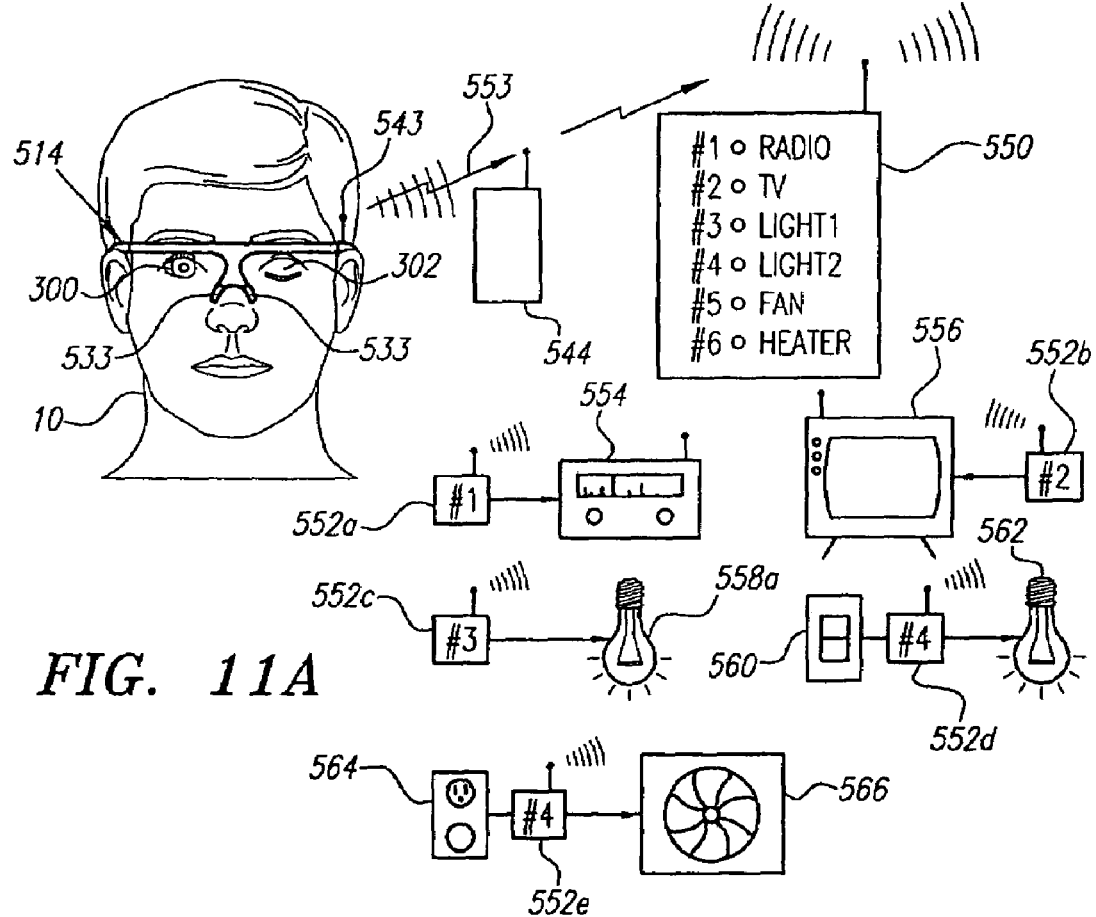
FIG. 11A is a schematic view of a system for selectively controlling a number of devices from a remote location based upon eyelid movement.

As shown in FIG. 11A, the receiver 544 may allow the user to control one or more devices coupled to the receiver 544 through a single switch multi-appliance control unit 550. The control unit 550 includes its own transmitter adapted to transmit on/off or other control signals that may be received by individual control modules 552a-552f. The user 10 may blink to create a transmitted stream of data 553 that includes commands to turn off and on, or otherwise control, selected appliances using the control unit 550 and control modules 552a-552f, such as, a radio 554, a television 556, a light 558a. a light 562 controlled by a wall switch 560, a fan 566 plugged into a wall socket 564, and the like.

Figure 11B:
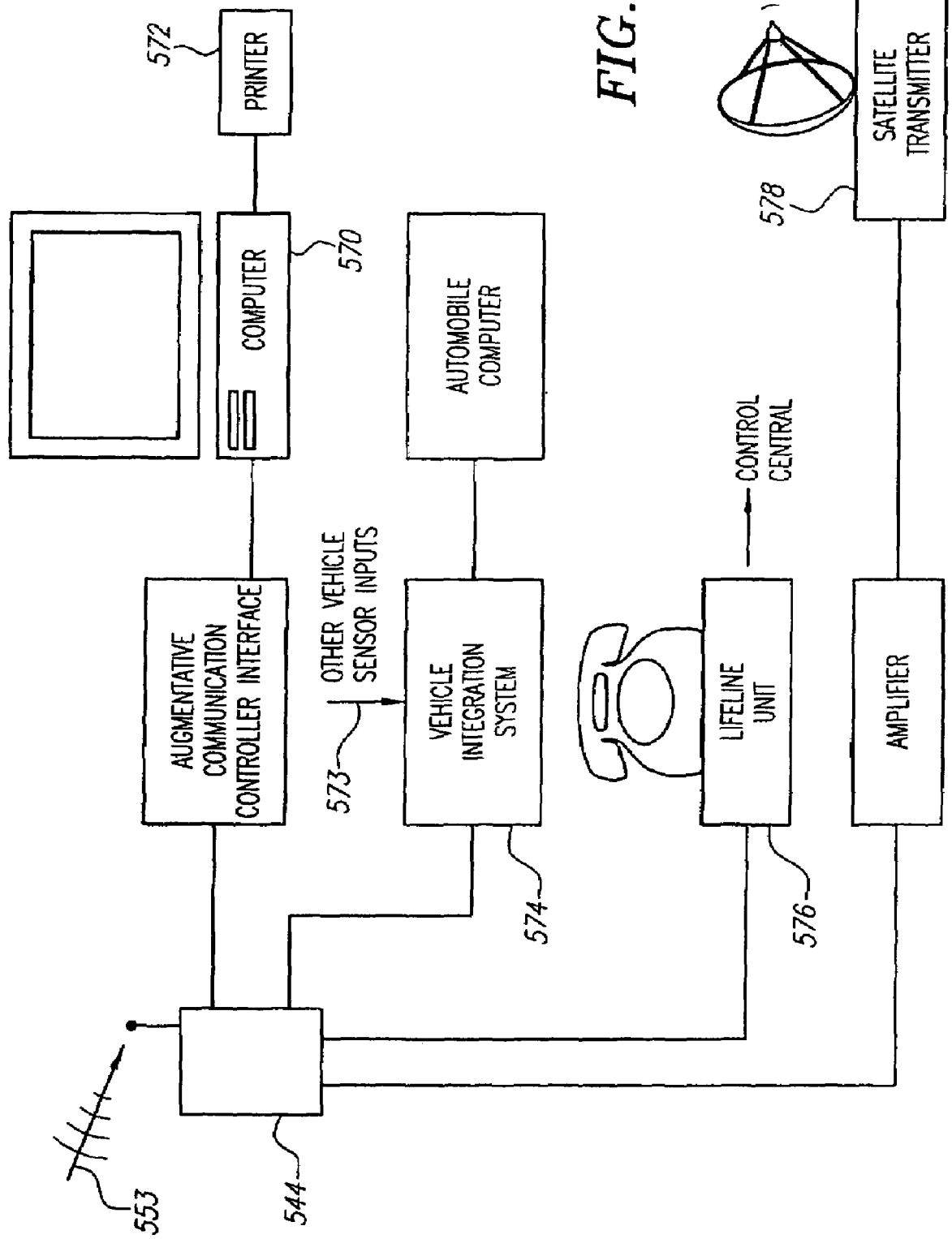
FIG. 11B is a schematic view of additional devices that may be controlled by the system of FIG. 11B.

Alternatively, as shown in FIG. 11B, the receiver 554 may be coupled to other systems, such as a computer 570 and printer 572, a vehicle integration system 574, a lifeline unit 576, a GPS or other satellite transmitter 578, and the like. The transmitted stream of data 553 may be processed alone or along with additional data, such as other vehicle sensor information 573, and/or human factors (e.g. EKG, EEG, EOG, pulse, blood pressure, respiratory rate, oximetry, actigraphy, head position, voice analysis, body temperature, skin conductance, self-assessment measures and performance vigilance responses, observation by others through a fixed non-wearable dash-board or visor-mounted camera system, etc.), to further enhance monitoring a user, such as a long-distance truck driver.

Turning to FIG. 13, yet another embodiment of a system 810 for monitoring eye movement is shown. Generally, the system 810 includes a frame 812 that may include a bridge piece 814 and a pair of ear supports 816, one or more emitters 820, one or more sensors 822, and/or one or more cameras 830, 840. The frame 812 may include a pair of lenses (not shown), such as prescription, shaded, or protective lenses, although they may be omitted. Alternatively, the system may be provided on other devices that may be worn on a user's head, such as a pilot's oxygen mask, protective eye gear, a patient's ventilator, a scuba or swimming mask, a helmet, a hat, a head band, a head visor, protective head gear, or within enclosed suits protecting the head and/or face, and the like (not shown). The components of the system may be provided at a variety of locations on the device that generally minimize interference with the user's vision and/or normal use of the device.

As shown, an array of emitters 820 are provided on the frame 812, e.g., in a vertical array 820a and a horizontal array 820b. In addition or alternatively, the emitters 820 may be provided in other configurations, such as a circular array (not shown), and may or may not include light filters and/or diffusers (also not shown). In an exemplary embodiment, the emitters 820 are infrared emitters configured to emit pulses at a predetermined frequency, similar to other embodiments described elsewhere herein. The emitters 820 may be arranged on the frame such that they project a reference frame 850 onto a region of the user's face including one of the user's eyes. As shown, the reference frame includes a pair of crossed bands 850a, 850b dividing the region into four quadrants. In an exemplary embodiment, the intersection of the crossed bands may be disposed at a location corresponding substantially to the eye's pupil during primary gaze, i.e., when the user is looking generally straight forward. Alternatively, other reference frames may be provided, e.g., including vertical and horizontal components, angular and radial components, or other orthogonal components. Optionally, even one or two reference points that remain substantially stationary may provide sufficient reference frame for determining relative movement of the eye, as explained further below.

An array of sensors 822 may also be provided on the frame 812 for detecting light from the emitters 820 that is reflected off of the user's eyelid. The sensors 822 may generate output signals having an intensity identifying whether the eyelid is closed or open, similar to other embodiments described elsewhere herein. The sensors 822 may be disposed adjacent to respective emitters 820 for detecting light reflected off of respective portions of the eyelid. Alternatively, sensors 822 may only be provided in a vertical array, e.g., along the bridge piece 814, for monitoring the amount of eyelid closure, similar to embodiments described elsewhere herein. In a further alternative, the emitters 820 and sensors 822 may be solid state biosensors (not shown) that provide both the emitting and sensing functions in a single device. Optionally, the emitters 820 and/or sensors 822 may be eliminated, e.g., if the cameras 830, 840 provide sufficient information, as explained further below.

Figure 17:
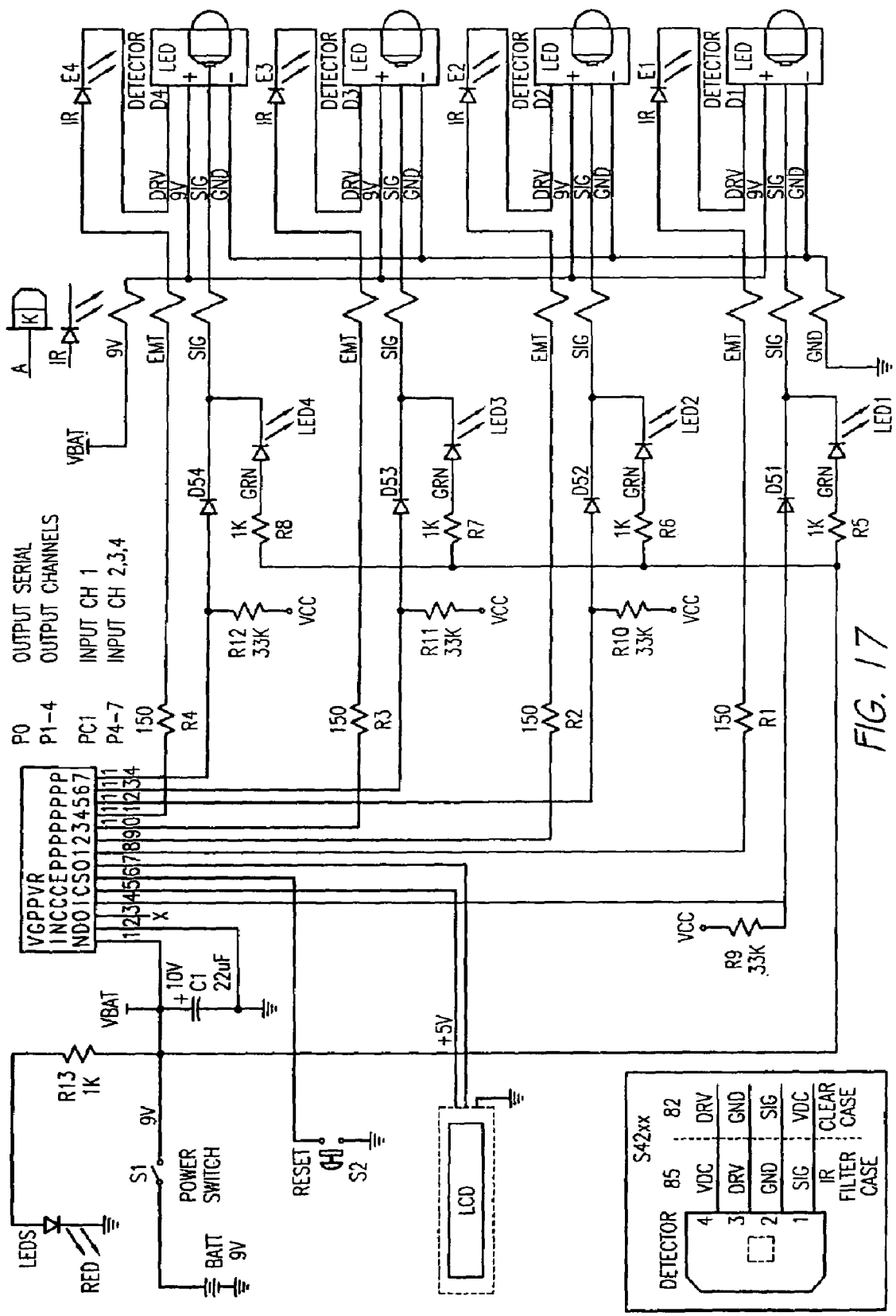
FIG. 17 is a schematic showing an exemplary embodiment of circuitry for processing signals from a five-element sensor array.

Circuitry and/or software may be provided for measuring PERCLOS or other parameters using the signals generated by the array of sensors. For example, FIG. 17 shows an exemplary schematic that may be used for processing signals from a five element array, e.g., to obtain PERCLOS measurements or other alertness parameters.

Returning to FIG. 13, the system 810 also includes one or more cameras 830 oriented generally towards one or both of the user's eyes. Each camera 830 may include a fiber optic bundle 832 including a first end mounted to or adjacent the bridge piece 814 (or elsewhere on the frame 812, e.g., at a location that minimizes interferences with the user's vision), and a second end 837 that is coupled to a detector 838, e.g., a CCD or CMOS sensor, which may convert images into digital video signals. An objective lens 834 may be provided on the first end of the fiber optic bundle 832, as shown in FIG. 14, e.g., to focus images onto the fiber optic bundle 832. Optionally, the fiber optic bundle 832 may include one or more illumination fibers that may terminate adjacent the lens 834 to provide emitters 836, also as shown in FIG. 14. The illumination fiber(s) may be coupled to a light source (not shown), e.g., similar to the embodiment shown in FIG. 22 and described further below. Although only one camera 830 is shown in FIG. 13 (e.g., for monitoring the user's left eye), it will be appreciated that another camera (not shown) may be provided in a symmetrical configuration for monitoring the other of the user's eyes (e.g., the right eye), including similar components, e.g., a fiber optic bundle, lens, emitter(s) and/or detector (although, optionally, the cameras may share a common detector, as explained further below). Optionally, it may be desirable to have multiple cameras (not shown) directed towards each eye, e.g., from different angles facing the eye(s). Optionally, these camera(s) may include fiberoptic extensions, prismatic lenses, and/or reflecting mirrors (e.g., reflecting infrared light), impenetrable or blocking mirrored surfaces on the side of the lenses facing the eyes, and the like. Such accessories may be provided for bending, turning, reflecting, or inverting the images of the eyes transmitted to the camera(s) in a desired manner.

The camera(s) 830 may be configured for detecting the frequency of light emitted by the emitters 820 and/or 836, e.g., infrared light or other light beyond the visible range. Optionally, if the fiber optic bundle(s) 832 include one or more illumination fibers for emitters 836, the emitters 820 on the frame 812 may be eliminated. In this embodiment, it may also be possible to eliminate the sensors 822, and use the camera(s) 830 to monitor movement of the user's eye(s), e.g., as explained further below. Optionally, the system 810 may include a second camera 840 oriented away from the user's head, e.g., to monitor the user's surroundings, such an area directly in front of the user's face. The camera 840 may include similar components to the camera 830, e.g., a fiberoptic bundle 841, lens (not shown), and/or emitter(s) (also not shown). Optionally, the camera 830 may sufficiently sensitive to generate images under ambient lighting conditions, and the emitters may be omitted. The camera 840 may be coupled to a separate detector 839, as shown in FIG. 13, or may share the detector 838 with the camera(s) 830, as explained further below.

Each of the fiberoptic bundles 832, 841 may include, for example, between about five thousand and one hundred thousand (5,000-100,000) pixelated light-carrying optical fibers, or between about ten thousand and fifty thousand (10,000-50,000) fibers. The number of fibers may depend on the particular needs of a given application, e.g., to provide a desired optical resolution in the images obtained of the user's eye(s) (i.e., for the "endocamera(s)" fibers), as well as of the surrounding environment (i.e., for the "exocamera" fibers). Optionally, the fibers for the bundles may include one or more illumination fibers. In exemplary embodiments, bundles may be used having five thousand (5,000) fibers (providing 75×75 pixel resolution), ten thousand (10,000) fibers (providing 100×100 pixel resolution), fifty thousand (50,000) fibers (providing 224×224 pixel resolution), and one hundred thousand (100,000) fibers (providing 316×316 pixel resolution). The resulting fiber optic bundle(s) 832, 841 may have a diameter, for example, between about three to five millimeters (3-5 mm), with or without cladding. The fiber optic bundle(s) 832, 841 may be secured along the frame 812 or may be provided within the frame 812. For example, the frame 812 may be formed with one or more passages, e.g., extending from the bridge piece 814 to the ear supports 816, for receiving the fiber optic bundle(s) 832, 841 therethrough. Alternatively, the fiber optic bundle(s) 832, 841 may be molded, fused, or otherwise embedded into the frame 812, e.g., when the frame 812 is made. Optionally, the fiber optic bundle(s) 832, 841 may extend from the frame 812 to a detector and/or processor (not shown) separate from the frame 812, similar to the embodiments described below with reference to FIGS. 18A and 18B.

One or both of the ear supports 816 may include a panel 818 for mounting one or more components, e.g., a controller or processor, such as exemplary processor 842, a transmitter 844, an antenna 845, detector(s) 838, 839, and/or a battery 846. The processor 840 may be coupled to the emitters 820, the sensors 822, and/or the cameras 830, 840 (e.g., to the detector(s) 838, 839) for controlling their operation. The transmitter 844 may be coupled to the processor 842 and/or detector(s) 838, 839 for receiving the output signals from the sensors 822 and/or cameras 830, 840, e.g., to transmit the signals to a remote location, as described below. Alternatively, the transmitter 844 may be coupled directly to output leads from the sensors 822 and/or the cameras 830, 840. The frame 812 may also include manual controls (not shown), e.g., on the ear support 816, for example, to turn the power off and on, or to adjust the intensity and/or threshold of the emitters 820, the sensors 822, and/or the cameras 830, 840.

If desired, the system 810 may also include one or more additional sensors on the frame 812, e.g., physiological sensors, for example, for the purposes of integration and cross-correlation of additional bio- or neuro-physiological data relating to the cognitive, emotional, and/or behavioral state of the user. The sensors may be coupled to the processor 842 and/or to the transmitter 844 so that the signals from the sensors may be monitored, recorded, and/or transmitted to a remote location. For example, one or more position sensors 852a, 852b may be provided, e.g., for determining the spatial orientation of the frame 812, and consequently the user's head. For example, actigraphic sensors may be provided to measure tilt or movement of the head, e.g., to monitor whether the user's head is drooping forward or tilting to the side. Acoustic sensors, e.g., a microphone 854 may be provided for detecting environmental noise or sounds produced by the user.

In addition or alternatively, the frame 812 may include one or more sensors for measuring one or more physical characteristics of the user, e.g., for the purpose of physiological systems integration and/or cross correlation. For example, EEG electrodes 856 may be provided on the ear support 816, above or below the nasion, on the mastoid, over the occipital area, and/or other region that may contact the user's skin (e.g., moist surface contact electrodes), or may not contact the user's skin (e.g., dry wireless electrodes) to measure and transmit brain activity (e.g., waking, drowsy, or other sleep-related brain activity), e.g., of different frequencies ranging from about one to five hundred Hertz (1-500 Hz) for visual or short or long term spatial and/or temporal trend analysis (e.g. Fast Fourier or spectral analysis). An EKG electrode (not shown) may be provided that is capable of measuring cardiac activity through a skin contact site. A pulse sensor (not shown) may be used to measure cardiovascular pulsations, or an oximetry sensor 858 may be used to measure oxygen saturation levels. A thermistor or other sensor may measure respiratory air flow, e.g., through the user's nose. A thermistor, thermocouple, or other temperature sensor (not shown) may be provided for measuring the user's skin temperature. A sweat detector (not shown) may be provided for measuring moisture on the user's skin, and/or a microphone or other acoustic sensor (also not shown) may be attached to the frame 812 to detect vocal or breathing sounds of the user. One or more electrooculographic (EOG) electrodes may be provided that contact the user's skin at desired areas that measure fluctuations in electrical potentials during movement of the eyes.

In addition, the system 810 may include one or more feedback devices on the frame 812. These devices may provide feedback to the user, e.g., to alert and/or wake the user, when a predetermined condition is detected, e.g., a state of drowsiness or lack of consciousness. The feedback devices may be coupled to the processor 842, which may control their activation. For example, a mechanical vibrator device 860 may be provided at a location that may contact the user, e.g., on the ear support 816, that may provide tactile vibrating stimuli through skin contact. An electrode (not shown) may be provided that may produce relatively low power electrical stimuli. A visible white or colored light emitter, such as one or more LED's may be provided at desired locations, e.g., above the bridge piece 814. Alternatively, audio devices 862, such as a buzzer or other alarm, may be provided, similar to other embodiments described elsewhere herein. In a further alternative, aroma-emitters may be provided on the frame 810, e.g., on or adjacent to the bridge piece 814.

In addition or alternatively, one or more feedback devices may be provided separate from the frame 812, but located in a manner capable of providing a feedback response to the user. For example, audio, visual, tactile (e.g., vibrating seat), or olfactory emitters may be provided in the proximity of the user, such as any of the devices described elsewhere herein. In a further alternative, heat or cold generating devices may be provided that are capable of producing thermal stimuli to the user, e.g., a remotely controlled fan or air conditioning unit.

The system 810 may also include components that are remote from the frame 812, similar to other embodiments described elsewhere herein. For example, the system 810 may include a receiver, a processor, and/or a display (not shown) at a remote location from the frame 812, e.g., in the same room, at a nearby monitoring station, or at a more distant location. The receiver may receive signals transmitted by the transmitter 842, including output signals from the sensors 822, cameras 830, 840, or any of the other sensors provided on the frame 812.

A processor may be coupled to the receiver for analyzing signals from the components on the frame 812, e.g., to prepare the signals for graphical display. For example, the processor may prepare the signals from the sensors 822 and/or cameras 830, 840 for display on a monitor, thereby allowing the user to be monitored by others. Simultaneously, other parameters may be displayed, either on a single or separate display(s). For example, FIGS. 15A-15I show signals indicating the output of various sensors that may be on the frame 812, which may be displayed along a common time axis or otherwise correlated, e.g., to movement of the user's eye and/or level of drowsiness. The processor may superimpose or otherwise simultaneously display the video signals in conjunction with the other sensed parameters to allow a physician or other individual to monitor and personally correlate these parameters to the user's behavior.

In a further alternative, the processor may automatically process the signals to monitor and/or study the user's behavior. For example, the processor may use the output signals to monitor various ocular parameters related to eye movement, such as eye blink duration (EBD), eye blink frequency, eye blink velocity, eye blink acceleration, interblink duration (IBD), PERCLOS, PEROP (percentage eyelid is open), pupil size fluctuations, eye gaze and eye ball movements, and the like, such as those described in U.S. Pat. No. 6,542,081, incorporated by reference herein.

Figure 16:
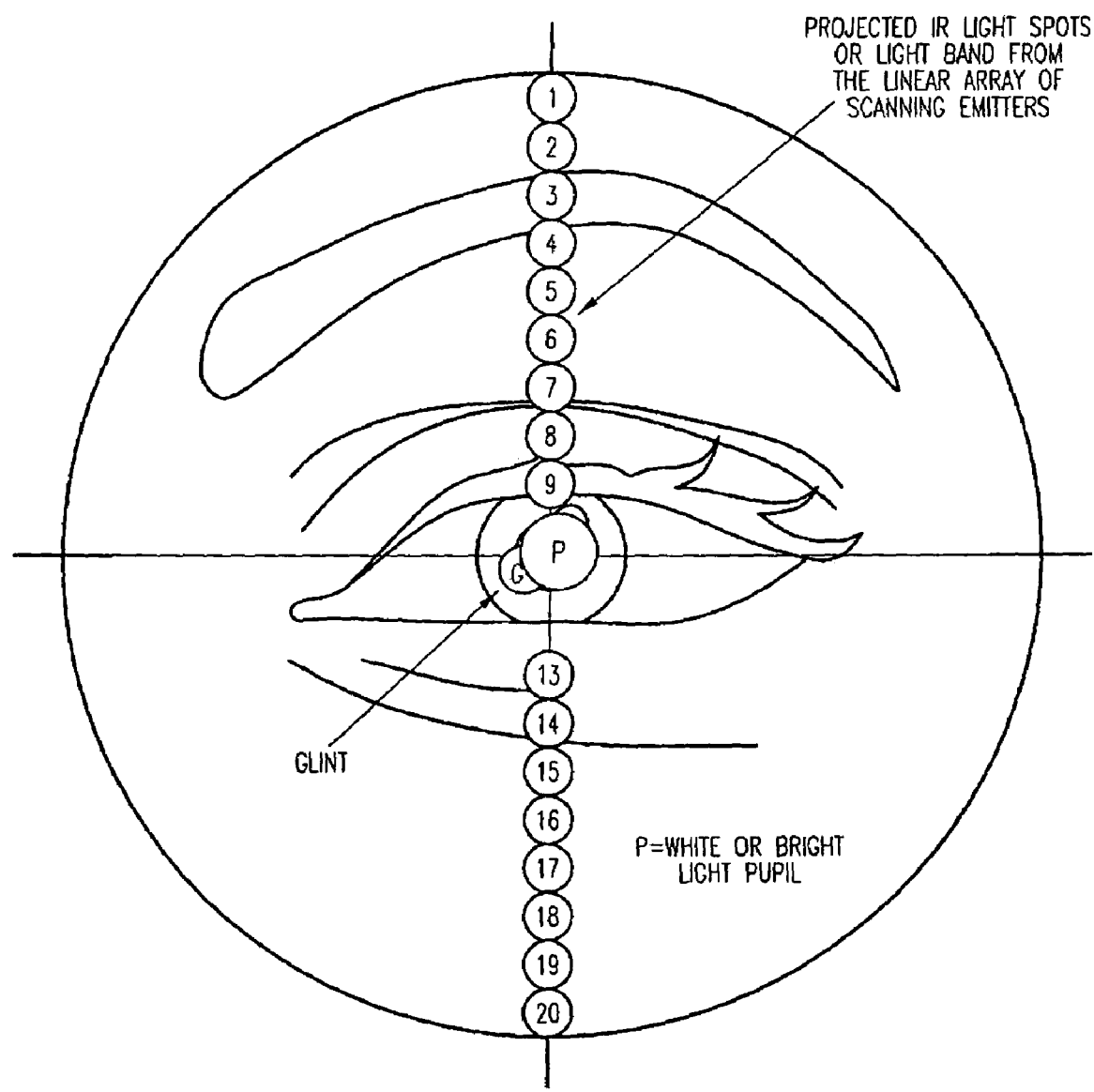
FIG. 16 is a detail of video output from a camera on the frame of FIG. 13.

The video signals from the camera 830 may be processed to monitor various eye parameters, such as pupillary size, location, e.g., within the four quadrant defined by the crossed bands 850, eye tracking movement, eye gaze distance, and the like. For example, because the camera(s) 830 may be capable of detecting the light emitted by the emitters 822, the camera(s) 830 may detect a reference frame projected onto the region of the user's eye by the emitters. FIG. 16 shows an exemplary video output from a camera included in a system having twenty emitters disposed in a vertical arrangement. The camera may detect twenty discrete regions of light arranged as a vertical band. The camera may also detect a "glint" point, G, and/or a moving bright pupil, P. Thus, the movement of the pupil may be monitored in relation to the glint point, G, and/or in relation to the vertical band 1-20.

Because the emitters 822 are fixed to the frame 812, the reference frame 850 may remain substantially stationary relative to the user. Thus, the processor may determine the location of the pupil in terms of orthogonal coordinates (e.g., x-y or angle-radius) relative to the reference frame 850. Alternatively, if the reference frame is eliminated, the location of the pupil may be determined relative to any stationary "glint" point on the user's eye or other predetermined reference point. For example, the camera 830 itself may project a point of light onto the eye that may be reflected and detected by the camera. This "glint" point may remain substantially stationary since the camera 830 is fixed to the frame 812, thereby providing the desired reference point from which subsequent relative movement of the eye may be determined.

In addition, video signals from a remote camera separate from the frame 812 may image the user's face from a distance (e.g., on the dashboard of a car, a drive, flight, or other simulator, or in a sonar, radar, or other monitoring station), e.g., to monitor various facial measures, such as facial expression, yawning frequency, and the like, in addition, or alternative to, the projected light reference frame from the emitters. In addition or alternatively, the parameters from other sensors may be processed and correlated, such as head orientation, tilt, body movement, physiological parameters, and the like. In one embodiment, the processor may correlate two or more of these various parameters to generate a composite fatigue index ("COFI"). For example, when eye blinks or pupil coverage by the eyelid exceed a threshold duration, the processor may monitor the position sensors to detect head tilt and/or the physiological sensors for brain activity likely to indicate that the user is falling asleep or otherwise becoming incapable of driving or operating equipment. The processor may assign numerical values to these parameters using an empirical algorithm stored in memory and add or otherwise correlate the parameters to assign a numerical COFI to the user's current condition.

When a predetermined COFI threshold is exceeded, the system 810 may activate an alarm or otherwise notify the user and/or another party at a remote location. Thus, the system 810 may provide a more effective way to monitor the user's fatigue, drowsiness, alertness, mental state, and the like. In a further alternative, the system 810 may be used to generate predetermined outputs, e.g., to activate or deactivate equipment, such as a vehicle being operated by the user when a predetermined condition, e.g., COFI value, is determined by the system 810.

Alternatively, the processor may be provided on the frame 812, e.g. as part of processor 842, for monitoring the parameters for a predetermined event to occur, such as exceeding a predetermined COFI threshold. In a further alternative, the eye tracking parameters described above may be monitored by a remote camera, e.g., in a fixed position in front of the user, such as the dashboard of a vehicle and the like. The remote camera may be coupled to the processor, either directly or via its own transmitter, which may also be integrated into the COFI determination and/or monitored by third parties along with algorithmically defined response measures. Additional information on the various apparatus, systems, and methods for using them are described in U.S. Pat. Nos. 6,163,281, issued Dec. 19, 2000, 6,246,344, issued Jun. 12, 2001, and 6,542,081, issued Apr. 1, 2003, the entire disclosures of which are expressly incorporated by reference herein.

Figure 20A:
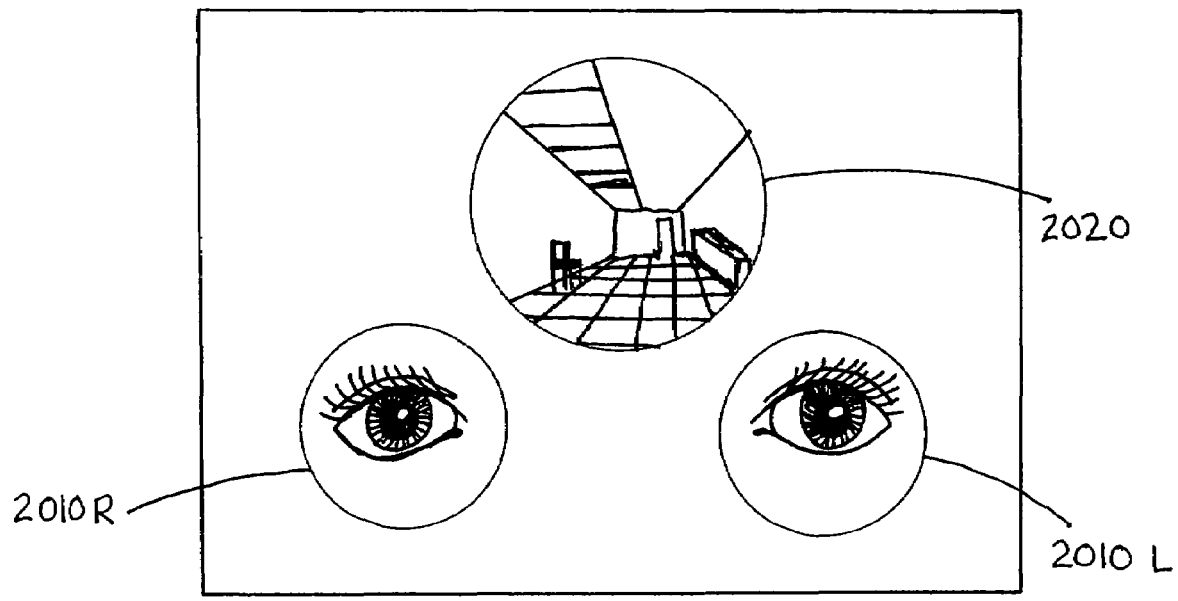
FIGS. 20A and 20B are graphical images, showing simultaneous outputs from multiple cameras, showing the user's eyes open and closing, respectively.
Figure 20B:
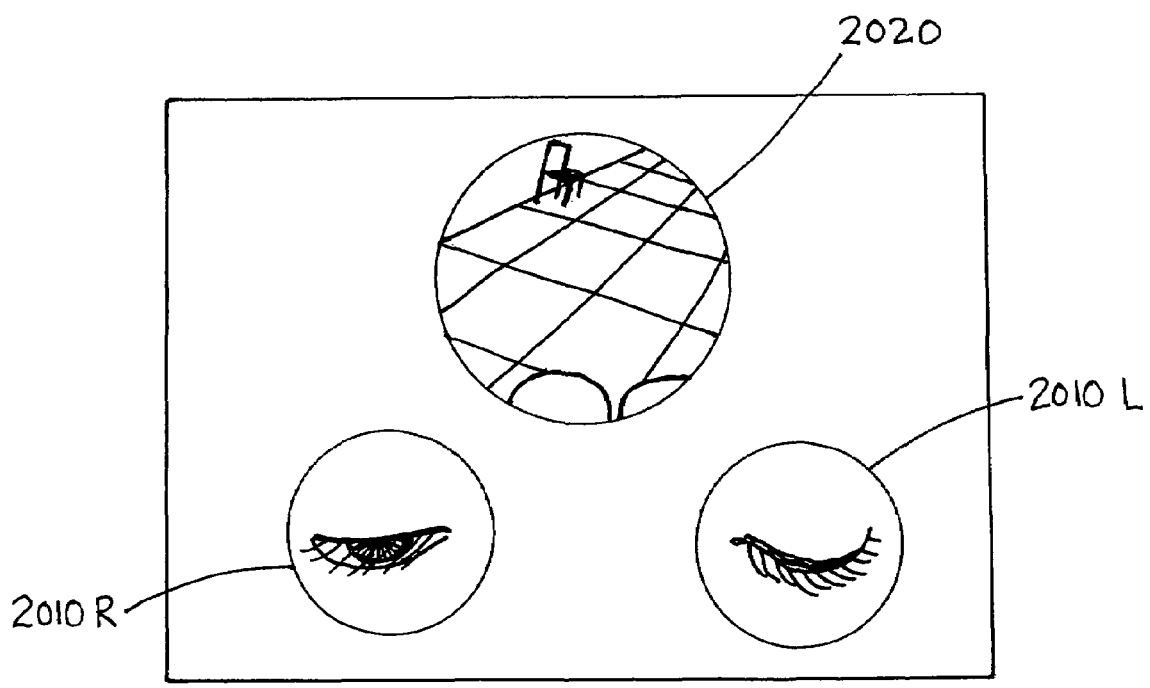

Returning to FIG. 13, in an alternative embodiment, the cameras 832, 840 may be coupled to a single detector (not shown), similar to the configuration shown in FIG. 22. The fiber optic bundles 832, 841 may be coupled to one or more lenses for delivering and/or focusing images from the cameras 830, 840 onto respective regions of the detector. The detector may be a CCD or CMOS chip having an active imaging area, e.g., between about five and ten millimeters (5-10 mm) in cross-section. In exemplary embodiments, the active imaging area of the detector may be square, rectangular, round, or elliptical, as long as there is sufficient area for receiving simultaneous images from both cameras 830 and camera 840. Exemplary outputs displaying simultaneous video images from the cameras 830, 840 is shown in FIGS. 20A and 20B, and described further below. In this alternative, with sufficient resolution and processing, it may be possible to eliminate the emitters 820 and/or sensors 822 from the system 810.

Figure 18A:
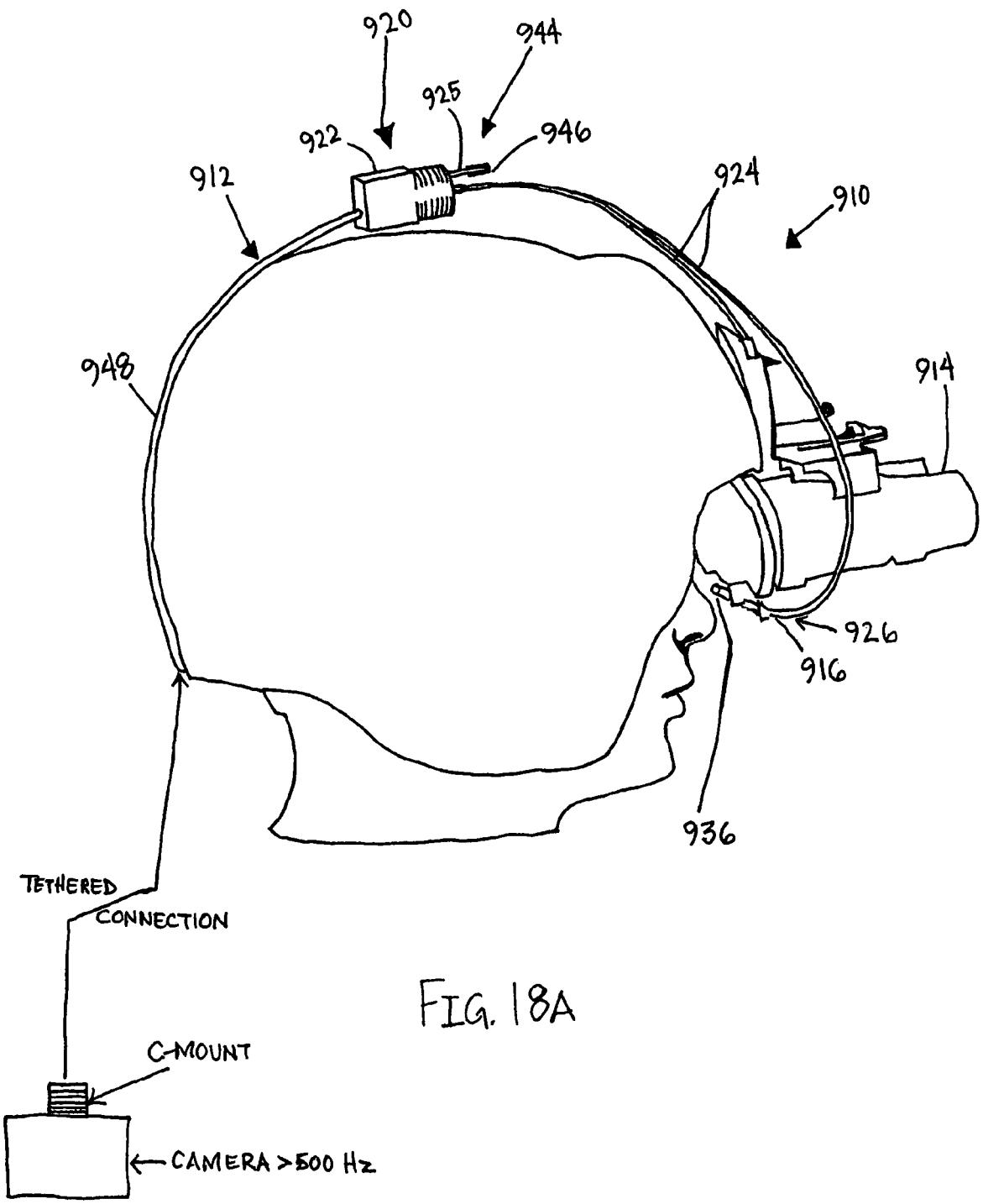
FIGS. 18A and 18B show another embodiment of an apparatus for monitoring eye movement incorporated into an aviator helmet.
Figure 18B:
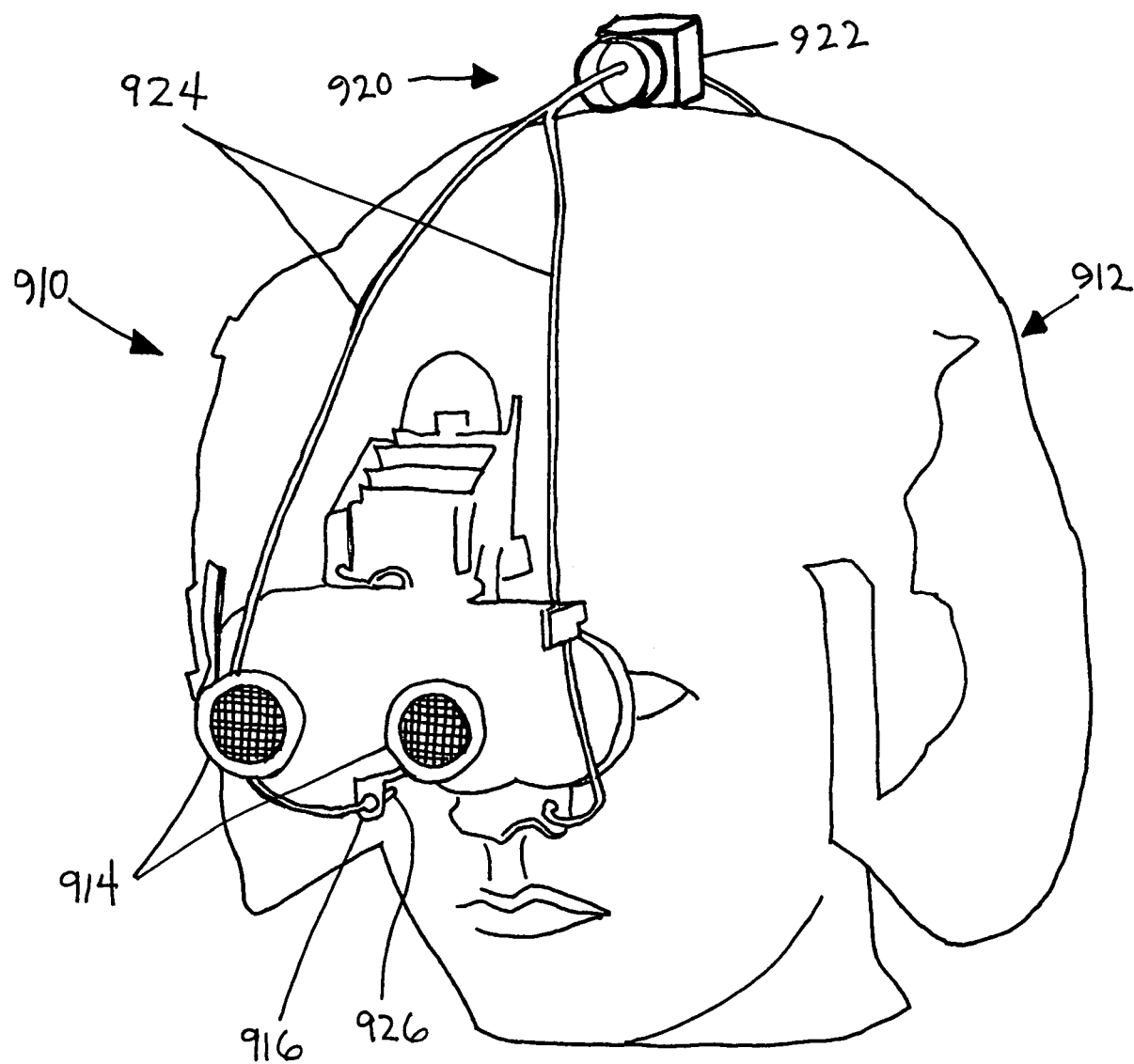

Turning to FIGS. 18A and 18B, another embodiment of an apparatus 910 is shown for monitoring eyelid movement of an individual wearing the apparatus 910. As described elsewhere herein, the apparatus 910 may be used as a biosensor, a communicator, and/or a controller, and/or may be included in a system, e.g., for monitoring voluntary-purposeful and/or involuntary-nonpurposeful movement of one or both of the user's eyes.

As shown, the apparatus 910 includes a helmet 912 that may be worn on a user's head, and a biosensor assembly 920. The helmet 912 may be a standard aviator's helmet, such as those used by helicopter or jet aircraft pilots, e.g., including a pair of night vision tubes or other goggles 914 mounted thereon. Optionally, the helmet 912 may include one or more heads-up displays, e.g., small flat-panel LCDs mounted in front of or adjacent one or both eyes. Alternatively, the helmet 912 may be replaced with a frame (not shown, see, e.g., FIG. 13) including a bridge piece, a rim extending above or around each eye, and/or a pair of ear supports, similar to other embodiments described herein. The frame may include a pair of lenses (also not shown), such as prescription, shaded, and/or protective lenses, although they are not necessary for operation of the apparatus. Alternatively, one or both lenses may be replaced with displays, e.g., relatively small flat panel LCDs, which may be used as a simulator and/or recreational device, as explained further below. In further alternatives, the apparatus 910 may include other devices that may be worn on a user's head, such as a hat, cap, head band, head visor, protective eye and head gear, face mask, oxygen mask, ventilator mask, scuba or swimming mask, and the like (not shown).

The components of the apparatus 910 may be provided at a variety of locations on the helmet 912 (or other head-worn device), e.g., to generally minimize interference with the user's vision and/or normal activity while wearing the apparatus 910. As shown, the biosensor assembly 920 includes a camera 922 mounted on top of the helmet 912, e.g., using Velcro, straps, and/or other temporary or removable connectors (not shown). This may allow the camera 922 to be removed when not in use. Alternatively, the camera 922 may be substantially permanently connected to the helmet 912, incorporated directly into the helmet 912 (or other frame), connected to a head-mounted television, LCD monitor or other digital display, and the like, similar to other embodiments described herein.

The biosensor assembly 920 also includes one or more fiber optic bundles 924 that extend from the camera 922 to the front of the helmet 912 to provide one or more "endocameras" for imaging the user's eye(s). As shown, a pair of fiber optic bundles 924 are shown that extend from the camera 922 to respective tubes of the goggles 914. In the exemplary embodiment, the fiber optic bundles 924 may be sufficiently long to extend from the camera 922 to the goggles 914, e.g., between about twelve and eighteen inches long, although alternatively, the fiber optic bundles 924 may be longer, e.g., between about two and four feet long, or shorter, depending upon the location of the camera 922 on the helmet 910 (or if the camera 922 is provided separately from the helmet 910).

Ends 926 of the fiber optic bundles 924 may be permanently or removably attached to the goggles 914, e.g., to brackets 916 connected to or otherwise extending from the goggles 914. Alternatively, the fiber optic bundles 924 may be held temporarily or substantially permanently onto the goggles 914 using clips, fasteners, adhesives, and the like (not shown). As shown, the ends 926 of the fiber optic bundles 924 are mounted below the goggles 914 and angled upwardly towards the eyes of the user. The angle of the ends 926 may be adjustable, e.g., about fifteen degrees up or down from a base angle of about forty five degrees. Alternatively, the ends 926 of the fiber optic bundles 924 may be provided at other locations on the helmet 912 and/or goggles 914, yet be directed towards the eyes of the user.

Figure 19:
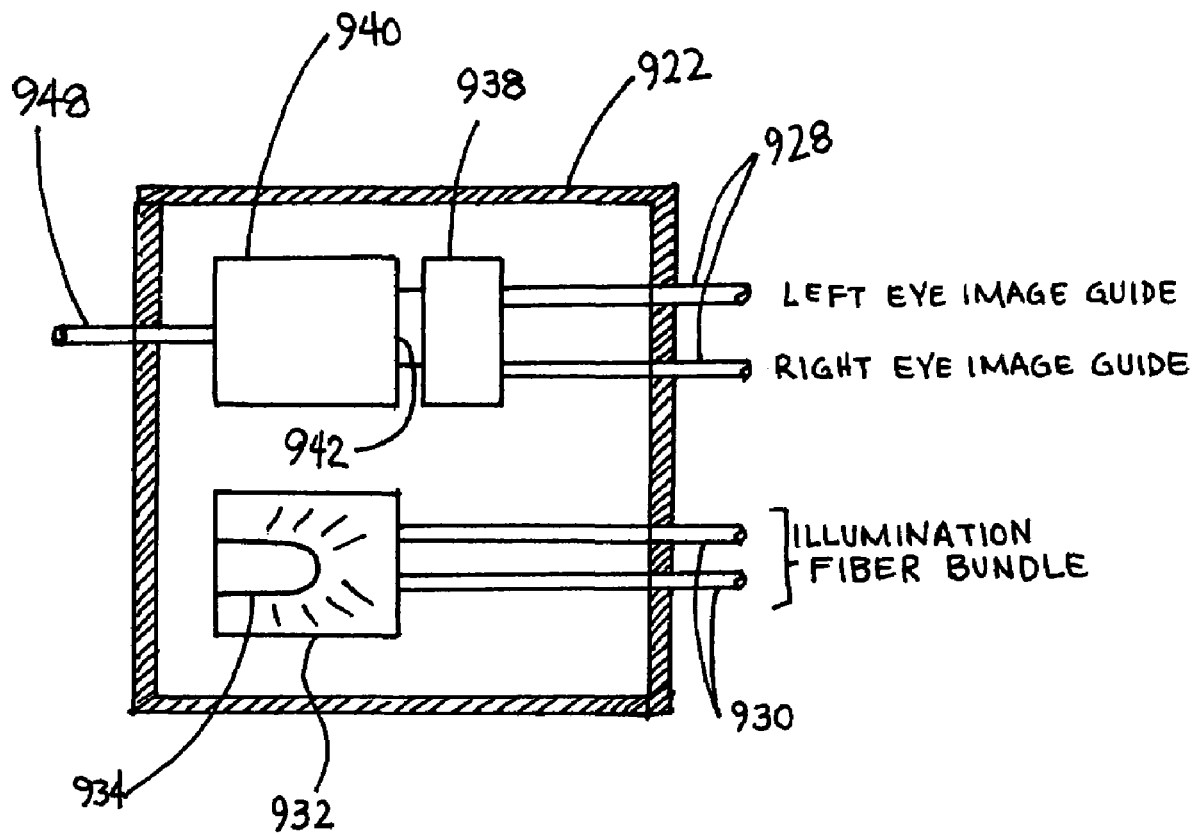
FIG. 19 is a schematic of a camera that may be included in the apparatus of FIGS. 18A and 18B.

With additional reference to FIG. 19, each fiber optic bundle 924 may include a fiber optic image guide 928, i.e., a bundle of optical imaging fibers, and an illumination fiber bundle 930, e.g., encased in shrink tubing (not shown), extending between the camera 922 and the ends 926 of the fiber optic bundle 924. Each illumination fiber bundle 930 may include one or more optical fibers coupled to a light source, e.g., within the camera 922. For example, the camera 922 may include a light emitting diode (LED) housing 932 including one or more LEDs 934 (one shown for simplicity), and the illumination fiber bundle(s) 930 may be coupled to the LED housing 932 to deliver light to the end(s) 926.

The light emitted by the light source 934 may be outside the range of normal human vision, for example, in the infrared range, e.g., with a nominal output wavelength between about eight hundred forty and eight hundred eighty nanometers (840-880 nm), such that the light emitted does not interfere substantially with the user's normal vision. The light source may generate light substantially continuously or light pulses at a desired frequency, similar to the embodiments described elsewhere herein. Alternatively, other sources of light for illuminating the face and/or one or both eyes of the user may be provided instead of the illumination fiber bundle 930. For example, similar to the embodiments described elsewhere herein, one or more emitters (not shown) may be provided, e.g., an array of emitters disposed along one or more regions of the helmet 912 and/or goggles 914.

The end 926 of each fiber optic bundle 924 may include one or more lenses, e.g., an objective lens 936 (shown in FIG. 18A) that may focus the image guide 928 in a desired manner, e.g., towards an eye of the user. Each image guide 928 may have forward line of sight (zero degrees (0°) field of view) and the objective lens 936 may provide a wider field of view, e.g., about forty five degrees (45°). Optionally, the line of sight may be adjustable, e.g., between about thirty and sixty degrees (30-60°) by adjusting the objective lens 936. Further, the objective lens 936 may optimize the viewing distance, e.g., to about two inches (2 in.), thereby improving focus on the user's eye(s). Thus, the image guide(s) 928 may carry images of the user's eye(s) through the fiber optic bundle(s) 924 to the camera 922.

As shown in FIG. 19, the camera 922 may include one or more lenses, e.g., a magnification section 938, for delivering and/or focusing images from the image guide(s) 928 (and/or camera 944) onto the active area 942 of the imaging device 940. The imaging device 940 may be a variety of known devices that provide a two-dimensional active area for receiving images, e.g., a CMOS or CCD detector. In an exemplary embodiment, the imaging device 940 may be a CMOS device, such as that made by Sensovation, Model cmos SamBa HR-130, or Fast Camera 13 made by Micron Imaging, Model MI-MV13. The magnification section 938 may be mechanically mated to the camera 922 via a C-mount or other connection (not shown).

In an exemplary embodiment, each image guide 928 may be capable of providing as many as ten to fifty thousand (10,000 to 50,000) pixels of image data, e.g., similar to the fiberoptic bundles described elsewhere herein, which may be projected onto the active area 942 of the imaging device 940. For the apparatus 910 shown in FIGS. 18A and 18B, the images from both fiber optic bundles 924 are projected onto a single imaging device 940, as shown in FIG. 19, i.e., such that the images from each of the user's eyes occupy less than half of the active area 942.

Optionally, the apparatus 910 may include an "exocamera" 944 oriented away from the user's head, e.g., to monitor the user's surroundings, similar to the embodiments described elsewhere herein. For example, as shown in FIG. 18A, another fiber optic bundle 945 may be provided that extends from the camera 922. As shown, the fiber optic bundle 945 is oriented "forward," i.e., generally in the same direction as when the user looks straight ahead, and terminates in a microlens 946. This fiber optic bundle 945 may be relatively short and/or substantially rigid such that its field of the view is substantially fixed relative to the helmet 912. Alternatively, the exocamera 944 may be provided at other locations on the helmet 912 and/or goggles 914, e.g., including a flexible fiberoptic bundle, similar to the exocamera 840 described above. Thus, the exocamera 944 may provide images away from the user, e.g., straight ahead of the user's face.

The exocamera 944 may or may not include one or more illumination fibers, but may include an image guide that may be coupled to the imaging device 940, e.g., via the magnification section 938 or separately. Thus, the images from the exocamera 944 may be delivered onto the same active area 942 as the images of each of the user's eyes received from the image guides 928, similar to other embodiments described herein. This configuration may allow or facilitate temporal and/or spatial synchronization, allowing for overlaying or superimposing endocamera image(s) over exocamera images, or through "triangulation measurements" or other algorithms for eye tracking purposes to identify "where," "what," and/or "how long" (duration of gaze) the user's eyes are looking at relative to the user's head directional position.

Thus, the camera 922 may simultaneously capture images from one or more "endocameras," i.e., from fiber optic bundles 924 and from the exocamera 944. This may ensure that the images captured by each device are synchronized with one another, i.e., linked together in time such that an image of one eye taken at a specific time correspond to an image of the other taken at substantially the same time. Further, these images may be substantially synchronized with data from other sensors, e.g., one or more physiological sensors, which may enhance the ability to monitor and/or diagnose the user, and/or predict the user's behavior. Because of this synchronization, image data may be captured at relatively high rates, e.g., between about five hundred and seven hundred fifty frames per second or Hertz (500-750 Hz). Alternatively, separate detectors may be provided, which capture image data that may be synchronized, e.g., by a processor receiving the data. In this alternative, slower capture rates may be used, e.g., between about thirty and sixty Hertz (30-60 Hz), to facilitate synchronization by a processor or other device subsequent to capture. Optionally, the camera 922 and/or associated processor may be capable of capturing relative slow oculometrics, e.g., at rates of between about fifteen and sixty (15-60) frames per second.

FIGS. 20A and 20B illustrate exemplary outputs from a camera receiving simultaneous image signals from two endocameras 2010 and an exocamera 2020 (or from a device compiling images from separate cameras and/or detectors). As shown, an endocamera is directed towards each of the user's eyes, and the exocamera is directed outwardly at the user's surroundings (i.e., generally straight in front of the user's face). In FIG. 20A, both of the user's eyes 2010L, 2010R are open and the exocamera image 2020 shows a horizontal view of the room ahead of the user. In contrast, in FIG. 20B, one of the user's eyes 2010L is completely closed, and the other eye 2010R is partially closed such that the eyelid covers most of the pupil. The exocamera image 2020 shows that the user's head has begun to tilt to the left and droop forward. Optionally, additional information may be displayed and/or stored along with these images, such as real time data from other sensors on the apparatus 910, similar to that shown in FIGS. 12A-12C or FIGS. 15A-15I.

Returning to FIGS. 18A, 18B, and 19, the images from the camera 922 (and/or camera 944) may be transferred from the apparatus 910 via cable 948 (best seen in FIG. 18A). For example, the imaging device 940 may convert the optical images from the active area 942 into electrical signals that may be carried via the cable 948 to one or more processors and/or controllers (not shown), similar to other embodiments described elsewhere herein. Alternatively, images from the fiberoptic bundles 924 and/or exocamera 944 may be carried from the apparatus 910 to one or more remote devices, e.g., camera, detector, and/or processor (not shown), similar to other embodiments described herein. In this alternative, the bundles 924 may be between about two and six feet long, e.g., providing sufficient length to allow the user to move normally yet remain coupled to the remote device(s).

Alternatively or in addition, the apparatus 910 may include a wireless transmitter (not shown), such as a short or long range radio frequency (RF) transmitter, e.g., using Bluetooth or other protocols, that may be coupled to the camera 922. The transmitter may be located in the camera 922 or elsewhere on the helmet 912. The transmitter may transmit images signals representing the image data to a receiver at a remote location, similar to other embodiments described elsewhere herein. In yet another alternative, the apparatus 910 may include memory (also not shown) for storing the image data, either instead of or in addition to the transmitter and/or cable 948. For example, the data may be stored in a recorder device, e.g., similar to a "black box" recorder used in aircraft, such that the recorder may be retrieved at a later time, e.g., for analysis after a vehicular accident, medical incident, and the like.

Optionally, the apparatus 910 may include one or more controllers (not shown), e.g., within the camera 922, and/or on or in the helmet 912 for controlling various components of the apparatus 910. For example, a controller may be coupled to the one or more LEDs 934 such that the LEDs 934 emit pulses at a predetermined frequency, e.g., to reduce energy consumption of the apparatus 910. In addition, the apparatus 910 may include one or more power sources, e.g., batteries and/or cables, for providing electrical power to one or more components of the apparatus 910. For example, one or more batteries (not shown) may be provided in the camera 922 for providing power to the imaging device 940 and/or the LED(s) 934.

If desired, the apparatus 910 may also include one or more additional sensors (not shown), e.g., on the helmet 910. The sensors may be coupled to the biosensor assembly 920, cable 948, and/or wireless transmitter (not shown) if included so that the signals from the sensors may be monitored, recorded, and/or transmitted to a remote location. For example, one or more position sensors may be provided, e.g., for determining the spatial orientation of the helmet 912, and consequently the user's head, as described elsewhere herein. In addition or alternatively, the apparatus 910 may include one or more physiological sensors (not shown), e.g., for measuring one or more physical characteristics of the user, such as one or more EEG electrodes, EKG electrodes, EOG electrodes, pulse sensors, oximetry sensors, thermistors, thermocouples, or other temperature sensors, e.g., for measuring the user's skin temperature, sweat detectors for measuring moisture on the user's skin, and/or sensors for measuring respiratory air flow, e.g., through the user's nose.

In addition, the apparatus 910 may include one or more feedback devices (also not shown), e.g., to alert and/or wake the user, such as a mechanical vibrator device that may provide tactile vibrating stimuli through skin contact, one or more electrodes that may produce relatively low power electrical stimuli, one or more light emitters, such as LEDs, audio devices, aroma-emitters, and the like. Alternatively, feedback devices may be provided separate from the apparatus 910, but located in a manner capable of providing a feedback response to the user. For example, audio, visual, tactile (e.g., a vibrating seat), or aroma-emitters may be provided in the proximity of the user, such as any of the devices described above. In a further alternative, heat or cold generating devices may be provided that are capable of producing thermal stimuli to the user, e.g., a remotely controlled fan or air conditioning unit.

A system including the apparatus 910 may include components that are remote from the apparatus 910, similar to other embodiments described elsewhere herein. For example, the system may include one or more receivers, processors, and/or displays (not shown) at a remote location from the apparatus 910, e.g., in the same room, at a nearby monitoring station, or at a more distant location. The receiver may receive signals transmitted by a transmitter on the apparatus 910, including image signals from the camera 922 and/or signals from other sensors on the apparatus 910.

A processor may be coupled to the receiver for analyzing signals from the apparatus 910, e.g., to prepare the signals for graphical display. For example, the processor may prepare the video signals from the camera 922 for display on a monitor, similar to the images shown in FIGS. 20A and 20B, thereby allowing the user to be monitored by third parties, e.g., medical professionals, supervisors or other co-workers, and the like. Simultaneously, other parameters may be displayed, either on a single monitor or on separate displays, similar to other embodiments described elsewhere herein. The processor may superimpose or otherwise simultaneously display video signals of the user's eyes and/or exocamera images, alone or in conjunction with the other sensed parameters, to allow a physician or other individual to monitor and personally correlate these parameters to the user's behavior.

In a further alternative, the processor may automatically process the signals to monitor or study the user's behavior. For example, the processor may use the output signals to monitor various parameters related to eye movement, such as eye blink duration (EBD), eye blink frequency, eye blink velocity, eye blink acceleration, interblink duration (IBD), PERCLOS, PEROP (percentage eyelid is open), and the like. The video signals from the camera 922 may be processed to continuously or discontinuously and/or sequentially monitor single or multiple eye parameters, in any combination or pattern of acquisition, such as pupillary size, relative location, eye tracking movement, eye gaze distance, and the like, as described elsewhere herein. Thus, the apparatus 910 and/or system may monitor one or more oculometrics or other parameters, such as those disclosed in U.S. Pat. No. 6,542, 081, incorporated by reference herein.

To facilitate monitoring pupillary size (e.g., dilation, constriction, and/or eccentricity) and/or eye movement, the system may include a processor communicating with the camera 922 for processing the video signals and identifying a pupil of the eye from the video signals. For example, with higher resolution cameras, such as CMOS and CCD detectors, the processor may be able to identify the edges, and consequently the circumference, diameter, and/or cross-sectional area of the pupil. A display may be coupled to the processor for displaying video images of the eye from the video signals processed by the processor.

Figure 21A:
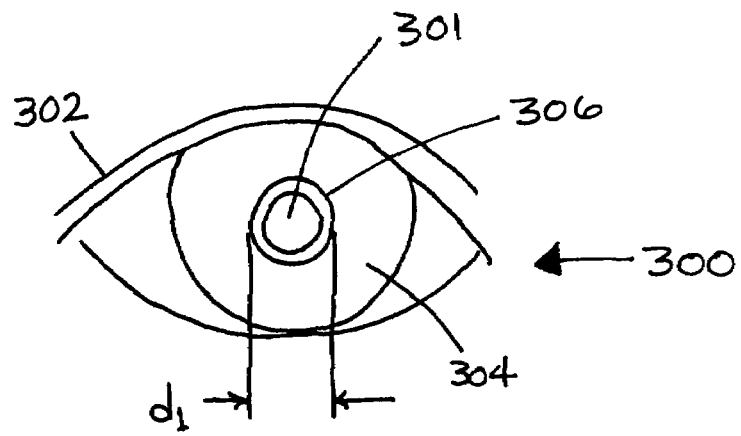
FIGS. 21A-21C are graphical displays, showing an elliptical graphic being created to identify a perimeter of a pupil to facilitate monitoring eye movement.
Figure 21B:
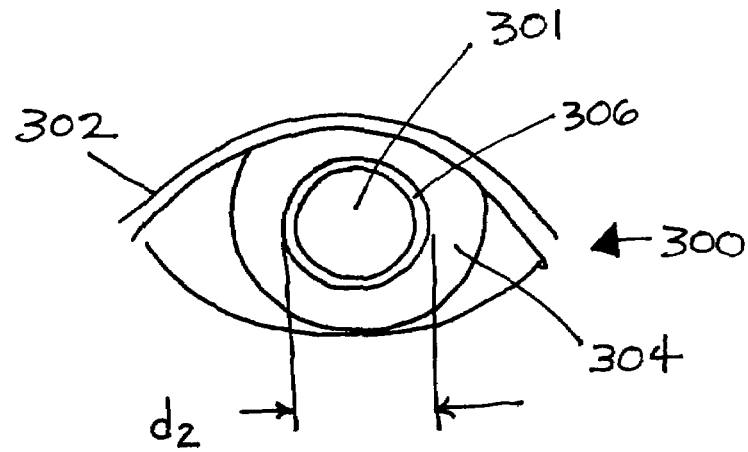
Figure 21C:
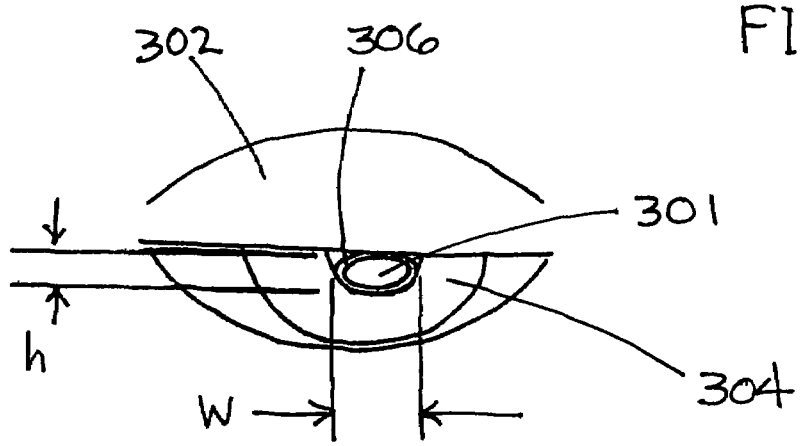

In addition, turning to FIGS. 21A-21C, a processor may superimpose a graphic on the display, e.g., onto the video images to facilitate identifying and/or monitoring the pupil 301 of an eye 300. As shown, because of the contrast between the edge of the pupil 301 and the surrounding iris 304, the processor may approximate this border, and create a graphic halo, ellipse, or other graphic 306 that may be superimposed on the image data of one or both eyes (only one eye 300 shown in FIGS. 21A-21C for simplicity). An observer may use this graphic 306 to facilitate monitoring the user of the apparatus 910.

In addition or alternatively, the processor may automatically analyze the information regarding the size and/or shape of the pupil 301 (or the graphic 306), thereby correlating the video signals to determine the person's level of drowsiness or other physical and/or mental condition. This analysis may include monitoring the relative location of the pupil, a size of the pupil, and/or an eccentricity of the pupil, e.g., over time. For example, the processor may monitor the diameter of the pupil 300 over time, which may displayed in chart form, e.g., as shown in FIG. 1SE, stored in memory as a function of time, and/or superimposed on images of the eye, e.g., in real time.

For example, FIG. 21A may show the pupil 301 in a relaxed state under ambient conditions, e.g., corresponding to graphic 306 having a diameter "$d_1$." As shown in FIG. 21B, if the user blinks or closes the eye 300, the pupil 301 may dilate, such that the pupil 301 is initially dilated when the eye 300 is reopened, as represented by graphic 306 having a diameter "$d_2$." The processor may compare changes in diameter of the graphic 306 or the pupil 301 itself to determine the delay for the pupil 301 to return to the diameter "$d_1$" after a blink or other eye closure. This delay or loss of reactivity to visible or invisible light flashes may at least partially indicate a level of drowsiness, a level of impairment, e.g., intoxication, and/or the onset of a medical event, including lethal or terminal events such as brain damage or brain death due to hypoxemia, hypoglycemia, stroke, myocardial infarction, toxins, poisons, and the like.

In addition or alternatively, the processor may determine the approximate eccentricity of the pupil, e.g., as it is partially covered by the eyelid 302. For example, as shown in FIG. 21C, when the eyelid 302 is partially closed, the halo 306 superimposed on the images may adopt an elliptical shape corresponding to a width "w" and height "h" of the exposed portion of the pupil 301. The height "h" may be related to the diameter "$d_1$," i.e., the ratio of the height "h" to diameter "$d_1$" may be equal to or less than one ($h/d_1 \geq 1$), as an indicator of the degree that the eyelid 302 covers the pupil 301. For example, this ratio may reduce from one to zero once the pupil 301 is completely covered by the eyelid 302.

Similarly, the width "w" may also be related to the diameter "$d_1$" ($w//d_1 \geq 1$), as an indicator of the degree that the eyelid 302 covers the pupil 301, e.g., as the eyelid 302 begins to cover more than half of the pupil 301. In addition or alternatively, a ratio of the height and width ($h/w \geq 1$) may relate information on eccentricity of the pupil 301, e.g., based upon coverage by the eyelid 302. Such parameters may be analyzed individually, collectively, and/or along with other oculometric and/or physiological parameters to monitor, analyze and/or predict future behavior of the user. The data may be compared with empirical or other data retained or accessed by the processor to provide information regarding the user's condition, e.g., a COFI value, as described elsewhere herein.

If, for example, the analysis of the user's pupil results in a determination that the user's alertness level has fallen below a predetermined level, a warning may be provided to the user and/or to one or more third persons, similar to other embodiments described herein. Such methods may also be useful to determine whether the user is being affected by drugs, alcohol, and/or medical conditions, as explained elsewhere herein.

In addition, as a threshold and/or to test the user's vigilance, an apparatus or system, such as any of those described herein, may test the user's pupillary response. Such a test may confirm that a patient is active, i.e., not asleep, or even deceased, while wearing the apparatus. For example, if a light source is flashed for a predetermined duration and/or pulse frequency at the user's eye, the user's pupil may dilate briefly from its relaxed state (based upon ambient lighting), and then constrict back to the relaxed state within a predictable period of time.

Figure 22A:
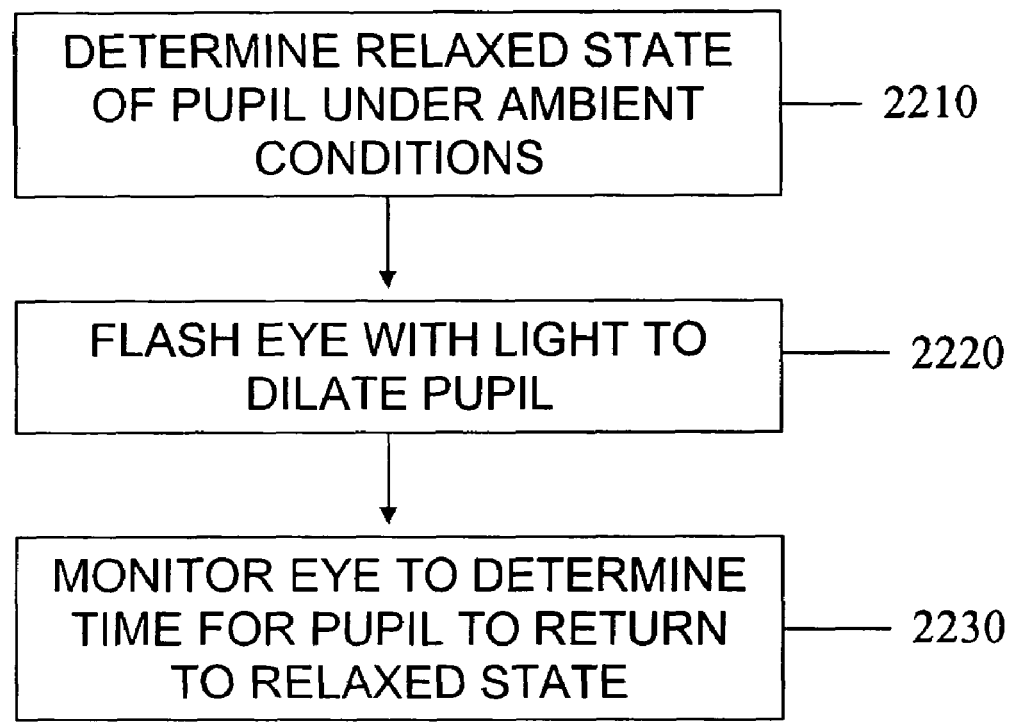
FIG. 22 is a flowchart, showing a method for vigilance testing a user wearing an apparatus for monitoring movement of the user's eyes.

Turning to FIG. 22A, an exemplary method is shown for testing the vigilance of a user of any of the apparatus and systems described herein. For example, a user may wear the apparatus 810 shown in FIG. 18 monitoring one or both of the user's eyes, as described further above. At step 2210, base or parameters of the user's eye(s) may be determined under a related state. For example, the relaxed diameter of the pupil may be measured or otherwise monitored under ambient conditions.

At step 2220, one or more pulses of light may be emitted towards the eye(s), which may cause the eye(s) to dilate and/or constrict from the relaxed state, e.g., at substantially the same frequency as the frequency of pulsed light flashes. For example, one or more emitters on the apparatus 810 may be activated in a predetermined sequence to cause the eye(s) to dilate. Thereafter, in step 2230, the eye(s) of the user may be monitored, e.g., subconsciously or unconsciously with the camera 830 or sensors 822, to determine the reaction time of the eye to return to the relaxed state. The reaction time may be compared to an empirical database or other data to confirm that the user is conscious, awake, and/or alive. If desired, steps 2220 and 2230 may be repeated one or more times to confirm the reaction time and/or provide an average reaction time, if desired, e.g., to avoid false negative determinations.

If the light source is outside the visible light range, e.g., within the infrared range, the pupil may still react to flashes of light in this manner. One advantage of using infrared light is that it may not distract or bother the user, since the user will not consciously observe the light. Yet, the pupil may still react to such flashes sufficiently that a system monitoring the eye may identify when the pupil dilates and constricts in response to such flashes.

It may be sufficient, e.g., during a threshold test, to generate a single flash of light and monitor the pupil's response. Alternatively, a series of flashes may be used to monitor pupillary response over time, e.g., to study trends or eliminate false data that may arise from a single flash. For a series of flashes, the pulse rate should be longer than the time the pupil takes to naturally return to its relaxed state after dilating in response to a flash of light, e.g., at least between about fifty and one hundred milliseconds (50-100 ms). Alternatively, pulses of light, e.g., near-infrared light (having wavelengths between about 640-700 nanometers) may be directed at the user's eye(s). The system may detect rhythmic fluctuations in pupillary response. Such responses may result from a primitive oculometric response, possibly relating to night vision, e.g., "seeing" in the dark or sensing infrared light sources in the dark.

Such pupillary response testing may also be used to identify false positives, e.g., when a user has died, yet the system fails to detect any eye closure and/or movement. Similarly, pupillary response testing may also be able to determine whether a user is asleep or unconscious. In addition, pupillary response testing may be used to determine whether a user is under the influence of alcohol, drugs, and the like, which may affect the rate at which the pupil constricts back to its relaxed state after dilating in response to flashes of light. In addition or alternatively, pupillary response testing may also be used to determine the blood concentration or amount of drug or alcohol in the user's body depending on correlation between oculometric measures and corresponding scientifically-determined blood levels.

Figure 22B:
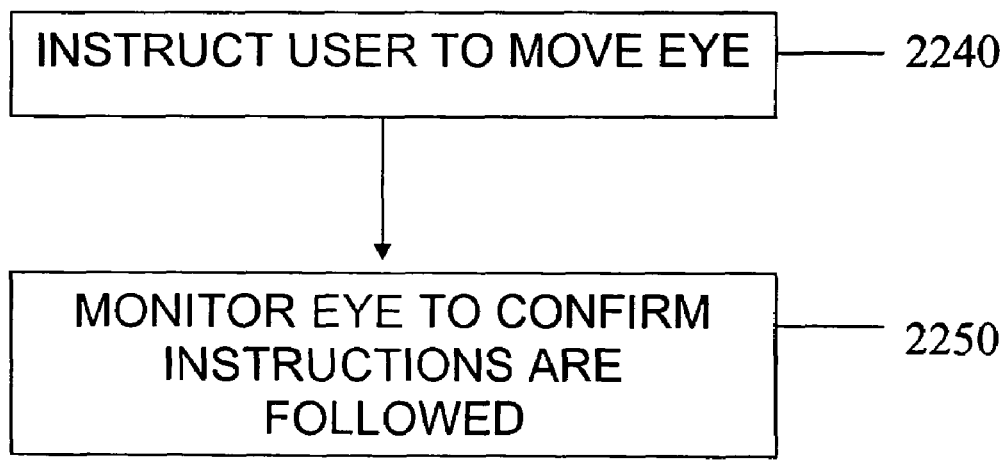

Turning to FIG. 22B, another method for testing threshold vigilance is shown. This method generally involves providing stimuli instructing the user to deliberately move their eye(s) in a desired manner, at step 2240, and monitoring the eye at step 2250, e.g., for deliberate movement confirming that the user has followed the instructions and moved their eye(s) in the desired manner. Any of the apparatus described herein may include one or more stimulus devices, e.g., speakers, lights, vibratory or other tactile devices. Alternatively, such devices may be provided remotely from the user, e.g., on a dashboard of a vehicle, a video display, and the like.

For example, a user may be instructed to close their eye(s) for a predetermined time if a visible light on the apparatus is activated. Once the light is activated, the system may monitor the eye(s) to confirm that the user responds within a predetermined time frame and/or in a predetermined manner (e.g., one or more blinks in a predetermined sequence). Alternatively, other stimuli may be provided instead of light flashes, such as visible instructions on a display (on or separate from the apparatus), audible signals (e.g., verbal commands from a speaker on or near the device), tactile signals, and the like. In these embodiments, the user may be instructed to perform a series of actions, e.g., looking up or down, left or right, blinking in a desired sequence, closing their eye until instructed, following a pointer on a display, and the like. Such testing may be useful to confirm, for example, whether a test subject is awake, aware, and/or alert during a series of tests or while performing various activities.

In another embodiment, apparatus and systems, such as those described elsewhere herein, may be used to control a computer system, e.g., similar to a computer mouse, joystick, and the like. For example, with reference to the apparatus 810 shown and described with reference to FIGS. 13, the camera(s) 830 may be used to monitor the location of the user's pupil(s) to direct and/or activate a mouse pointer on a computer screen or other display. A processor receiving the image data from the camera 922 may analyze the image data to determine the relative location of the pupil(s) within the active area 942 of the detector 940. Optionally, one or more displays may be fixed relative to the frame 812 disposed in front of or within the field of view of one or both of the user's eyes. For example, a flat panel LCD or other display (not shown) may be mounted to the frame 812 in place of lenses. Such an apparatus may be used for simulations, e.g., within a medical or other research facility, for recreational use, e.g., as a video game console, and the like.

Figure 23:
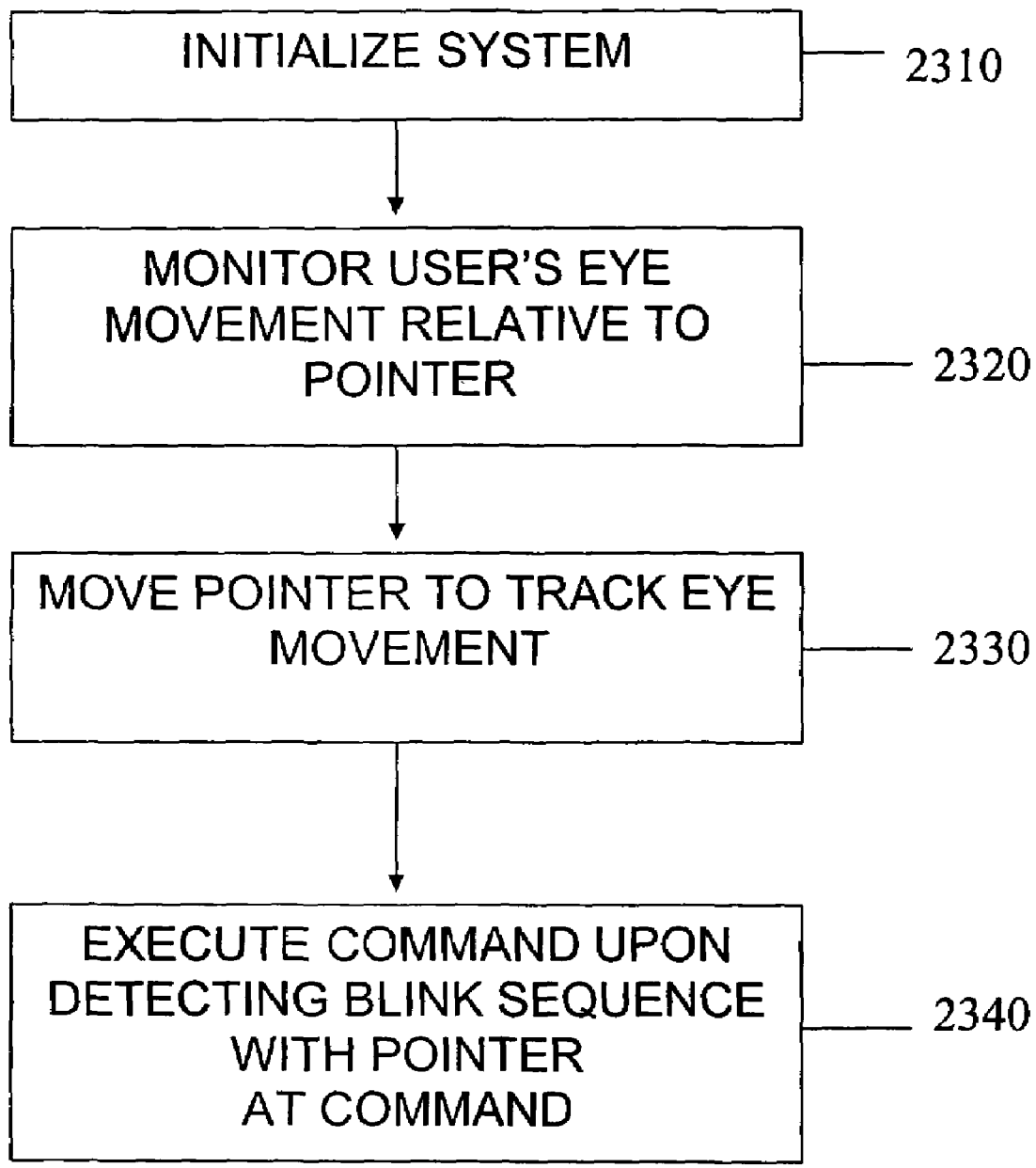
FIG. 23 is a flowchart, showing a method for controlling a computing device based upon movement of an eye.

Turning to FIG. 23, an exemplary method is shown for controlling a computing device based upon detected eye movement using any of the apparatus or systems described herein. For example, the apparatus 910 shown in FIG. 18A may be used that includes a fiberoptic bundle 924 for imaging one or both eyes of the user. Optionally, as explained further below, the apparatus may also carry one or more exocameras, e.g., disposed adjacent one or both eyes of the user that may be oriented outwardly along the user's forward view. First, at step 2310, it may be desirable to initialize a system including such an apparatus, i.e., establish a reference frame, such as a base or reference location, a reference frame with orthogonal components, and the like. For example, the user may be instructed to look at a pointer or other predetermined location on the display, thereby maintaining the user's eye(s), and consequently the user's pupil(s) substantially stationary. The processor may analyze the image data from the camera 830 while the user's eye(s) are substantially stationary, e.g., to determine the location of the pupil on the images that corresponds to the reference point or "base location." For example, the pointer or base location may be located substantially straight ahead of the user's pupil. Optionally, the user may be instructed to look sequentially at two or more identified locations on the display, thereby providing a scale for relative movement of the user's eye. In this alternative, it may be desirable to have the user look at opposite corners of the display, e.g., to identify the limits of appropriate eye movement relative to the display.

Once initialization is complete, the user may be free to move their eye(s), e.g., left and right, up and down, e.g., relative to the pointer and/or the rest of the display. At step 2320, the system may monitor such movement of the eye, i.e., the processor may analyze the image data to determine the relative location of the user's pupil(s) from the base location(s). For example, if the user moves his/her eye(s) up and right from the base location, i.e., up and right relative to the pointer on the computer screen, the processor may determine this movement. In response, at step 2330, the processor may move the pointer up and right, i.e., thereby tracking the user's gaze. When the user stops moving his/her eye(s), the processor may stop the pointer once it arrives at the location where the user is currently looking on the display.

Optionally, at step 2340, the user may be able to execute a command once the pointer has moved to a desired location on the display, e.g., similar to activating a button on a mouse. For example, the processor may monitor the image data for a signal from the user, e.g., one or more purposeful blinks in a predetermined sequence. This may be as simple as a single blink of a predetermined duration, e.g., several seconds long, to a more complicated series of blinks, e.g., including one or both of the user's eyes. Alternatively, the signal may be a predetermined period with no blinks, e.g., three, five, or more seconds long. When the processor identifies the signal, the processor may activate the command. For example, the user may stop moving their eye(s) when it reaches an icon, word command, and the like on the display, and the processor may move the point until it overlies or otherwise is located at the icon or command. The user may then blink or act, as explained above, similar to a "double-click" of a button on a computer mouse, thereby instructing the processor to complete the selected command or communicate the selected command to a desired destination. For example, the selected command may result in a computer program being executed, or a piece of equipment or other device being activated, deactivated, or otherwise controlled in a desired manner. Thus, the system may be used to complete a variety of tasks, from controlling a computer device coupled to the processor and/or display, to turning on or off a light switch or vehicle. Such apparatus and/or systems may thereby provide methods for using a computer hands-free, i.e., using only movement of the user's eye(s).

For example, in one application, the system may be used to operate a vehicle, such as a helicopter, jet, or other aircraft, e.g., to activate or otherwise control weapons, navigational, or other onboard systems. In another application, the system may be used in a video game or other simulation, e.g., to enhance virtual reality immersion. For example, the system may allow a user to quickly navigate through multiple menus, scenes, or other activities, while leaving the user's hands free to perform other functions, e.g., perform other activities in addition or simultaneously with eye-controlled functions, which may allow more and/or more complicated tasks at the same time.

In addition, one or more exocameras may be used to enhance and/or otherwise facilitate tracking eye movement relative to the pointer on the display. For example, an exocamera may be provided adjacent at least one eye, e.g., at a predetermined distance or other relationship from the eye, that is oriented towards the display. Thus, the exocamera may provide images of the display, e.g., showing movement of the pointer in real time that may synchronized with movement of the eye monitored with the endocamera. The processor may relate this data using triangulation or other algorithms to enhance accuracy of tracking the pointer with eye movement. This may ensure the accuracy that, when the user intends to execute a command by blinking with the pointer on a command, the intended command is actually selected, e.g., when the display shows multiple available commands.

In addition, such systems and methods may be used in medical or other diagnostic procedures, such as vigilance testing. For example, the processor may analyze data from the endocameras and exocameras to correlate movement of the eye(s) relative to images on the display to study a variety of oculometric parameters, such as slow rolling eye movement, poor eye fixation and/or tracking, wandering gaze, increased eye blinking, hypnotic staring, prolonged eyelid droops or blinking, slow velocity eyelid opening and closing, startled eyelid opening velocities, long-term pupillary constrictive changes, unstable pupil diameters, obscured visual-evoked pupil reactions, and/or other parameters discussed elsewhere herein. These procedures may be used to study an individual's responsive faced with various environmental, alcohol or drug-induced, and/or other conditions.

Figure 24:
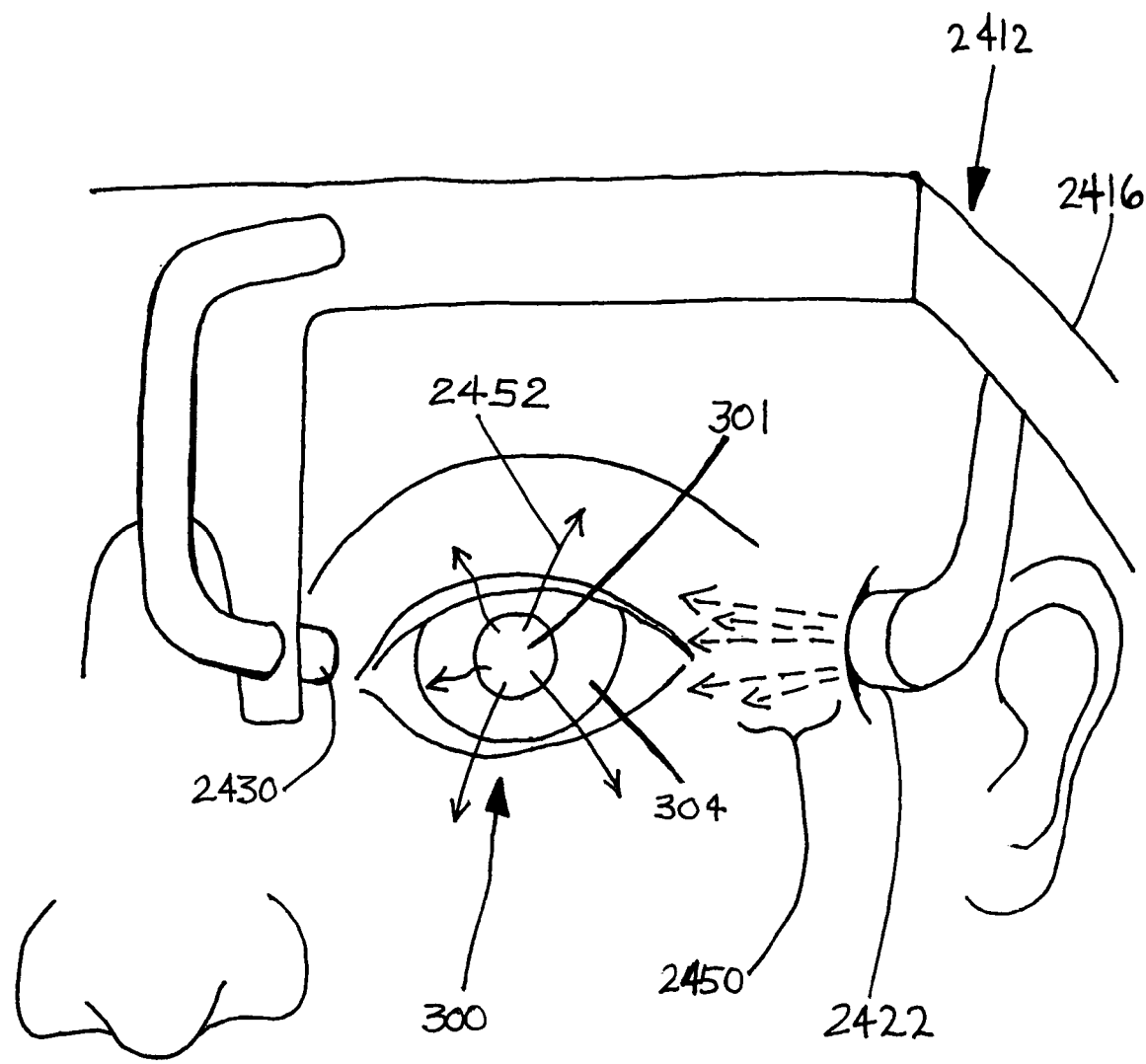
FIG. 24 is a front view of an apparatus for transcutaneously transmitting light to an eye and detecting emitted light exiting from the pupil of the eye.

Turning to FIG. 24, in another embodiment, an apparatus 2410 may be provided for transcutaneously lighting an eye 300 of a user wearing the apparatus 2410. The apparatus 2410 may be generally similar to any of the embodiments described herein, such as the frame 812 shown in FIG. 13. As shown, the apparatus 2410 may include one or more emitters or other light source(s) 2422 that contact the user's head 308, e.g., the user's temple(s) adjacent one or both eyes 300 (one shown for simplicity). In addition, the apparatus 2410 may include one or more sensors, such as fiberoptic bundle 2430, e.g., terminating in a lens 2434 for acquiring images of the user's eye 300.

In one exemplary embodiment, an infrared emitter 2422 may be fixedly or adjustably mounted on one or both ear pieces 2422 of a frame 2412 such that the emitter 2422 contacts and transmits light towards the user's skin. For example, the emitter 2422 may include a plurality of LEDs, which may be emit collimated, non-coherent (non-laser) infrared light. The emitter 2422 may be oriented generally towards the eye 300 such that light from the emitter 2422 may travel through or along the user's head 308 into the eye 300, as represented by dashed arrows 2450. For example, it has been found that skin and other tissue may be at least translucent to certain frequencies of light, such as infrared light. Thus, at least some of the light from the emitter(s) 2422 may transmit transcutaneously along or through the user's skin and/or other tissue until at least some of the light enters the eye 300.

The light may reflect off of the retina (not shown) within the eye 300, such that at least some of the light escapes out of the pupil 301, as represented by arrows 2452. The lens 2434 and fiberoptic bundle 2430 may relay images of the eye to a detector (not shown), similar to other embodiments described herein, which may identify the pupil 301 as a bright spot on the images due to the light 2452. A processor or other device coupled to the detector may monitor the pupil 301, such as its relative location on the images, size, and/or shape, similar to other embodiments described herein, e.g., using the "white pupil" or "dark pupil" techniques described elsewhere herein. In addition or alternatively, the transcutaneous light may illuminate the entire eye 300, especially the retina, which may be observed from in front of the user's face, e.g., as a dimmer sphere or other shape with the pupil 301 showing as a bright spot surrounded by the dimmer shape.

This embodiment may have the advantage that one or more emitters do not have be positioned in front of the user's eye, which may partially obstruct or distract the user's field of view. Furthermore, because this system uses infrared sensing cameras and/or detectors that operated independently of the angle of incident infrared light, this embodiment may eliminate technical difficulties arising out of a loss of proper orientation of emitters to detectors. In addition, without emitter(s) in front of the eye, glint or other reflections off of the eye may be eliminated, which may facilitate analyzing the image data.

It will be appreciated that the various components and features described with the particular embodiments may be added, deleted, and/or substituted with the other embodiments, depending upon the intended use of the embodiments. For example, Appendices A and B of provisional application Ser. No. 60/559,135, incorporated by reference herein, provide additional information on possible structural features, and/or methods for using the apparatus and systems described herein. The entire disclosures of Appendices A and B are expressly incorporated herein by reference.

While the invention is susceptible to various modifications, and alternative forms, specific examples thereof have been shown in the drawings and are herein described in detail. It should be understood that the invention is not to be limited to the particular forms or methods disclosed, but to the contrary, the invention is to cover all modifications, equivalents and alternatives falling within the scope of the appended claims.

I claim:

1. A system for monitoring movement of a person's eye, comprising:
   a device configured to be worn on a person's head; a light source for directing light towards an eye of the person when the device is worn;
   a camera on the device for monitoring movement of the eye, the camera configured for generating video signals representing video images acquired by the camera of the eye;
   a processor communicating with the camera for processing the video signals to analyze a pupil of the eye by identifying the pupil of the eye from the video signals and monitoring at least one of a size of the pupil and an eccentricity of the pupil; the processor is further configured for correlating the video signals to determine the person's physical or mental state based at least partially upon analysis of the pupil identified by the processor; and
   a display coupled to the processor for displaying video images of the eye from the video signals processed by the processor, the display superimposing a graphic onto the video images to identify the pupil.

2. The system of claim 1, wherein the camera comprises a CCD or CMOS detector, and at least one fiber optic bundle including a first end mounted to the device such that the first end is oriented towards an eye of the person when the device is worn.

3. The system of claim 2, wherein the light source comprises at least one illumination fiber carried by the fiber optic bundle.

4. The system of claim 1, further comprising a transmitter on the device for wirelessly transmitting output signals from the camera to a remote location.

5. The system of claim 4, wherein the processor is located at a location remote to the device, the processor coupled to a receiver for receiving the output signals transmitted by the transmitter.

6. The system of claim 1, wherein the processor is provided on the device.

7. The system of claim 1, further comprising one or more sensors on the device for measuring one or more physiological characteristics of the person, the processor coupled to the one or more sensors for correlating the one or more physiological characteristics with the video signals to determine to the person's physical or mental state.

8. The system of claim 1, further comprising one or more sensors on the device for measuring one or more physiological characteristics of the user, the processor coupled to the one or more sensors for displaying the one or more physiological characteristics on the display along with the video images.

9. A method for monitoring movement of a person's eye, comprising:
   placing a head-wearable biosensor assembly on a person's head, the biosensor assembly including a light source for directing light towards an eye of the person when the biosensor assembly is worn, and a camera oriented towards the eye;
   emitting light from the light source towards the eye;
   monitoring movement of the eye with the camera to generate video images of the eye;
   correlating the video images and determining the person's physical or metal state by a processor; and
   generating by the processor a graphical output of the movement monitored by the camera, the graphical output comprising an artificial image superimposed upon the video images of the eye to identify at least one of a size of a pupil of the eye and an eccentricity of the pupil.

10. The method of claim 9, wherein correlating the video images to determine the person's physical or mental state comprises analyzing the video images to monitor at least one of a relative location of the pupil, a size of the pupil, and an eccentricity of the pupil.

11. The method of claim 9, wherein correlating the video images to determine the person's physical or mental state comprises monitoring changes in size of the pupil.

12. The method of claim 11, wherein monitoring changes in size of the pupil comprises:
   detecting initial dilation of the pupil after the person closes and reopens the eye; and
   determining a delay of the pupil to return to a relaxed size after the eye is reopened.

13. The method of claim 11, wherein monitoring changes in size of the pupil comprises:
   determining eccentricity of the pupil; and
   comparing the eccentricity of the pupil to data to determine the person's physical or mental state.

14. The method of claim 9, further comprising transmitting the video images from the camera to a remote location, and wherein the graphical output is generated at the remote location.

15. The method of claim 9, wherein the graphical output is displayed in real time on a display.

16. The method of claim 9, wherein the biosensor assembly further comprises one or more sensors for measuring one or more physiological characteristics of the person, and wherein the one or more physiological characteristics are correlated with the video images to determine to the person's physical or mental state.

17. The method of claim 9, wherein the biosensor assembly further comprises one or more sensors for measuring one or more physiological characteristics of the user, and wherein the one or more physiological characteristics are displayed on a display along with the video images.

18. The method of claim 9, wherein generating the graphical output comprises detecting contrast between the edge of the pupil and the surrounding iris of the eye.

19. The method of claim 18, wherein generating the graphical output further comprises creating a graphic halo or ellipse that is superimposed on the video images.

20. A method for monitoring a person's eye, comprising:
placing a head-wearable biosensor assembly on a person's head, the biosensor assembly comprising a light source directing light towards the person's eye and a camera oriented towards the person's eye that do not interfere substantially with the user's vision;
emitting one or more pulses of light from the fight source, causing the eye to dilate from its relaxed state;
monitoring the eye with the camera to determine the reaction time of the eye to return to its relaxed state;
comparing the reaction time to reference data by a processor to determine the person's physical or mental state; and
displaying video images of the eye from the video signals processed by the processor; the processor superimposing a graphic onto the video images to identify at least one of a size of the pupil and an eccentricity of the pupil.

21. The method of claim 20, wherein comparing the reaction time comprises comparing the reaction time to reference data to confirm that the person is at least one of conscious, awake, and alive.

22. The method of claim 20, wherein emitting one or more pulses of light from the light source, causing the eye to dilate from its relaxed state; and monitoring the eye with the camera to determine the reaction time of the eye to return to its relaxed state is repeated one or more times to avoid false negative determinations.

23. The method of claim 20, wherein the light source is outside the visible light range such that the person does not consciously observe the one or more pulses of light.

24. The method of claim 20, wherein comparing the reaction time comprises comparing the reaction time to reference data to determine whether the person is under the influence of alcohol or drugs.

25. The method of claim 20, wherein comparing the reaction time comprises comparing the reaction time to reference data to determine the amount of drug or alcohol in the person's body.

26. A system for monitoring movement of a person's eye, comprising:
a device configured to be worn on a person's head;
a light source for directing light towards an eye of the person when the device is worn;
a camera on the device for monitoring movement of the eye, the camera configured for generating video signals representing video images acquired by the camera of the eye;
a processor communicating with the camera for processing the video signals to analyze a pupil of the eye by identifying the pupil of the eye from the video signals and at least one of a size of the pupil and an eccentricity of the pupil, the processor correlating the video signals to determine the person's physical or mental state based at least partially upon the analysis of the pupil; and
a display coupled to the processor for displaying video images of the eye from the video signals processed by the processor the display superimposing a graphic onto the video images to identify at least one of a size of the pupil and an eccentricity of the pupil.

27. The system of claim 26, further comprising one or more sensors on the device for measuring one or more physiological characteristics of the user, the processor coupled to the one or more sensors for displaying the one or more physiological characteristics on the display along with the video images.

28. The system of claim 26, further comprising one or more sensors on the device for measuring one or more physiological characteristics of the person, the processor coupled to the one or more sensors for correlating the one or more physiological characteristics with the video signals to determine to the person's physical or mental state.

* * * * *